US008133720B2

(12) United States Patent
Ono et al.

(10) Patent No.: US 8,133,720 B2
(45) Date of Patent: Mar. 13, 2012

(54) BIOSENSOR

(75) Inventors: Shizuko Ono, Tokyo (JP); Yayoi Takahashi, Nikaho (JP)

(73) Assignee: TDK Corporation, Tokyo (JP)

( * ) Notice: Subject to any disclaimer, the term of this patent is extended or adjusted under 35 U.S.C. 154(b) by 399 days.

(21) Appl. No.: 12/235,336

(22) Filed: Sep. 22, 2008

(65) Prior Publication Data

US 2009/0087867 A1 Apr. 2, 2009

(30) Foreign Application Priority Data

Sep. 27, 2007 (JP) ................................ P2007-252148

(51) Int. Cl.
*C12M 1/34* (2006.01)
*A61K 39/09* (2006.01)
*G01N 33/543* (2006.01)

(52) U.S. Cl. .................. 435/287.2; 424/244.1; 436/518; 204/403

(58) Field of Classification Search ............... 435/287.2; 424/244.1; 436/518; 204/403
See application file for complete search history.

(56) References Cited

U.S. PATENT DOCUMENTS

2003/0124635 A1 7/2003 Ukaji et al.
2003/0207256 A1* 11/2003 Sayre et al. ........................ 435/5

FOREIGN PATENT DOCUMENTS

JP A-2002-267673 9/2002
JP A-2003-183299 7/2003
WO WO 2005/032582 * 4/2005

OTHER PUBLICATIONS

Whittaker, C.J., et al. Annual Review of Microbiology, vol. 50, pp. 513-552, 1996.*

* cited by examiner

*Primary Examiner* — Rodney P. Swartz
(74) *Attorney, Agent, or Firm* — Oliff & Berridge, PLC

(57) ABSTRACT

The invention provides a biosensor comprising a microbe-binding aptamer(s) in the substrate recognition element. It is possible to obtain a stabilized biosensor wherein the detection sensitivity for target microbe (target bacterium) is not impaired depending on the storage condition or measuring sample, and target bacterium in a body fluid can be directly measured by insertion of the substrate recognition element of the biosensor.

4 Claims, 5 Drawing Sheets

OUTPUT (nA)
50.0
45.0
40.0
35.0
30.0
25.0
20.0
15.0
10.0
5.0
0.0
1×10^4
1×10^5
1×10^6
1×10^7
1×10^8
1×10^9
CELL CONCENTRATION (CFU/ml)
10nA
10min

SEQUENCE LISTING

```
<160> NUMBER OF SEQ ID NOS: 50

<210> SEQ ID NO 1
<211> LENGTH: 1562
<212> TYPE: PRT
<213> ORGANISM: Streptococcus mutans

<400> SEQUENCE: 1

Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Glu Ala Glu Gln Ser Gln Asn Gln
65                  70                  75                  80

Ala Gly Glu Thr Asn Gly Ser Ile Pro Val Glu Val Pro Lys Thr Asp
                85                  90                  95

Leu Asp Gln Ala Ala Lys Asp Ala Lys Ser Ala Gly Val Asn Val Val
            100                 105                 110

Gln Asp Ala Asp Val Asn Lys Gly Thr Val Lys Thr Ala Glu Glu Ala
        115                 120                 125
```

```
Val Gln Lys Glu Thr Glu Ile Lys Glu Asp Tyr Thr Lys Gln Ala Glu
    130                 135                 140

Asp Ile Lys Lys Thr Thr Asp Gln Tyr Lys Ser Asp Val Ala Ala His
145                 150                 155                 160

Glu Ala Glu Val Ala Lys Ile Lys Ala Lys Asn Gln Ala Thr Lys Glu
                165                 170                 175

Gln Tyr Glu Lys Asp Met Ala Ala His Lys Ala Glu Val Glu Arg Ile
            180                 185                 190

Asn Ala Ala Asn Ala Ala Ser Lys Thr Ala Tyr Glu Ala Lys Leu Ala
        195                 200                 205

Gln Tyr Gln Ala Asp Leu Ala Ala Val Gln Lys Thr Asn Ala Ala Asn
    210                 215                 220

Gln Ala Ala Tyr Gln Lys Ala Leu Ala Ala Tyr Gln Ala Glu Leu Lys
225                 230                 235                 240

Arg Val Gln Glu Ala Asn Ala Ala Ala Lys Ala Ala Tyr Asp Thr Ala
                245                 250                 255

Val Ala Ala Asn Asn Ala Lys Asn Thr Glu Ile Ala Ala Ala Asn Glu
            260                 265                 270

Glu Ile Arg Lys Arg Asn Ala Thr Ala Lys Ala Glu Tyr Glu Thr Lys
        275                 280                 285

Leu Ala Gln Tyr Gln Ala Glu Leu Lys Arg Val Gln Glu Ala Asn Ala
    290                 295                 300

Ala Asn Glu Ala Asp Tyr Gln Ala Lys Leu Thr Ala Tyr Gln Thr Glu
305                 310                 315                 320

Leu Ala Arg Val Gln Lys Ala Asn Ala Asp Ala Lys Ala Ala Tyr Glu
                325                 330                 335

Ala Ala Val Ala Ala Asn Asn Ala Lys Asn Ala Ala Leu Thr Ala Glu
            340                 345                 350

Asn Thr Ala Ile Lys Gln Arg Asn Glu Asn Ala Lys Ala Thr Tyr Glu
        355                 360                 365

Ala Ala Leu Lys Gln Tyr Glu Ala Asp Leu Ala Ala Val Lys Lys Ala
    370                 375                 380

Asn Ala Ala Asn Glu Ala Asp Tyr Gln Ala Lys Leu Thr Ala Tyr Gln
385                 390                 395                 400

Thr Glu Leu Ala Arg Val Gln Lys Ala Asn Ala Asp Ala Lys Ala Ala
                405                 410                 415

Tyr Glu Ala Ala Val Ala Ala Asn Asn Ala Ala Asn Ala Ala Leu Thr
            420                 425                 430

Ala Glu Asn Thr Ala Ile Lys Lys Arg Asn Ala Asp Ala Lys Ala Asp
        435                 440                 445

Tyr Glu Ala Lys Leu Ala Lys Tyr Gln Ala Asp Leu Ala Lys Tyr Gln
    450                 455                 460

Lys Asp Leu Ala Asp Tyr Pro Val Lys Leu Lys Ala Tyr Glu Asp Glu
465                 470                 475                 480

Gln Ala Ser Ile Lys Ala Ala Leu Ala Glu Leu Glu Lys His Lys Asn
                485                 490                 495

Glu Asp Gly Asn Leu Thr Glu Pro Ser Ala Gln Asn Leu Val Tyr Asp
            500                 505                 510

Leu Glu Pro Asn Ala Asn Leu Ser Leu Thr Thr Asp Gly Lys Phe Leu
        515                 520                 525

Lys Ala Ser Ala Val Asp Asp Ala Phe Ser Lys Ser Thr Ser Lys Ala
    530                 535                 540

Lys Tyr Asp Gln Lys Ile Leu Gln Leu Asp Asp Leu Asp Ile Thr Asn
```

```
545                 550                 555                 560

Leu Glu Gln Ser Asn Asp Val Ala Ser Ser Met Glu Leu Tyr Gly Asn
                565                 570                 575

Phe Gly Asp Lys Ala Gly Trp Ser Thr Thr Val Ser Asn Asn Ser Gln
            580                 585                 590

Val Lys Trp Gly Ser Val Leu Leu Glu Arg Gly Gln Ser Ala Thr Ala
        595                 600                 605

Thr Tyr Thr Asn Leu Gln Asn Ser Tyr Tyr Asn Gly Lys Lys Ile Ser
    610                 615                 620

Lys Ile Val Tyr Lys Tyr Thr Val Asp Pro Lys Ser Lys Phe Gln Gly
625                 630                 635                 640

Gln Lys Val Trp Leu Gly Ile Phe Thr Asp Pro Thr Leu Gly Val Phe
                645                 650                 655

Ala Ser Ala Tyr Thr Gly Gln Val Glu Lys Asn Thr Ser Ile Phe Ile
            660                 665                 670

Lys Asn Glu Phe Thr Phe Tyr Asp Glu Asp Gly Lys Pro Ile Asn Phe
        675                 680                 685

Asp Asn Ala Leu Leu Ser Val Ala Ser Leu Asn Arg Glu Asn Asn Ser
    690                 695                 700

Ile Glu Met Ala Lys Asp Tyr Thr Gly Lys Phe Val Lys Ile Ser Gly
705                 710                 715                 720

Ser Ser Ile Gly Glu Lys Asn Gly Met Ile Tyr Ala Thr Asp Thr Leu
                725                 730                 735

Asn Phe Arg Gln Gly Gln Gly Gly Ala Arg Trp Thr Met Tyr Thr Arg
            740                 745                 750

Ala Ser Glu Pro Gly Ser Gly Trp Asp Ser Ser Asp Ala Pro Asn Ser
        755                 760                 765

Trp Tyr Gly Ala Gly Ala Ile Arg Met Ser Gly Pro Asn Asn Ser Val
    770                 775                 780

Thr Leu Gly Ala Ile Ser Ser Thr Leu Val Val Pro Ala Asp Pro Thr
785                 790                 795                 800

Met Ala Ile Glu Thr Gly Lys Lys Pro Asn Ile Trp Tyr Ser Leu Asn
                805                 810                 815

Gly Lys Ile Arg Ala Val Asn Val Pro Lys Val Thr Lys Glu Lys Pro
            820                 825                 830

Thr Pro Pro Val Lys Pro Thr Ala Pro Thr Lys Pro Thr Tyr Glu Thr
        835                 840                 845

Glu Lys Pro Leu Lys Pro Ala Pro Val Ala Pro Asn Tyr Glu Lys Glu
    850                 855                 860

Pro Thr Pro Pro Thr Arg Thr Pro Asp Gln Ala Glu Pro Asn Lys Pro
865                 870                 875                 880

Thr Pro Pro Thr Tyr Glu Thr Glu Lys Pro Leu Glu Pro Ala Pro Val
                885                 890                 895

Glu Pro Ser Tyr Glu Ala Glu Pro Thr Pro Pro Thr Arg Thr Pro Asp
            900                 905                 910

Gln Ala Glu Pro Asn Lys Pro Thr Pro Pro Thr Tyr Glu Thr Glu Lys
        915                 920                 925

Pro Leu Glu Pro Ala Pro Val Glu Pro Ser Tyr Glu Ala Glu Pro Thr
    930                 935                 940

Pro Pro Thr Pro Thr Pro Asp Gln Pro Glu Pro Asn Lys Pro Val Glu
945                 950                 955                 960

Pro Thr Tyr Glu Val Ile Pro Thr Pro Pro Thr Asp Pro Val Tyr Gln
                965                 970                 975
```

```
Asp Leu Pro Thr Pro Pro Ser Val Pro Thr Val His Phe His Tyr Phe
            980                 985                 990

Lys Leu Ala Val Gln Pro Gln Val  Asn Lys Glu Ile Arg  Asn Asn Asn
        995                 1000                 1005

Asp Ile  Asn Ile Asp Arg Thr  Leu Val Ala Lys Gln  Ser Val Val
    1010                 1015                 1020

Lys Phe  Gln Leu Lys Thr Ala  Asp Leu Pro Ala Gly  Arg Asp Glu
    1025                 1030                 1035

Thr Thr  Ser Phe Val Leu Val  Asp Pro Leu Pro Ser  Gly Tyr Gln
    1040                 1045                 1050

Phe Asn  Pro Glu Ala Thr Lys  Ala Ala Ser Pro Gly  Phe Asp Val
    1055                 1060                 1065

Thr Tyr  Asp Asn Ala Thr Asn  Thr Val Thr Phe Lys  Ala Thr Ala
    1070                 1075                 1080

Ala Thr  Leu Ala Thr Phe Asn  Ala Asp Leu Thr Lys  Ser Val Ala
    1085                 1090                 1095

Thr Ile  Tyr Pro Thr Val Val  Gly Gln Val Leu Asn  Asp Gly Ala
    1100                 1105                 1110

Thr Tyr  Lys Asn Asn Phe Thr  Leu Thr Val Asn Asp  Ala Tyr Gly
    1115                 1120                 1125

Ile Lys  Ser Asn Val Val Arg  Val Thr Thr Pro Gly  Lys Pro Asn
    1130                 1135                 1140

Asp Pro  Asp Asn Pro Asn Asn  Asn Tyr Ile Lys Pro  Thr Lys Val
    1145                 1150                 1155

Asn Lys  Asn Glu Asn Gly Val  Val Ile Asp Gly Lys  Thr Val Leu
    1160                 1165                 1170

Ala Gly  Ser Thr Asn Tyr Tyr  Glu Leu Thr Trp Asp  Leu Asp Gln
    1175                 1180                 1185

Tyr Lys  Asn Asp Arg Ser Ser  Ala Asp Thr Ile Gln  Lys Gly Phe
    1190                 1195                 1200

Tyr Tyr  Val Asp Asp Tyr Pro  Glu Glu Ala Leu Glu  Leu Arg Gln
    1205                 1210                 1215

Asp Leu  Val Lys Ile Thr Asp  Ala Asn Gly Asn Glu  Val Thr Gly
    1220                 1225                 1230

Val Ser  Val Asp Asn Tyr Thr  Asn Leu Glu Ala Ala  Pro Gln Glu
    1235                 1240                 1245

Ile Arg  Asp Val Leu Ser Lys  Ala Gly Ile Arg Pro  Lys Gly Ala
    1250                 1255                 1260

Phe Gln  Ile Phe Arg Ala Asp  Asn Pro Arg Glu Phe  Tyr Asp Thr
    1265                 1270                 1275

Tyr Val  Lys Thr Gly Ile Asp  Leu Lys Ile Val Ser  Pro Met Val
    1280                 1285                 1290

Val Lys  Lys Gln Met Gly Gln  Thr Gly Gly Ser Tyr  Glu Asn Gln
    1295                 1300                 1305

Ala Tyr  Gln Ile Asp Phe Gly  Asn Gly Tyr Ala Ser  Asn Ile Ile
    1310                 1315                 1320

Ile Asn  Asn Val Pro Lys Ile  Asn Pro Lys Lys Asp  Val Thr Leu
    1325                 1330                 1335

Thr Leu  Asp Pro Ala Asp Thr  Asn Asn Val Asp Gly  Gln Thr Ile
    1340                 1345                 1350

Pro Leu  Asn Thr Val Phe Asn  Tyr Arg Leu Ile Gly  Gly Ile Ile
    1355                 1360                 1365

Pro Ala  Asp His Ser Glu Glu  Leu Phe Glu Tyr Asn  Phe Tyr Asp
    1370                 1375                 1380
```

```
Asp Tyr  Asp Gln Thr Gly Asp  His Tyr Thr Gly Gln  Tyr Lys Val
    1385                 1390                 1395

Phe Ala  Lys Val Asp Ile Thr  Phe Lys Asp Gly Ser  Ile Ile Lys
    1400                 1405                 1410

Ser Gly  Ala Glu Leu Thr Gln  Tyr Thr Thr Ala Glu  Val Asp Thr
    1415                 1420                 1425

Ala Lys  Gly Ala Ile Thr Ile  Lys Phe Lys Glu Ala  Phe Leu Arg
    1430                 1435                 1440

Ser Val  Ser Ile Asp Ser Ala  Phe Gln Ala Glu Ser  Tyr Ile Gln
    1445                 1450                 1455

Met Lys  Arg Ile Ala Val Gly  Thr Phe Glu Asn Thr  Tyr Ile Asn
    1460                 1465                 1470

Thr Val  Asn Gly Val Thr Tyr  Ser Ser Asn Thr Val  Lys Thr Thr
    1475                 1480                 1485

Thr Pro  Glu Asp Pro Thr Asp  Pro Thr Asp Pro Gln  Asp Pro Ser
    1490                 1495                 1500

Ser Pro  Arg Thr Ser Thr Val  Ile Asn Tyr Lys Pro  Gln Ser Thr
    1505                 1510                 1515

Ala Tyr  Gln Pro Ser Ser Val  Gln Glu Thr Leu Pro  Asn Thr Gly
    1520                 1525                 1530

Val Thr  Asn Asn Ala Tyr Met  Pro Leu Leu Gly Ile  Ile Gly Leu
    1535                 1540                 1545

Val Thr  Ser Phe Ser Leu Leu  Gly Leu Lys Ala Lys  Lys Asp
    1550                 1555                 1560


<210> SEQ ID NO 2
<211> LENGTH: 453
<212> TYPE: PRT
<213> ORGANISM: Streptococcus mutans

<400> SEQUENCE: 2

Met Lys Met Lys Arg Lys Leu Leu Ser Leu Val Ser Val Leu Thr Ile
1               5                   10                  15

Leu Leu Gly Ala Phe Trp Val Thr Lys Ile Val Lys Ala Asp Gln Val
            20                  25                  30

Thr Asn Tyr Thr Asn Thr Ala Ser Ile Thr Lys Ser Asp Gly Thr Ala
        35                  40                  45

Leu Ser Asn Asp Pro Ser Lys Ala Val Asn Tyr Trp Glu Pro Leu Ser
    50                  55                  60

Phe Ser Asn Ser Ile Thr Phe Pro Asp Glu Val Ser Ile Lys Ala Gly
65                  70                  75                  80

Asp Thr Leu Thr Ile Lys Leu Pro Glu Gln Leu Gln Phe Thr Thr Ala
                85                  90                  95

Leu Thr Phe Asp Val Met His Thr Asn Gly Gln Leu Ala Gly Lys Ala
            100                 105                 110

Thr Thr Asp Pro Asn Thr Gly Glu Val Thr Val Thr Phe Thr Asp Ile
        115                 120                 125

Phe Glu Lys Leu Pro Asn Asp Lys Ala Met Thr Leu Asn Phe Asn Ala
    130                 135                 140

Gln Leu Asn His Asn Asn Ile Ser Ile Pro Gly Val Val Asn Phe Asn
145                 150                 155                 160

Tyr Asn Asn Val Ala Tyr Ser Ser Tyr Val Lys Asp Lys Asp Ile Thr
                165                 170                 175

Pro Ile Ser Pro Asp Val Asn Lys Val Gly Tyr Gln Asp Lys Ser Asn
            180                 185                 190
```

```
Pro Gly Leu Ile His Trp Lys Val Leu Ile Asn Asn Lys Gln Gly Ala
        195                 200                 205

Ile Asp Asn Leu Thr Leu Thr Asp Val Val Gly Glu Asp Gln Glu Ile
    210                 215                 220

Val Lys Asp Ser Leu Val Ala Ala Arg Leu Gln Tyr Ile Ala Gly Asp
225                 230                 235                 240

Asp Val Asp Ser Leu Asp Glu Ala Ala Ser Arg Pro Tyr Ala Glu Asp
                245                 250                 255

Phe Ser Lys Asn Val Thr Tyr Gln Thr Asn Asp Leu Gly Leu Thr Thr
            260                 265                 270

Gly Phe Thr Tyr Thr Ile Pro Gly Ser Ser Asn Asn Ala Ile Phe Ile
        275                 280                 285

Ser Tyr Thr Thr Arg Leu Thr Ser Ser Gln Ser Ala Gly Lys Asp Val
    290                 295                 300

Ser Asn Thr Ile Ala Ile Ser Gly Asn Asn Ile Asn Tyr Ser Asn Gln
305                 310                 315                 320

Thr Gly Tyr Ala Arg Ile Glu Ser Ala Tyr Gly Arg Ala Ser Ser Arg
                325                 330                 335

Val Lys Arg Gln Ala Glu Thr Thr Thr Val Thr Glu Thr Thr Thr Ser
            340                 345                 350

Ser Ser Ser Glu Thr Thr Thr Ser Glu Ala Thr Thr Glu Thr Ser Ser
        355                 360                 365

Thr Thr Asn Asn Asn Ser Thr Thr Thr Glu Thr Ala Thr Ser Thr Thr
    370                 375                 380

Gly Ala Ser Thr Thr Gln Thr Lys Thr Thr Ala Ser Gln Thr Asn Val
385                 390                 395                 400

Pro Thr Thr Thr Asn Ile Thr Thr Thr Ser Lys Gln Val Thr Lys Gln
                405                 410                 415

Lys Ala Lys Phe Val Leu Pro Ser Thr Gly Glu Gln Ala Gly Leu Leu
            420                 425                 430

Leu Thr Thr Val Gly Leu Val Ile Val Ala Val Ala Gly Val Tyr Phe
        435                 440                 445

Tyr Arg Thr Arg Arg
    450


<210> SEQ ID NO 3
<211> LENGTH: 565
<212> TYPE: PRT
<213> ORGANISM: Streptococcus mutans

<400> SEQUENCE: 3

Met Met Lys Glu Lys Thr Arg Phe Lys Leu His Lys Val Lys Lys Gln
1               5                   10                  15

Trp Met Ala Ile Ala Val Thr Ser Leu Ala Leu Ala Ala Ile Leu Ser
            20                  25                  30

Gly Ala His Leu Thr Gln Ala Glu Glu Gln Ser Gly Gly Gly Thr Asp
        35                  40                  45

Ser Lys Pro Arg Leu Thr Ala Thr Val Gln Glu Ser Ser Glu Gln Pro
    50                  55                  60

Val Thr Glu Ala Pro Ala Ala Asp Ser Ser Val Glu Asn Asn Ser Ala
65                  70                  75                  80

Asn Ala Val Lys Ser Ser Glu Thr Ala Glu Ala Ala Glu Val Ser Asp
                85                  90                  95

Gly Gly Arg Ala Ser Gln Thr Glu Ala Val Thr Asn Gln Thr Asn Ser
            100                 105                 110
```

```
Glu Glu His His Pro Ala Glu Lys Ala Thr Ala Val Ser Gly Glu Ala
        115                 120                 125

Gln Ser Val Gln Asn Ala Pro Ser Glu Asn Ala Ala Gln Gln Glu Thr
    130                 135                 140

Ala Lys Thr Glu Pro Ala Thr Ala Ala Glu Asn Asn Asp Ala Ala Pro
145                 150                 155                 160

Thr Asn Ser Phe Phe Glu Lys Asp Gly Lys Trp Tyr Tyr Lys Lys Ala
                165                 170                 175

Asp Gly Gln Leu Ala Thr Gly Trp Gln Thr Ile Asp Gly Lys Gln Leu
            180                 185                 190

Tyr Phe Asn Gln Asp Gly Ser Gln Val Lys Gly Glu Ile His Val Glu
        195                 200                 205

Thr Gly Asp Gln Ile Ile Tyr His Pro Val Phe Ile Ser Asp Ser Pro
    210                 215                 220

Ser Val Leu Glu Val Asn Lys Ile Tyr Tyr Phe Asp Pro Asp Ser Gly
225                 230                 235                 240

Glu Leu Trp Lys Asp Arg Phe Val Tyr Ser Ser Tyr Ala Asp Pro Leu
                245                 250                 255

His Tyr Glu Asn Ile Lys His Glu Gly Trp Phe Tyr Leu Gly Glu Asp
            260                 265                 270

Gly Lys Ala Ala Ile Gly Trp Arg Thr Ile Gly Gly Lys Lys Tyr Tyr
        275                 280                 285

Phe Asp Thr Asn Gly Val Gln Val Lys Gly Lys Leu Ile Ser Thr Asp
    290                 295                 300

Gly Asn Tyr Asn Leu Ile Ser Gln Lys Tyr Gly Lys Lys Ser Phe Leu
305                 310                 315                 320

Asp Pro Asp Thr Gly Glu Ala Trp Thr Asn Arg Phe Val Asn Ala Lys
                325                 330                 335

Tyr Tyr Phe Tyr Asn Phe Ala Gly Tyr Val Ser Thr Thr Asp Trp Phe
            340                 345                 350

Tyr Met Gly Ala Asp Gly Ile Gly Val Thr Asp Trp Gln Lys Ile Asp
        355                 360                 365

Gly Met Asp Tyr Tyr Phe Glu Pro Ser Ser Gly Ile Gln Val Lys Gly
    370                 375                 380

Asp Ile Ala Glu Arg Asp Gly Lys Val Tyr Tyr Leu Asp Glu Asp Ser
385                 390                 395                 400

Gly Gln Val Val Lys Asn Arg Phe Gly Thr Thr Pro Ala Glu Arg Ile
                405                 410                 415

Ser Thr Val Glu Ala Arg Phe Pro Lys Thr Tyr Tyr Phe Gly Ala Asp
            420                 425                 430

Gly Ser Arg Lys Asp Leu Thr Gly Trp Gln Ile Ile Asp Gly Lys Thr
        435                 440                 445

Tyr Tyr Phe Lys Asp Asp His Ser Ile Lys Ala Lys Ser Glu Tyr Ser
    450                 455                 460

Gln Ile Gly Gly Ser Val Pro Asp Asp Gly Phe Ala Glu Ile Asp Gly
465                 470                 475                 480

Asp Gly Tyr Phe Phe Asp Thr Gln Gly Gln Phe Val Thr Asn Arg Phe
                485                 490                 495

Val Arg Lys Tyr Asp Tyr Ser Asn Ile Trp Tyr Tyr Tyr Gly Ser Asp
            500                 505                 510

Gly Lys Arg Val Ser Gly Trp Gln Thr Ile Asp Gly Lys Arg Tyr Tyr
        515                 520                 525

Phe Ser Gln Asp Glu Lys Thr Lys Gly Arg Gln Ile Lys Gly Gln Thr
```

```
    530                 535                 540

Ile Thr Ile Asp Gly Lys Glu Tyr Thr Phe Asp Lys Asp Ser Gly Glu
545                 550                 555                 560

Val Ile Asn Ser Asn
                565


<210> SEQ ID NO 4
<211> LENGTH: 583
<212> TYPE: PRT
<213> ORGANISM: Streptococcus mutans

<400> SEQUENCE: 4

Met Lys Ser Lys Thr Ala Lys Ile Thr Leu Leu Ser Ser Leu Ala Leu
1               5                   10                  15

Ala Ala Phe Gly Ala Thr Asn Val Phe Ala Asp Glu Ala Ser Thr Gln
            20                  25                  30

Leu Asn Ser Asp Thr Val Ala Ala Pro Thr Ala Asp Thr Gln Ala Ser
        35                  40                  45

Glu Pro Ala Ala Thr Glu Lys Glu Gln Ser Pro Val Val Ala Val Val
    50                  55                  60

Glu Ser His Thr Gln Gly Asn Thr Thr Thr Thr Thr Ser Gln Val Thr
65                  70                  75                  80

Ser Lys Glu Leu Glu Asp Ala Lys Ala Asn Ala Asn Gln Glu Gly Leu
                85                  90                  95

Glu Val Thr Glu Thr Glu Ala Gln Lys Gln Pro Ser Val Glu Ala Ala
            100                 105                 110

Asp Ala Asp Asn Lys Ala Gln Ala Gln Thr Ile Asn Thr Ala Val Ala
        115                 120                 125

Asp Tyr Gln Lys Ala Lys Ala Glu Phe Pro Gln Lys Gln Glu Gln Tyr
    130                 135                 140

Asn Lys Asp Phe Glu Lys Tyr Gln Ser Asp Val Lys Glu Tyr Glu Ala
145                 150                 155                 160

Gln Lys Ala Ala Tyr Glu Gln Tyr Lys Lys Glu Val Ala Gln Gly Leu
                165                 170                 175

Ala Ser Gly Arg Val Glu Lys Ala Gln Gly Leu Val Phe Ile Asn Glu
            180                 185                 190

Pro Glu Ala Lys Leu Ser Ile Glu Gly Val Asn Gln Tyr Leu Thr Lys
        195                 200                 205

Glu Ala Arg Gln Lys His Ala Thr Glu Asp Ile Leu Gln Gln Tyr Asn
    210                 215                 220

Thr Asp Asn Tyr Thr Ala Ser Asp Phe Thr Gln Ala Asn Pro Tyr Asp
225                 230                 235                 240

Pro Lys Glu Asp Thr Trp Phe Lys Met Lys Val Gly Asp Gln Ile Ser
                245                 250                 255

Val Thr Tyr Asp Asn Ile Val Asn Ser Lys Tyr Asn Asp Lys Lys Ile
            260                 265                 270

Ser Lys Val Lys Ile Asn Tyr Thr Leu Asn Ser Ser Thr Asn Asn Glu
        275                 280                 285

Gly Ser Ala Leu Val Asn Leu Phe His Asp Pro Thr Lys Thr Ile Phe
    290                 295                 300

Ile Gly Ala Gln Thr Ser Asn Ala Gly Arg Asn Asp Lys Ile Ser Val
305                 310                 315                 320

Thr Met Gln Ile Ile Phe Tyr Asp Glu Asn Gly Asn Glu Ile Asp Leu
                325                 330                 335

Ser Gly Asn Asn Ala Ile Met Ser Leu Ser Ser Leu Asn His Trp Thr
```

```
            340                 345                 350

Thr Lys Tyr Gly Asp His Val Glu Lys Val Asn Leu Gly Asp Asn Glu
        355                 360                 365

Phe Val Lys Ile Pro Gly Ser Ser Val Asp Leu His Gly Asn Glu Ile
    370                 375                 380

Tyr Ser Ala Lys Asp Asn Gln Tyr Lys Ala Asn Gly Ala Thr Phe Asn
385                 390                 395                 400

Gly Asp Gly Ala Asp Gly Trp Asp Ala Val Asn Ala Asp Gly Thr Pro
                405                 410                 415

Arg Ala Ala Thr Ala Tyr Tyr Gly Ala Gly Ala Met Thr Tyr Lys Gly
            420                 425                 430

Glu Pro Phe Thr Phe Thr Val Gly Gly Asn Asp Gln Asn Leu Pro Thr
        435                 440                 445

Thr Ile Trp Phe Ala Thr Asn Ser Ala Val Ala Val Pro Lys Asp Pro
    450                 455                 460

Gly Ala Lys Pro Thr Pro Pro Glu Lys Pro Glu Leu Lys Lys Pro Thr
465                 470                 475                 480

Val Thr Trp His Lys Asn Leu Val Val Glu Thr Lys Thr Glu Glu Val
                485                 490                 495

Pro Pro Val Thr Pro Pro Thr Thr Pro Asp Glu Pro Thr Pro Glu Lys
            500                 505                 510

Pro Lys Thr Pro Glu Asp Pro Gln Ser Pro Val Val Ala Lys Ser Val
        515                 520                 525

Ser Phe Arg Thr Ala Arg Lys Gly Glu Met Arg Val Arg Glu Arg Asp
    530                 535                 540

Tyr Gln Pro Thr Leu Pro His Ala Gly Ala Ala Lys Gln Asn Gly Leu
545                 550                 555                 560

Ala Thr Leu Gly Ala Ile Ser Thr Ala Phe Ala Ala Ala Thr Leu Ile
                565                 570                 575

Ala Ala Arg Lys Lys Glu Asn
            580


<210> SEQ ID NO 5
<211> LENGTH: 1476
<212> TYPE: PRT
<213> ORGANISM: Streptococcus mutans

<400> SEQUENCE: 5

Met Asp Lys Lys Val Arg Tyr Lys Leu Arg Lys Val Lys Lys Arg Trp
1               5                   10                  15

Val Thr Val Ser Val Ala Ser Ala Val Met Thr Leu Thr Thr Leu Ser
            20                  25                  30

Gly Gly Leu Val Lys Ala Asp Ser Asn Glu Ser Lys Ser Gln Ile Ser
        35                  40                  45

Asn Asp Ser Asn Thr Ser Val Val Thr Ala Asn Glu Glu Ser Asn Val
    50                  55                  60

Thr Thr Glu Val Thr Ser Lys Gln Glu Ala Ala Ser Ser Gln Thr Asn
65                  70                  75                  80

His Thr Val Thr Thr Ile Ser Ser Ser Thr Ser Val Val Asn Pro Lys
                85                  90                  95

Glu Val Val Ser Asn Pro Tyr Thr Val Gly Glu Thr Ala Ser Asn Gly
            100                 105                 110

Glu Lys Leu Gln Asn Gln Thr Thr Thr Val Asp Lys Thr Ser Glu Ala
        115                 120                 125

Ala Ala Asn Asn Ile Ser Lys Gln Thr Thr Glu Ala Asp Thr Asp Val
```

```
    130                 135                 140

Ile Asp Asp Ser Asn Ala Ala Asn Leu Gln Ile Leu Glu Lys Leu Pro
145                 150                 155                 160

Asn Val Lys Glu Ile Asp Gly Lys Tyr Tyr Tyr Tyr Asp Asn Asn Gly
                165                 170                 175

Lys Val Arg Thr Asn Phe Thr Leu Ile Ala Asp Gly Lys Ile Leu His
            180                 185                 190

Phe Asp Glu Thr Gly Ala Tyr Thr Asp Thr Ser Ile Asp Thr Val Asn
        195                 200                 205

Lys Asp Ile Val Thr Thr Arg Ser Asn Leu Tyr Lys Lys Tyr Asn Gln
    210                 215                 220

Val Tyr Asp Arg Ser Ala Gln Ser Phe Glu His Val Asp His Tyr Leu
225                 230                 235                 240

Thr Ala Glu Ser Trp Tyr Arg Pro Lys Tyr Ile Leu Lys Asp Gly Lys
                245                 250                 255

Thr Trp Thr Gln Ser Thr Glu Lys Asp Phe Arg Pro Leu Leu Met Thr
            260                 265                 270

Trp Trp Pro Ser Gln Glu Thr Gln Arg Gln Tyr Val Asn Tyr Met Asn
        275                 280                 285

Ala Gln Leu Gly Ile Asn Lys Thr Tyr Asp Asp Thr Ser Asn Gln Leu
    290                 295                 300

Gln Leu Asn Ile Ala Ala Ala Thr Ile Gln Ala Lys Ile Glu Ala Lys
305                 310                 315                 320

Ile Thr Thr Leu Lys Asn Thr Asp Trp Leu Arg Gln Thr Ile Ser Ala
                325                 330                 335

Phe Val Lys Thr Gln Ser Ala Trp Asn Ser Asp Ser Glu Lys Pro Phe
            340                 345                 350

Asp Asp His Leu Gln Asn Gly Ala Val Leu Tyr Asp Asn Glu Gly Lys
        355                 360                 365

Leu Thr Pro Tyr Ala Asn Ser Asn Tyr Arg Ile Leu Asn Arg Thr Pro
    370                 375                 380

Thr Asn Gln Thr Gly Lys Lys Asp Pro Arg Tyr Thr Ala Asp Asn Thr
385                 390                 395                 400

Ile Gly Gly Tyr Glu Phe Leu Leu Ala Asn Asp Val Asp Asn Ser Asn
                405                 410                 415

Pro Val Val Gln Ala Glu Gln Leu Asn Trp Leu His Phe Leu Met Asn
            420                 425                 430

Phe Gly Asn Ile Tyr Ala Asn Asp Pro Asp Ala Asn Phe Asp Ser Ile
        435                 440                 445

Arg Val Asp Ala Val Asp Asn Val Asp Ala Asp Leu Leu Gln Ile Ala
    450                 455                 460

Gly Asp Tyr Leu Lys Ala Ala Lys Gly Ile His Lys Asn Asp Lys Ala
465                 470                 475                 480

Ala Asn Asp His Leu Ser Ile Leu Glu Ala Trp Ser Asp Asn Asp Thr
                485                 490                 495

Pro Tyr Leu His Asp Asp Gly Asp Asn Met Ile Asn Met Asp Asn Lys
            500                 505                 510

Leu Arg Leu Ser Leu Leu Phe Ser Leu Ala Lys Pro Leu Asn Gln Arg
        515                 520                 525

Ser Gly Met Asn Pro Leu Ile Thr Asn Ser Leu Val Asn Arg Thr Asp
    530                 535                 540

Asp Asn Ala Glu Thr Ala Ala Val Pro Ser Tyr Ser Phe Ile Arg Ala
545                 550                 555                 560
```

```
His Asp Ser Glu Val Gln Asp Leu Ile Arg Asp Ile Ile Lys Ala Glu
                565                 570                 575

Ile Asn Pro Asn Val Val Gly Tyr Ser Phe Thr Met Glu Glu Ile Lys
            580                 585                 590

Lys Ala Phe Glu Ile Tyr Asn Lys Asp Leu Leu Ala Thr Glu Lys Lys
        595                 600                 605

Tyr Thr His Tyr Asn Thr Ala Leu Ser Tyr Ala Leu Leu Leu Thr Asn
    610                 615                 620

Lys Ser Ser Val Pro Arg Val Tyr Tyr Gly Asp Met Phe Thr Asp Asp
625                 630                 635                 640

Gly Gln Tyr Met Ala His Lys Thr Ile Asn Tyr Glu Ala Ile Glu Thr
                645                 650                 655

Leu Leu Lys Ala Arg Ile Lys Tyr Val Ser Gly Gly Gln Ala Met Arg
            660                 665                 670

Asn Gln Gln Val Gly Asn Ser Glu Ile Ile Thr Ser Val Arg Tyr Gly
        675                 680                 685

Lys Gly Ala Leu Lys Ala Thr Asp Thr Gly Asp Arg Thr Thr Arg Thr
    690                 695                 700

Ser Gly Val Ala Val Ile Glu Gly Asn Asn Pro Ser Leu Arg Leu Lys
705                 710                 715                 720

Ala Ser Asp Arg Val Val Val Asn Met Gly Ala Ala His Lys Asn Gln
                725                 730                 735

Ala Tyr Arg Pro Leu Leu Leu Thr Thr Asp Asn Gly Ile Lys Ala Tyr
            740                 745                 750

His Ser Asp Gln Glu Ala Ala Gly Leu Val Arg Tyr Thr Asn Asp Arg
        755                 760                 765

Gly Glu Leu Ile Phe Thr Ala Ala Asp Ile Lys Gly Tyr Ala Asn Pro
    770                 775                 780

Gln Val Ser Gly Tyr Leu Gly Val Trp Val Pro Val Gly Ala Ala Ala
785                 790                 795                 800

Asp Gln Asp Val Arg Val Ala Ala Ser Thr Ala Pro Ser Thr Asp Gly
                805                 810                 815

Lys Ser Val His Gln Asn Ala Ala Leu Asp Ser Arg Val Met Phe Glu
            820                 825                 830

Gly Phe Ser Asn Phe Gln Ala Phe Ala Thr Lys Lys Glu Glu Tyr Thr
        835                 840                 845

Asn Val Val Ile Ala Lys Asn Val Asp Lys Phe Ala Glu Trp Gly Val
    850                 855                 860

Thr Asp Phe Glu Met Ala Pro Gln Tyr Val Ser Ser Thr Asp Gly Ser
865                 870                 875                 880

Phe Leu Asp Ser Val Ile Gln Asn Gly Tyr Ala Phe Thr Asp Arg Tyr
                885                 890                 895

Asp Leu Gly Ile Ser Lys Pro Asn Lys Tyr Gly Thr Ala Asp Asp Leu
            900                 905                 910

Val Lys Ala Ile Lys Ala Leu His Ser Lys Gly Ile Lys Val Met Ala
        915                 920                 925

Asp Trp Val Pro Asp Gln Met Tyr Ala Phe Pro Glu Lys Glu Val Val
    930                 935                 940

Thr Ala Thr Arg Val Asp Lys Phe Gly Lys Pro Val Glu Gly Ser Gln
945                 950                 955                 960

Ile Lys Ser Val Leu Tyr Val Ala Asp Ser Lys Ser Ser Gly Lys Asp
                965                 970                 975

Gln Gln Ala Lys Tyr Gly Gly Ala Phe Leu Glu Glu Leu Gln Ala Lys
            980                 985                 990
```

```
Tyr Pro Glu Leu Phe Ala Arg Lys  Gln Ile Ser Thr Gly  Val Pro Met
        995                  1000                  1005

Asp Pro  Ser Val Lys Ile Lys  Gln Trp Ser Ala Lys  Tyr Phe Asn
    1010                 1015                 1020

Gly Thr  Asn Ile Leu Gly Arg  Gly Ala Gly Tyr Val  Leu Lys Asp
    1025                 1030                 1035

Gln Ala  Thr Asn Thr Tyr Phe  Asn Ile Ser Asp Asn  Lys Glu Ile
    1040                 1045                 1050

Asn Phe  Leu Pro Lys Thr Leu  Leu Asn Gln Asp Ser  Gln Val Gly
    1055                 1060                 1065

Phe Ser  Tyr Asp Gly Lys Gly  Tyr Val Tyr Tyr Ser  Thr Ser Gly
    1070                 1075                 1080

Tyr Gln  Ala Lys Asn Thr Phe  Ile Ser Glu Gly Asp  Lys Trp Tyr
    1085                 1090                 1095

Tyr Phe  Asp Asn Asn Gly Tyr  Met Val Thr Gly Ala  Gln Ser Ile
    1100                 1105                 1110

Asn Gly  Val Asn Tyr Tyr Phe  Leu Ser Asn Gly Leu  Gln Leu Arg
    1115                 1120                 1125

Asp Ala  Ile Leu Lys Asn Glu  Asp Gly Thr Tyr Ala  Tyr Tyr Gly
    1130                 1135                 1140

Asn Asp  Gly Arg Arg Tyr Glu  Asn Gly Tyr Tyr Gln  Phe Met Ser
    1145                 1150                 1155

Gly Val  Trp Arg His Phe Asn  Asn Gly Glu Met Ser  Val Gly Leu
    1160                 1165                 1170

Thr Val  Ile Asp Gly Gln Val  Gln Tyr Phe Asp Glu  Met Gly Tyr
    1175                 1180                 1185

Gln Ala  Lys Gly Lys Phe Val  Thr Thr Ala Asp Gly  Lys Ile Arg
    1190                 1195                 1200

Tyr Phe  Asp Lys Gln Ser Gly  Asn Met Tyr Arg Asn  Arg Phe Ile
    1205                 1210                 1215

Glu Asn  Glu Glu Gly Lys Trp  Leu Tyr Leu Gly Glu  Asp Gly Ala
    1220                 1225                 1230

Ala Val  Thr Gly Ser Gln Thr  Ile Asn Gly Gln His  Leu Tyr Phe
    1235                 1240                 1245

Arg Ala  Asn Gly Val Gln Val  Lys Gly Glu Phe Val  Thr Asp Arg
    1250                 1255                 1260

Tyr Gly  Arg Ile Ser Tyr Tyr  Asp Ser Asn Ser Gly  Asp Gln Ile
    1265                 1270                 1275

Arg Asn  Arg Phe Val Arg Asn  Ala Gln Gly Gln Trp  Phe Tyr Phe
    1280                 1285                 1290

Asp Asn  Asn Gly Tyr Ala Val  Thr Gly Ala Arg Thr  Ile Asn Gly
    1295                 1300                 1305

Gln His  Leu Tyr Phe Arg Ala  Asn Gly Val Gln Val  Lys Gly Glu
    1310                 1315                 1320

Phe Val  Thr Asp Arg His Gly  Arg Ile Ser Tyr Tyr  Asp Gly Asn
    1325                 1330                 1335

Ser Gly  Asp Gln Ile Arg Asn  Arg Phe Val Arg Asn  Ala Gln Gly
    1340                 1345                 1350

Gln Trp  Phe Tyr Phe Asp Asn  Asn Gly Tyr Ala Val  Thr Gly Ala
    1355                 1360                 1365

Arg Thr  Ile Asn Gly Gln His  Leu Tyr Phe Arg Ala  Asn Gly Val
    1370                 1375                 1380

Gln Val  Lys Gly Glu Phe Val  Thr Asp Arg Tyr Gly  Arg Ile Ser
```

```
    1385                1390                1395

Tyr Tyr  Asp Ser Asn Ser Gly  Asp Gln Ile Arg Asn  Arg Phe Val
    1400                1405                1410

Arg Asn  Ala Gln Gly Gln Trp  Phe Tyr Phe Asp Asn  Asn Gly Tyr
    1415                1420                1425

Ala Val  Thr Gly Ala Arg Thr  Ile Asn Gly Gln His  Leu Tyr Phe
    1430                1435                1440

Arg Ala  Asn Gly Val Gln Val  Lys Gly Glu Phe Val  Thr Asp Arg
    1445                1450                1455

Tyr Gly  Arg Ile Ser Tyr Tyr  Asp Ala Asn Ser Gly  Glu Arg Val
    1460                1465                1470

Arg Ile  Asn
    1475


<210> SEQ ID NO 6
<211> LENGTH: 1462
<212> TYPE: PRT
<213> ORGANISM: Streptococcus mutans

<400> SEQUENCE: 6

Met Glu Thr Lys Arg Arg Tyr Lys Met Tyr Lys Val Lys Lys His Trp
1               5                   10                  15

Val Thr Ile Ala Val Ala Ser Gly Leu Ile Thr Leu Gly Thr Thr Thr
            20                  25                  30

Leu Gly Ser Ser Val Ser Ala Glu Thr Glu Gln Gln Thr Ser Asp Lys
        35                  40                  45

Val Val Thr Gln Lys Ser Glu Asp Asp Lys Ala Ala Ser Glu Ser Ser
    50                  55                  60

Gln Thr Asp Ala Pro Lys Thr Lys Gln Ala Gln Thr Glu Gln Thr Gln
65                  70                  75                  80

Ala Gln Ser Gln Ala Asn Val Ala Asp Thr Ser Thr Ser Ile Thr Lys
                85                  90                  95

Glu Thr Pro Ser Gln Asn Ile Thr Thr Gln Ala Asn Ser Asp Asp Lys
            100                 105                 110

Thr Val Thr Asn Thr Lys Ser Glu Glu Ala Gln Thr Ser Glu Glu Arg
        115                 120                 125

Thr Lys Gln Ala Glu Glu Ala Gln Ala Thr Ala Ser Ser Gln Ala Leu
    130                 135                 140

Thr Gln Ala Lys Ala Glu Leu Thr Lys Gln Arg Gln Thr Ala Ala Gln
145                 150                 155                 160

Glu Asn Lys Asn Pro Val Asp Leu Ala Ala Ile Pro Asn Val Lys Gln
                165                 170                 175

Ile Asp Gly Lys Tyr Tyr Tyr Ile Gly Ser Asp Gly Gln Pro Lys Lys
            180                 185                 190

Asn Phe Ala Leu Thr Val Asn Asn Lys Val Leu Tyr Phe Asp Lys Asn
        195                 200                 205

Thr Gly Ala Leu Thr Asp Thr Ser Gln Tyr Gln Phe Lys Gln Gly Leu
    210                 215                 220

Thr Lys Leu Asn Asn Asp Tyr Thr Pro His Asn Gln Ile Val Asn Phe
225                 230                 235                 240

Glu Asn Thr Ser Leu Glu Thr Ile Asp Asn Tyr Val Thr Ala Asp Ser
                245                 250                 255

Trp Tyr Arg Pro Lys Asp Ile Leu Lys Asn Gly Lys Thr Trp Thr Ala
            260                 265                 270

Ser Ser Glu Ser Asp Leu Arg Pro Leu Leu Met Ser Trp Trp Pro Asp
```

```
        275                 280                 285

Lys Gln Thr Gln Ile Ala Tyr Leu Asn Tyr Met Asn Gln Gln Gly Leu
    290                 295                 300

Gly Thr Gly Glu Asn Tyr Thr Ala Asp Ser Ser Gln Glu Ser Leu Asn
305                 310                 315                 320

Leu Ala Ala Gln Thr Val Gln Val Lys Ile Glu Thr Lys Ile Ser Gln
                325                 330                 335

Thr Gln Gln Thr Gln Trp Leu Arg Asp Ile Ile Asn Ser Phe Val Lys
            340                 345                 350

Thr Gln Pro Asn Trp Asn Ser Gln Thr Glu Ser Asp Thr Ser Ala Gly
        355                 360                 365

Glu Lys Asp His Leu Gln Gly Gly Ala Leu Leu Tyr Ser Asn Ser Asp
    370                 375                 380

Lys Thr Ala Tyr Ala Asn Ser Asp Tyr Arg Leu Leu Asn Arg Thr Pro
385                 390                 395                 400

Thr Ser Gln Thr Gly Lys Pro Lys Tyr Phe Glu Asp Asn Ser Ser Gly
                405                 410                 415

Gly Tyr Asp Phe Leu Leu Ala Asn Asp Ile Asp Asn Ser Asn Pro Val
            420                 425                 430

Val Gln Ala Glu Gln Leu Asn Trp Leu His Tyr Leu Met Asn Tyr Gly
        435                 440                 445

Ser Ile Val Ala Asn Asp Pro Glu Ala Asn Phe Asp Gly Val Arg Val
    450                 455                 460

Asp Ala Val Asp Asn Val Asn Ala Asp Leu Leu Gln Ile Ala Ser Asp
465                 470                 475                 480

Tyr Leu Lys Ala His Tyr Gly Val Asp Lys Ser Glu Lys Asn Ala Ile
                485                 490                 495

Asn His Leu Ser Ile Leu Glu Ala Trp Ser Asp Asn Asp Pro Gln Tyr
            500                 505                 510

Asn Lys Asp Thr Lys Gly Ala Gln Leu Pro Ile Asp Asn Lys Leu Arg
        515                 520                 525

Leu Ser Leu Leu Tyr Ala Leu Thr Arg Pro Leu Glu Lys Asp Ala Ser
    530                 535                 540

Asn Lys Asn Glu Ile Arg Ser Gly Leu Glu Pro Val Ile Thr Asn Ser
545                 550                 555                 560

Leu Asn Asn Arg Ser Ala Glu Gly Lys Asn Ser Glu Arg Met Ala Asn
                565                 570                 575

Tyr Ile Phe Ile Arg Ala His Asp Ser Glu Val Gln Thr Val Ile Ala
            580                 585                 590

Lys Ile Ile Lys Ala Gln Ile Asn Pro Lys Thr Asp Gly Leu Thr Phe
        595                 600                 605

Thr Leu Asp Glu Leu Lys Gln Ala Phe Lys Ile Tyr Asn Glu Asp Met
    610                 615                 620

Arg Gln Ala Lys Lys Lys Tyr Thr Gln Ser Asn Ile Pro Thr Ala Tyr
625                 630                 635                 640

Ala Leu Met Leu Ser Asn Lys Asp Ser Ile Thr Arg Leu Tyr Tyr Gly
                645                 650                 655

Asp Met Tyr Ser Asp Asp Gly Gln Tyr Met Ala Thr Lys Ser Pro Tyr
            660                 665                 670

Tyr Asp Ala Ile Asp Thr Leu Leu Lys Ala Arg Ile Lys Tyr Ala Ala
        675                 680                 685

Gly Gly Gln Asp Met Lys Ile Thr Tyr Val Glu Gly Asp Lys Ser His
    690                 695                 700
```

```
Met Asp Trp Asp Tyr Thr Gly Val Leu Thr Ser Val Arg Tyr Gly Thr
705                 710                 715                 720

Gly Ala Asn Glu Ala Thr Asp Gln Gly Ser Glu Ala Thr Lys Thr Gln
                725                 730                 735

Gly Met Ala Val Ile Thr Ser Asn Asn Pro Ser Leu Lys Leu Asn Gln
            740                 745                 750

Asn Asp Lys Val Ile Val Asn Met Gly Thr Ala His Lys Asn Gln Glu
        755                 760                 765

Tyr Arg Pro Leu Leu Leu Thr Thr Lys Asp Gly Leu Thr Ser Tyr Thr
    770                 775                 780

Ser Asp Ala Ala Ala Lys Ser Leu Tyr Arg Lys Thr Asn Asp Lys Gly
785                 790                 795                 800

Glu Leu Val Phe Asp Ala Ser Asp Ile Gln Gly Tyr Leu Asn Pro Gln
                805                 810                 815

Val Ser Gly Tyr Leu Ala Val Trp Val Pro Val Gly Ala Ser Asp Asn
            820                 825                 830

Gln Asp Val Arg Val Ala Ala Ser Asn Lys Ala Asn Ala Thr Gly Gln
        835                 840                 845

Val Tyr Glu Ser Ser Ser Ala Leu Asp Ser Gln Leu Ile Tyr Glu Gly
    850                 855                 860

Phe Ser Asn Phe Gln Asp Phe Val Thr Lys Asp Ser Asp Tyr Thr Asn
865                 870                 875                 880

Lys Lys Ile Ala Gln Asn Val Gln Leu Phe Lys Ser Trp Gly Val Thr
                885                 890                 895

Ser Phe Glu Met Ala Pro Gln Tyr Val Ser Ser Glu Asp Gly Ser Phe
            900                 905                 910

Leu Asp Ser Ile Ile Gln Asn Gly Tyr Ala Phe Glu Asp Arg Tyr Asp
        915                 920                 925

Leu Ala Met Ser Lys Asn Asn Lys Tyr Gly Ser Gln Gln Asp Met Ile
    930                 935                 940

Asn Ala Val Lys Ala Leu His Lys Ser Gly Ile Gln Val Ile Ala Asp
945                 950                 955                 960

Trp Val Pro Asp Gln Ile Tyr Asn Leu Pro Gly Lys Glu Val Val Thr
                965                 970                 975

Ala Thr Arg Val Asn Asp Tyr Gly Glu Tyr Arg Lys Asp Ser Glu Ile
            980                 985                 990

Lys Asn Thr Leu Tyr Ala Ala Asn  Thr Lys Ser Asn Gly  Lys Asp Tyr
        995                 1000                1005

Gln Ala  Lys Tyr Gly Gly Ala  Phe Leu Ser Glu Leu  Ala Ala Lys
    1010                1015                1020

Tyr Pro  Ser Ile Phe Asn Arg  Thr Gln Ile Ser Asn  Gly Lys Lys
    1025                1030                1035

Ile Asp  Pro Ser Glu Lys Ile  Thr Ala Trp Lys Ala  Lys Tyr Phe
    1040                1045                1050

Asn Gly  Thr Asn Ile Leu Gly  Arg Gly Val Gly Tyr  Val Leu Lys
    1055                1060                1065

Asp Asn  Ala Ser Asp Lys Tyr  Phe Glu Leu Lys Gly  Asn Gln Thr
    1070                1075                1080

Tyr Leu  Pro Lys Gln Met Thr  Asn Lys Glu Ala Ser  Thr Gly Phe
    1085                1090                1095

Val Asn  Asp Gly Asn Gly Met  Thr Phe Tyr Ser Thr  Ser Gly Tyr
    1100                1105                1110

Gln Ala  Lys Asn Ser Phe Val  Gln Asp Ala Lys Gly  Asn Trp Tyr
    1115                1120                1125
```

```
Tyr Phe  Asp Asn Asn Gly His  Met Val Tyr Gly Leu  Gln His Leu
    1130                 1135                 1140

Asn Gly  Glu Val Gln Tyr Phe  Leu Ser Asn Gly Val  Gln Leu Arg
    1145                 1150                 1155

Glu Ser  Phe Leu Glu Asn Ala  Asp Gly Ser Lys Asn  Tyr Phe Gly
    1160                 1165                 1170

His Leu  Gly Asn Arg Tyr Ser  Asn Gly Tyr Tyr Ser  Phe Asp Asn
    1175                 1180                 1185

Asp Ser  Lys Trp Arg Tyr Phe  Asp Ala Ser Gly Val  Met Ala Val
    1190                 1195                 1200

Gly Leu  Lys Thr Ile Asn Gly  Asn Thr Gln Tyr Phe  Asp Gln Asp
    1205                 1210                 1215

Gly Tyr  Gln Val Lys Gly Ala  Trp Ile Thr Gly Ser  Asp Gly Lys
    1220                 1225                 1230

Lys Arg  Tyr Phe Asp Asp Gly  Ser Gly Asn Met Ala  Val Asn Arg
    1235                 1240                 1245

Phe Ala  Asn Asp Lys Asn Gly  Asp Trp Tyr Tyr Leu  Asn Ser Asp
    1250                 1255                 1260

Gly Ile  Ala Leu Val Gly Val  Gln Thr Ile Asn Gly  Lys Thr Tyr
    1265                 1270                 1275

Tyr Phe  Gly Gln Asp Gly Lys  Gln Ile Lys Gly Lys  Ile Ile Thr
    1280                 1285                 1290

Asp Asn  Gly Lys Leu Lys Tyr  Phe Leu Ala Asn Ser  Gly Glu Leu
    1295                 1300                 1305

Ala Arg  Asn Ile Phe Ala Thr  Asp Ser Gln Asn Asn  Trp Tyr Tyr
    1310                 1315                 1320

Phe Gly  Ser Asp Gly Val Ala  Val Thr Gly Ser Gln  Thr Ile Ala
    1325                 1330                 1335

Gly Lys  Lys Leu Tyr Phe Ala  Ser Asp Gly Lys Gln  Val Lys Gly
    1340                 1345                 1350

Ser Phe  Val Thr Tyr Asn Gly  Lys Val His Tyr Tyr  His Ala Asp
    1355                 1360                 1365

Ser Gly  Glu Leu Gln Val Asn  Arg Phe Glu Ala Asp  Lys Asp Gly
    1370                 1375                 1380

Asn Trp  Tyr Tyr Leu Asp Ser  Asn Gly Glu Ala Leu  Thr Gly Ser
    1385                 1390                 1395

Gln Arg  Ile Asn Gly Gln Arg  Val Phe Phe Thr Arg  Glu Gly Lys
    1400                 1405                 1410

Gln Val  Lys Gly Asp Val Ala  Tyr Asp Glu Arg Gly  Leu Leu Arg
    1415                 1420                 1425

Tyr Tyr  Asp Lys Asn Ser Gly  Asn Met Val Tyr Asn  Lys Val Val
    1430                 1435                 1440

Thr Leu  Ala Asn Gly Arg Arg  Ile Gly Ile Asp Arg  Trp Gly Ile
    1445                 1450                 1455

Ala Arg  Tyr Tyr
    1460


<210> SEQ ID NO 7
<211> LENGTH: 1455
<212> TYPE: PRT
<213> ORGANISM: Streptococcus mutans

<400> SEQUENCE: 7

Met Glu Lys Lys Val Arg Phe Lys Leu Arg Lys Val Lys Lys Arg Trp
1               5                   10                  15
```

```
Val Thr Val Ser Val Ala Ser Ala Val Val Thr Leu Thr Ser Leu Ser
            20                  25                  30

Gly Ser Leu Val Lys Ala Asp Ser Thr Asp Asp Arg Gln Gln Ala Val
        35                  40                  45

Thr Glu Ser Gln Ala Ser Leu Val Thr Thr Ser Glu Ala Ala Lys Glu
    50                  55                  60

Thr Leu Thr Ala Thr Asp Thr Ser Thr Ala Thr Ser Ala Thr Ser Gln
65                  70                  75                  80

Pro Thr Ala Thr Val Thr Asp Asn Val Ser Thr Thr Asn Gln Ser Thr
                85                  90                  95

Asn Thr Thr Ala Asn Thr Ala Asn Phe Asp Val Lys Pro Thr Thr Thr
            100                 105                 110

Ser Glu Gln Ser Lys Thr Asp Asn Ser Asp Lys Ile Ile Ala Thr Ser
        115                 120                 125

Lys Ala Val Asn Arg Leu Thr Ala Thr Gly Lys Phe Val Pro Ala Asn
    130                 135                 140

Asn Asn Thr Ala His Ser Arg Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175

Asp Ile Ala Ala Leu Gly Asn Val Lys Asn Ile Arg Lys Val Asn Gly
            180                 185                 190

Lys Tyr Tyr Tyr Tyr Lys Glu Asp Gly Thr Leu Gln Lys Asn Tyr Ala
        195                 200                 205

Leu Asn Ile Asn Gly Lys Thr Phe Phe Phe Asp Glu Thr Gly Ala Leu
    210                 215                 220

Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Ala
                245                 250                 255

Ala Asn Phe Glu His Val Asp His Tyr Leu Thr Ala Glu Ser Trp Tyr
            260                 265                 270

Arg Pro Lys Tyr Ile Leu Lys Asp Gly Lys Thr Trp Thr Gln Ser Thr
        275                 280                 285

Glu Lys Asp Phe Arg Pro Leu Leu Met Thr Trp Trp Pro Asp Gln Glu
    290                 295                 300

Thr Gln Arg Gln Tyr Val Asn Tyr Met Asn Ala Gln Leu Gly Ile His
305                 310                 315                 320

Gln Thr Tyr Asn Thr Ala Thr Ser Pro Leu Gln Leu Asn Leu Ala Ala
                325                 330                 335

Gln Thr Ile Gln Thr Lys Ile Glu Glu Lys Ile Thr Ala Glu Lys Asn
            340                 345                 350

Thr Asn Trp Leu Arg Gln Thr Ile Ser Ala Phe Val Lys Thr Gln Ser
        355                 360                 365

Ala Trp Asn Ser Asp Ser Glu Lys Pro Phe Asp Asp His Leu Gln Lys
    370                 375                 380

Gly Ala Leu Leu Tyr Ser Asn Asn Ser Lys Leu Thr Ser Gln Ala Asn
385                 390                 395                 400

Ser Asn Tyr Arg Ile Leu Asn Arg Thr Pro Thr Asn Gln Thr Gly Lys
                405                 410                 415

Lys Asp Pro Arg Tyr Thr Ala Asp Arg Thr Ile Gly Gly Tyr Glu Phe
            420                 425                 430

Leu Leu Ala Asn Asp Val Asp Asn Ser Asn Pro Val Val Gln Ala Glu
```

```
        435                 440                 445

Gln Leu Asn Trp Leu His Phe Leu Met Asn Phe Gly Asn Ile Tyr Ala
    450                 455                 460

Asn Asp Pro Asp Ala Asn Phe Asp Ser Ile Arg Val Asp Ala Val Asp
465                 470                 475                 480

Asn Val Asp Ala Asp Leu Leu Gln Ile Ala Gly Asp Tyr Leu Lys Ala
                485                 490                 495

Ala Lys Gly Ile His Lys Asn Asp Lys Ala Ala Asn Asp His Leu Ser
            500                 505                 510

Ile Leu Glu Ala Trp Ser Tyr Asn Asp Thr Pro Tyr Leu His Asp Asp
        515                 520                 525

Gly Asp Asn Met Ile Asn Met Asp Asn Arg Leu Arg Leu Ser Leu Leu
    530                 535                 540

Tyr Ser Leu Ala Lys Pro Leu Asn Gln Arg Ser Gly Met Asn Pro Leu
545                 550                 555                 560

Ile Thr Asn Ser Leu Val Asn Arg Thr Asp Asp Asn Ala Glu Thr Ala
                565                 570                 575

Ala Val Pro Ser Tyr Ser Phe Ile Arg Ala His Asp Ser Glu Val Gln
            580                 585                 590

Asp Leu Ile Arg Asn Ile Ile Arg Ala Glu Ile Asn Pro Asn Val Val
        595                 600                 605

Gly Tyr Ser Phe Thr Met Glu Glu Ile Lys Lys Ala Phe Glu Ile Tyr
    610                 615                 620

Asn Lys Asp Leu Leu Ala Thr Glu Lys Lys Tyr Thr His Tyr Asn Thr
625                 630                 635                 640

Ala Leu Ser Tyr Ala Leu Leu Leu Thr Asn Lys Ser Ser Val Pro Arg
                645                 650                 655

Val Tyr Tyr Gly Asp Met Phe Thr Asp Asp Gly Gln Tyr Met Ala His
            660                 665                 670

Lys Thr Ile Asn Tyr Glu Ala Ile Glu Thr Leu Leu Lys Ala Arg Ile
        675                 680                 685

Lys Tyr Val Ser Gly Gly Gln Ala Met Arg Asn Gln Gln Val Gly Asn
    690                 695                 700

Ser Glu Ile Ile Thr Ser Val Arg Tyr Gly Lys Gly Ala Leu Lys Ala
705                 710                 715                 720

Thr Asp Thr Gly Asp Arg Thr Thr Arg Thr Ser Gly Val Ala Val Ile
                725                 730                 735

Glu Gly Asn Asn Pro Ser Leu Arg Leu Lys Ala Ser Asp Arg Val Val
            740                 745                 750

Val Asn Met Gly Ala Ala His Lys Asn Gln Ala Tyr Arg Pro Leu Leu
        755                 760                 765

Leu Thr Thr Asp Asn Gly Ile Lys Ala Tyr His Ser Asp Gln Glu Ala
    770                 775                 780

Ala Gly Leu Val Arg Tyr Thr Asn Asp Arg Gly Glu Leu Ile Phe Thr
785                 790                 795                 800

Ala Ala Asp Ile Lys Gly Tyr Ala Asn Pro Gln Val Ser Gly Tyr Leu
                805                 810                 815

Gly Val Trp Val Pro Val Gly Ala Ala Ala Asp Gln Asp Val Arg Val
            820                 825                 830

Ala Ala Ser Thr Ala Pro Ser Thr Asp Gly Lys Ser Val His Gln Asn
        835                 840                 845

Ala Ala Leu Asp Ser Arg Val Met Phe Glu Gly Phe Ser Asn Phe Gln
    850                 855                 860
```

```
Ala Phe Ala Thr Lys Lys Glu Glu Tyr Thr Asn Val Val Ile Ala Lys
865                 870                 875                 880

Asn Val Asp Lys Phe Ala Glu Trp Gly Val Thr Asp Phe Glu Met Ala
                885                 890                 895

Pro Gln Tyr Val Ser Ser Thr Asp Gly Ser Phe Leu Asp Ser Val Ile
            900                 905                 910

Gln Asn Gly Tyr Ala Phe Thr Asp Arg Tyr Asp Leu Gly Ile Ser Lys
        915                 920                 925

Pro Asn Lys Tyr Gly Thr Ala Asp Asp Leu Val Lys Ala Ile Lys Ala
    930                 935                 940

Leu His Ser Lys Gly Ile Lys Val Met Ala Asp Trp Val Pro Asp Gln
945                 950                 955                 960

Met Tyr Ala Leu Pro Glu Lys Glu Val Val Thr Ala Thr Arg Val Asp
                965                 970                 975

Lys Tyr Gly Thr Pro Val Ala Gly Ser Gln Ile Lys Asn Thr Leu Tyr
            980                 985                 990

Val Val Asp Gly Lys Ser Ser Gly  Lys Asp Gln Gln Ala  Lys Tyr Gly
        995                 1000                 1005

Gly Ala  Phe Leu Glu Glu Leu  Gln Ala Lys Tyr Pro  Glu Leu Phe
    1010                 1015                 1020

Ala Arg  Lys Gln Ile Ser Thr  Gly Val Pro Met Asp  Pro Ser Val
    1025                 1030                 1035

Lys Ile  Lys Gln Trp Ser Ala  Lys Tyr Phe Asn Gly  Thr Asn Ile
    1040                 1045                 1050

Leu Gly  Arg Gly Ala Gly Tyr  Val Leu Lys Asp Gln  Ala Thr Asn
    1055                 1060                 1065

Thr Tyr  Phe Ser Leu Val Ser  Asp Asn Thr Phe Leu  Pro Lys Ser
    1070                 1075                 1080

Leu Val  Asn Pro Asn His Gly  Thr Ser Ser Ser Val  Thr Gly Leu
    1085                 1090                 1095

Val Phe  Asp Gly Lys Gly Tyr  Val Tyr Tyr Ser Thr  Ser Gly Asn
    1100                 1105                 1110

Gln Ala  Lys Asn Ala Phe Ile  Ser Leu Gly Asn Asn  Trp Tyr Tyr
    1115                 1120                 1125

Phe Asp  Asn Asn Gly Tyr Met  Val Thr Gly Ala Gln  Ser Ile Asn
    1130                 1135                 1140

Gly Ala  Asn Tyr Tyr Phe Leu  Ser Asn Gly Ile Gln  Leu Arg Asn
    1145                 1150                 1155

Ala Ile  Tyr Asp Asn Gly Asn  Lys Val Leu Ser Tyr  Tyr Gly Asn
    1160                 1165                 1170

Asp Gly  Arg Arg Tyr Glu Asn  Gly Tyr Tyr Leu Phe  Gly Gln Gln
    1175                 1180                 1185

Trp Arg  Tyr Phe Gln Asn Gly  Ile Met Ala Val Gly  Leu Thr Arg
    1190                 1195                 1200

Ile His  Gly Ala Val Gln Tyr  Phe Asp Ala Ser Gly  Phe Gln Ala
    1205                 1210                 1215

Lys Gly  Gln Phe Ile Thr Thr  Ala Asp Gly Lys Leu  Arg Tyr Phe
    1220                 1225                 1230

Asp Arg  Asp Ser Gly Asn Gln  Ile Ser Asn Arg Phe  Val Arg Asn
    1235                 1240                 1245

Ser Lys  Gly Glu Trp Phe Leu  Phe Asp His Asn Gly  Val Ala Val
    1250                 1255                 1260

Thr Gly  Thr Val Thr Phe Asn  Gly Gln Arg Leu Tyr  Phe Lys Pro
    1265                 1270                 1275
```

```
Asn Gly  Val Gln Ala Lys Gly  Glu Phe Ile Arg Asp  Ala Asp Gly
    1280                 1285                 1290

His Leu  Arg Tyr Tyr Asp Pro  Asn Ser Gly Asn Glu  Val Arg Asn
    1295                 1300                 1305

Arg Phe  Val Arg Asn Ser Lys  Gly Glu Trp Phe Leu  Phe Asp His
    1310                 1315                 1320

Asn Gly  Ile Ala Val Thr Gly  Thr Arg Val Val Asn  Gly Gln Arg
    1325                 1330                 1335

Leu Tyr  Phe Lys Ser Asn Gly  Val Gln Ala Lys Gly  Glu Leu Ile
    1340                 1345                 1350

Thr Glu  Arg Lys Gly Arg Ile  Lys Tyr Tyr Asp Pro  Asn Ser Gly
    1355                 1360                 1365

Asn Glu  Val Arg Asn Arg Tyr  Val Arg Thr Ser Ser  Gly Asn Trp
    1370                 1375                 1380

Tyr Tyr  Phe Gly Asn Asp Gly  Tyr Ala Leu Ile Gly  Trp His Val
    1385                 1390                 1395

Val Glu  Gly Arg Arg Val Tyr  Phe Asp Glu Asn Gly  Val Tyr Arg
    1400                 1405                 1410

Tyr Ala  Ser His Asp Gln Arg  Asn His Trp Asp Tyr  Asp Tyr Arg
    1415                 1420                 1425

Arg Asp  Phe Gly Arg Gly Ser  Ser Ser Ala Val Arg  Phe Arg His
    1430                 1435                 1440

Ser Arg  Asn Gly Phe Phe Asp  Asn Phe Phe Arg Phe
    1445                 1450                 1455


<210> SEQ ID NO 8
<211> LENGTH: 563
<212> TYPE: PRT
<213> ORGANISM: Streptococcus mutans

<400> SEQUENCE: 8

Met Lys Glu Lys Thr Arg Phe Lys Leu His Lys Val Lys Lys Gln Trp
1               5                   10                  15

Val Ala Ile Ala Val Thr Ser Leu Ala Leu Ala Ala Ile Leu Ser Gly
            20                  25                  30

Ala His Leu Thr Gln Ala Glu Glu Gln Ser Gly Gly Thr Asp Ser Lys
        35                  40                  45

Pro Arg Leu Thr Ala Thr Val Gln Glu Ser Ser Glu Gln Pro Ile Thr
    50                  55                  60

Lys Ala Pro Ala Ala Asp Ser Ser Val Glu Asn Asn Ser Ala Asn Ala
65                  70                  75                  80

Val Lys Ser Ser Glu Thr Ala Glu Ala Ala Glu Val Ser Asp Gly Gly
                85                  90                  95

Arg Ala Ser Gln Thr Glu Ala Val Thr Asn Gln Thr Asn Ser Glu Glu
            100                 105                 110

His His Pro Ala Glu Lys Ala Thr Ala Val Ser Gly Glu Ala Gln Ser
        115                 120                 125

Val Gln Asn Ala Pro Ser Glu Asn Ala Ala Gln Gln Glu Thr Ala Lys
    130                 135                 140

Thr Glu Pro Ala Thr Ala Ala Glu Asn Asn Asp Ala Ala Pro Thr Asn
145                 150                 155                 160

Ser Phe Phe Lys Lys Asp Gly Lys Trp Tyr Tyr Lys Lys Ala Asp Gly
                165                 170                 175

Gln Leu Ala Thr Gly Trp Gln Ile Ile Asp Gly Lys Gln Leu Tyr Phe
            180                 185                 190
```

```
Asn Gln Asp Gly Ser Gln Val Lys Gly Glu Ile His Val Glu Thr Gly
        195                 200                 205

Asp Gln Ile Ile Tyr His Pro Val Phe Ile Ser Asp Ser Pro Ser Val
    210                 215                 220

Leu Glu Val Asn Lys Ile Tyr Tyr Phe Asp Pro Asp Ser Gly Glu Leu
225                 230                 235                 240

Trp Lys Asp Arg Phe Val Tyr Ser Ser Tyr Ala Asp Pro Leu His Tyr
                245                 250                 255

Glu Asn Ile Lys His Glu Gly Trp Phe Tyr Leu Gly Glu Asp Gly Lys
            260                 265                 270

Ala Ala Ile Gly Trp Arg Thr Ile Gly Gly Lys Lys Tyr Tyr Phe Asp
        275                 280                 285

Thr Asn Gly Val Gln Val Lys Gly Lys Leu Ile Ser Thr Asp Gly Asn
    290                 295                 300

Tyr Asn Leu Ile Ser Gln Lys Tyr Gly Lys Lys Ser Phe Leu Asp Pro
305                 310                 315                 320

Asp Thr Gly Glu Ala Trp Thr Asn Arg Phe Val Asn Ala Lys Tyr Tyr
                325                 330                 335

Phe Tyr Asn Phe Ala Gly Tyr Val Ser Thr Thr Asp Trp Phe Tyr Met
            340                 345                 350

Gly Ala Asp Gly Ile Gly Val Thr Asp Trp Gln Lys Ile Asp Gly Met
        355                 360                 365

Asp Tyr Tyr Phe Glu Pro Ser Ser Gly Ile Gln Val Lys Gly Asp Ile
    370                 375                 380

Ala Glu Arg Asp Gly Lys Val Tyr Tyr Leu Asp Glu Asp Ser Gly Gln
385                 390                 395                 400

Val Val Lys Asn Arg Phe Gly Thr Thr Pro Ala Glu Arg Ile Ser Thr
                405                 410                 415

Val Glu Ala Arg Phe Pro Lys Thr Tyr Tyr Phe Gly Ala Asp Gly Ser
            420                 425                 430

Arg Lys Asp Leu Thr Gly Trp Gln Ile Ile Asp Gly Lys Thr Tyr Tyr
        435                 440                 445

Phe Lys Asp Asp His Ser Ile Lys Ala Lys Ser Glu Tyr Ser Gln Ile
    450                 455                 460

Gly Gly Ser Val Pro Asp Asp Gly Phe Ala Glu Ile Asp Gly Asp Gly
465                 470                 475                 480

Tyr Phe Phe Asp Thr Gln Gly Gln Phe Val Thr Asn Arg Phe Val Arg
                485                 490                 495

Lys Tyr Asp Tyr Ser Asn Ile Trp Tyr Tyr Tyr Gly Ser Asp Gly Lys
            500                 505                 510

Arg Val Ser Gly Trp Gln Thr Ile Asp Gly Lys Arg Tyr Tyr Phe Ser
        515                 520                 525

Gln Asp Glu Lys Thr Lys Gly Arg Gln Ile Lys Gly Gln Thr Ile Thr
    530                 535                 540

Ile Asp Gly Lys Glu Tyr Thr Phe Asp Lys Asp Ser Gly Glu Val Ile
545                 550                 555                 560

Asn Ser Asn


<210> SEQ ID NO 9
<211> LENGTH: 454
<212> TYPE: PRT
<213> ORGANISM: Streptococcus mutans

<400> SEQUENCE: 9
```

```
Met Asn Leu Pro Gln Asn Ile Arg Tyr Arg Arg Tyr Gln Asp Trp Thr
1               5                   10                  15

Glu Glu Glu Ile Lys Ser Ile Lys Thr Asn Val Ala Leu Ser Pro Trp
            20                  25                  30

His Thr Thr Tyr His Ile Glu Pro Lys Thr Gly Leu Leu Asn Asp Pro
        35                  40                  45

Asn Gly Phe Ser Tyr Phe Asn Gly Lys Phe Asn Leu Phe Tyr Gln Asn
    50                  55                  60

Trp Pro Phe Gly Ala Ala His Gly Leu Lys Ser Trp Ile His Thr Glu
65                  70                  75                  80

Ser Glu Asp Leu Val His Phe Lys Glu Thr Gly Thr Val Leu Tyr Pro
                85                  90                  95

Asp Thr Ser His Asp Ser His Gly Ala Tyr Ser Gly Ser Ala Tyr Glu
            100                 105                 110

Ile Gly Asp Gln Leu Phe Leu Phe Tyr Thr Gly Asn Val Arg Asp Glu
        115                 120                 125

Asn Trp Val Arg His Pro Leu Gln Ile Gly Ala Phe Met Asp Lys Lys
    130                 135                 140

Gly Asn Ile Gln Lys Phe Thr Asp Val Leu Ile Lys Gln Pro Asn Asp
145                 150                 155                 160

Val Thr Glu His Phe Arg Asp Pro Gln Ile Phe Asn Tyr Lys Gly Gln
                165                 170                 175

Phe Tyr Ala Ile Val Gly Ala Gln Ser Leu Asp Phe Gly Gly Ser Lys
            180                 185                 190

Ser Glu Tyr Met Ile Glu Cys Pro Asn Leu Val Phe Ile Asn Glu Gln
        195                 200                 205

Pro Val Leu Ile Tyr Ser Pro Gln Gly Leu Ser Lys Ser Glu Leu Asp
    210                 215                 220

Tyr His Asn Ile Tyr Pro Asn Thr Tyr Lys Val Cys Gln Ser Phe Asp
225                 230                 235                 240

Thr Glu Lys Pro Ala Leu Val Asp Ala Ser Glu Ile Gln Asn Leu Asp
                245                 250                 255

Phe Gly Phe Glu Cys Tyr Ala Thr Gln Ala Phe Asn Ala Pro Asp Gly
            260                 265                 270

Arg Val Tyr Ala Val Ser Trp Ile Gly Leu Pro Asp Ile Asp Tyr Pro
        275                 280                 285

Ser Asp Ser Tyr Asp Tyr Gln Gly Ala Leu Ser Leu Val Lys Glu Leu
    290                 295                 300

Ser Leu Lys His Gly Lys Leu Tyr Gln Tyr Pro Val Glu Ala Val Arg
305                 310                 315                 320

Ser Leu Arg Ser Glu Lys Glu Ala Val Thr Tyr Lys Pro Glu Thr Asn
                325                 330                 335

Asn Thr Tyr Glu Leu Glu Leu Thr Phe Asp Ser Ser Ser Val Asn Glu
            340                 345                 350

Leu Leu Leu Phe Ala Asp Asn Lys Gly Asn Gly Leu Ala Ile Thr Val
        355                 360                 365

Asp Thr Lys Met Gly Thr Ile Leu Ile Asp Arg Ser Lys Ala Gly Glu
    370                 375                 380

Gln Tyr Ala Leu Glu Phe Gly Ser Gln Arg Ser Cys Ser Ile Gln Ala
385                 390                 395                 400

Lys Glu Thr Val Val Asn Ile Phe Val Asp Lys Ser Ile Phe Glu Ile
                405                 410                 415

Phe Ile Asn Lys Gly Glu Lys Val Phe Thr Gly Arg Val Phe Pro Asn
            420                 425                 430
```

```
Asp Lys Gln Thr Gly Ile Val Ile Lys Ser Gly Lys Pro Ser Gly Asn
        435                 440                 445

Tyr Tyr Glu Leu Lys Tyr
    450


<210> SEQ ID NO 10
<211> LENGTH: 1556
<212> TYPE: PRT
<213> ORGANISM: Streptococcus mutans

<400> SEQUENCE: 10

Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Arg Gln Gly Ser Ala Ser Lys Glu Ala Glu Gln Ser Gln Asn Gln
65                  70                  75                  80

Ala Gly Glu Thr Asn Gly Ser Ile Pro Val Glu Val Pro Lys Thr Asp
                85                  90                  95

Leu Asp Gln Ala Ala Lys Asp Ala Lys Ser Ala Gly Val Asn Val Val
            100                 105                 110

Gln Asp Ala Asp Val Asn Lys Gly Thr Val Lys Thr Ala Glu Glu Ala
        115                 120                 125

Val Gln Lys Glu Thr Glu Ile Lys Glu Asp Tyr Thr Lys Gln Ala Glu
    130                 135                 140

Asp Ile Lys Lys Thr Thr Asp Gln Tyr Lys Ser Asp Val Val Ala His
145                 150                 155                 160

Glu Ala Glu Val Ala Lys Ile Lys Ala Lys Asn Gln Ala Thr Lys Glu
                165                 170                 175

Gln Tyr Glu Lys Asp Met Ala Ala His Lys Ala Glu Val Glu Arg Ile
            180                 185                 190

Asn Ala Ala Asn Ala Ala Ser Lys Thr Ala Tyr Glu Ala Lys Leu Ala
        195                 200                 205

Gln Tyr Gln Ala Asp Leu Ala Ala Val Gln Lys Thr Asn Ala Ala Asn
    210                 215                 220

Gln Ala Ala Tyr Gln Lys Ala Leu Ala Ala Tyr Gln Ala Glu Leu Lys
225                 230                 235                 240

Arg Val Gln Glu Ala Asn Ala Ala Ala Lys Ala Ala Tyr Asp Thr Ala
                245                 250                 255

Val Ala Ala Asn Asn Ala Lys Asn Thr Glu Ile Ala Ala Ala Asn Glu
            260                 265                 270

Glu Ile Arg Lys Arg Met Ala Thr Ala Lys Ala Glu Tyr Glu Thr Lys
        275                 280                 285

Leu Ala Gln Tyr Gln Ala Glu Leu Lys Arg Val Gln Glu Ala Asn Ala
    290                 295                 300

Ala Asn Glu Ala Asp Tyr Gln Ala Lys Leu Thr Ala Tyr Gln Thr Glu
305                 310                 315                 320

Leu Ala Arg Val Gln Lys Ala Asn Ala Asp Ala Lys Ala Ala Tyr Glu
                325                 330                 335

Ala Ala Val Ala Ala Asn Asn Ala Lys Asn Ala Ala Leu Thr Ala Glu
            340                 345                 350
```

```
Asn Thr Ala Ile Lys Gln Arg Asn Glu Asn Ala Lys Ala Thr Tyr Glu
        355                 360                 365

Ala Ala Leu Lys Gln Tyr Glu Ala Asp Leu Ala Ala Val Lys Lys Ala
    370                 375                 380

Asn Ala Ala Asn Glu Ala Asp Tyr Gln Ala Lys Leu Thr Ala Tyr Gln
385                 390                 395                 400

Thr Glu Leu Ala Arg Val Gln Lys Ala Asn Ala Asp Ala Lys Ala Ala
                405                 410                 415

Tyr Glu Ala Ala Val Ala Ala Asn Asn Ala Ala Asn Ala Ala Leu Thr
            420                 425                 430

Ala Glu Asn Thr Ala Ile Lys Lys Arg Asn Ala Asp Ala Lys Ala Asp
        435                 440                 445

Tyr Glu Ala Lys Leu Ala Lys Tyr Gln Ala Asp Leu Ala Lys Tyr Gln
    450                 455                 460

Lys Asp Leu Asp Asp Tyr Pro Val Lys Leu Lys Asp Met Gln Asp Glu
465                 470                 475                 480

Gln Ala Ser Ile Lys Arg Arg Leu Ala Glu Leu Glu Lys His Lys Asn
                485                 490                 495

Glu Asp Gly Asn Leu Thr Glu Pro Ser Ala Gln Asn Leu Val Tyr Asp
            500                 505                 510

Leu Glu Pro Asn Ala Asn Leu Ser Leu Thr Thr Asp Gly Lys Phe Leu
        515                 520                 525

Lys Ala Ser Ala Val Asp Asp Ala Phe Ser Lys Ser Thr Ser Lys Ala
    530                 535                 540

Lys Tyr Val Gln Lys Ile Leu Gln Leu Asp Asp Leu Asp Ile Thr Asn
545                 550                 555                 560

Leu Glu Gln Ser Asn Asp Val Ala Ser Ser Met Glu Leu Tyr Gly Asn
                565                 570                 575

Phe Gly Asp Lys Ala Gly Trp Ser Thr Thr Val Ser Asn Asn Ser Gln
            580                 585                 590

Val Lys Trp Gly Ser Val Leu Leu Glu Arg Gly Gln Ser Ala Thr Ala
        595                 600                 605

Thr Tyr Thr Asn Leu Gln Asn Ser Tyr Tyr Asn Gly Lys Lys Ile Ser
    610                 615                 620

Lys Ile Val Tyr Lys Tyr Thr Val Asp Pro Lys Ser Lys Phe Gln Gly
625                 630                 635                 640

Gln Lys Val Trp Leu Gly Ile Phe Thr Asp Pro Thr Leu Gly Val Phe
                645                 650                 655

Ala Ser Ala Tyr Thr Gly Gln Val Glu Lys Asn Thr Ser Ile Phe Ile
            660                 665                 670

Lys Asn Glu Phe Thr Phe Tyr Asp Glu Asp Gly Lys Pro Ile Asn Phe
        675                 680                 685

Asp Asn Ala Leu Leu Ser Val Ala Ser Leu Asn Arg Glu His Asn Ser
    690                 695                 700

Ile Glu Met Ala Lys Asp Tyr Ser Gly Lys Phe Val Lys Ile Ser Gly
705                 710                 715                 720

Ser Ser Ile Gly Glu Lys Asn Gly Met Ile Tyr Ala Thr Asp Thr Leu
                725                 730                 735

Asn Phe Lys Gln Gly Glu Gly Gly Ser Arg Trp Thr Met Tyr Lys Asn
            740                 745                 750

Ser Gln Ala Gly Ser Gly Trp Asp Ser Ser Asp Ala Pro Asn Ser Trp
        755                 760                 765

Tyr Gly Ala Gly Ala Ile Lys Met Ser Gly Pro Asn Asn His Val Thr
```

```
    770                 775                 780

Val Gly Ala Thr Ser Ala Thr Asn Val Met Pro Val Ser Asp Met Pro
785                 790                 795                 800

Val Val Pro Gly Lys Asp Asn Thr Asp Gly Lys Lys Pro Asn Ile Trp
                805                 810                 815

Tyr Ser Leu Asn Gly Lys Ile Arg Ala Val Asn Val Pro Lys Val Thr
            820                 825                 830

Lys Glu Lys Pro Thr Pro Pro Val Lys Pro Thr Ala Pro Thr Lys Pro
        835                 840                 845

Thr Tyr Glu Thr Glu Lys Pro Leu Lys Pro Ala Pro Val Ala Pro Asn
    850                 855                 860

Tyr Glu Lys Glu Pro Thr Pro Pro Thr Arg Thr Pro Asp Gln Arg Glu
865                 870                 875                 880

Pro Asn Lys Pro Thr Pro Pro Thr Tyr Glu Thr Glu Lys Pro Leu Glu
                885                 890                 895

Pro Ala Pro Val Glu Pro Ser Tyr Glu Ala Glu Pro Thr Pro Pro Thr
            900                 905                 910

Arg Thr Pro Asp Gln Gln Ser Gln Ile Asn Pro His Arg Gln Thr Tyr
        915                 920                 925

Glu Thr Glu Lys Pro Leu Glu Pro Ala Pro Val Glu Pro Ser Tyr Glu
    930                 935                 940

Ala Glu Pro Thr Pro Pro Thr Pro Thr Pro Asp Gln Pro Glu Pro Asn
945                 950                 955                 960

Lys Pro Val Glu Pro Thr Tyr Glu Val Ile Pro Thr Pro Pro Thr Asp
                965                 970                 975

Pro Val Tyr Gln Asp Leu Pro Thr Pro Pro Ser Val Pro Thr Val His
            980                 985                 990

Phe His Tyr Phe Lys Leu Ala Val  Gln Pro Gln Val Asn  Lys Glu Ile
        995                 1000                1005

Arg Asn  Asn Asn Asp Val Asn  Ile Asp Arg Thr Leu  Val Ala Lys
    1010                1015                1020

Gln Ser  Val Val Lys Phe Gln  Leu Lys Thr Ala Asp  Leu Pro Ala
    1025                1030                1035

Gly Arg  Asp Glu Thr Thr Ser  Phe Val Leu Val Asp  Pro Leu Pro
    1040                1045                1050

Ser Gly  Tyr Gln Phe Asn Pro  Glu Ala Thr Lys Ala  Ala Ser Pro
    1055                1060                1065

Gly Phe  Asp Val Thr Tyr Asp  Asn Ala Thr Asn Thr  Val Thr Phe
    1070                1075                1080

Lys Ala  Thr Ala Ala Thr Leu  Ala Thr Phe Asn Ala  Asp Leu Thr
    1085                1090                1095

Lys Ser  Val Ala Thr Val Tyr  Pro Thr Val Val Gly  Gln Val Leu
    1100                1105                1110

Asn Asp  Gly Ala Thr Tyr Lys  Asn Asn Phe Thr Leu  Thr Val Asn
    1115                1120                1125

Asp Ala  Tyr Gly Ile Lys Ser  Asn Val Val Arg Val  Thr Thr Leu
    1130                1135                1140

Val Asn  Gln Met Ile Gln Ile  Thr Gln Ile Ile Ile  Thr Leu Ala
    1145                1150                1155

Thr Lys  Val Ile Lys Met Lys  Met Ala Leu Leu Leu  Met Gly Lys
    1160                1165                1170

Asp Leu  Leu Ala Gly Ser Thr  Asn Tyr Tyr Glu Leu  Thr Trp Asp
    1175                1180                1185
```

```
Leu Asp His Ile Lys Arg Pro Ser Ser Ala Asp Thr Ile Gln Arg
    1190                1195                1200

Ile Tyr Tyr Val Asp Asp Tyr Pro Glu Glu Asp Asp Leu Lys Ile
    1205                1210                1215

Asp Asp Gln Asp Leu Asp Glu Asp Tyr Arg Met Leu Met Val Met
    1220                1225                1230

Lys Leu Leu Val Leu Val Trp Ile Ile Ile Leu Val Leu Lys Gln
    1235                1240                1245

Pro Leu Lys Lys Leu Glu Met Phe Phe Leu Arg Ala Gly Ile Arg
    1250                1255                1260

Leu Lys Gly Ala Phe Gln Ile Phe Arg Ala Asp Asn Pro Arg Glu
    1265                1270                1275

Phe Tyr Asp Thr Tyr Val Lys Thr Gly Ile Asp Leu Lys Ile Val
    1280                1285                1290

Ser Pro Met Val Val Lys Thr Met Gly Gln Thr Gly Gly Ser Tyr
    1295                1300                1305

Glu Asn Gln Ala Tyr Gln Ile Asp Phe Gly Asn Gly Tyr Arg Ser
    1310                1315                1320

Asn Ile Val Ile Asn Lys Trp Leu Pro Lys Ile Asn Pro Lys Lys
    1325                1330                1335

Asp Met Thr Leu Thr Leu Asp Pro Ala Asp Thr Asn Lys Cys Val
    1340                1345                1350

Asp Gly Gln Thr Ile Pro Leu Asn Thr Val Phe Asn Tyr Arg Leu
    1355                1360                1365

Ile Gly Trp His Leu Ser Leu Gln Ile Thr Gln Lys Asn Ser Leu
    1370                1375                1380

Asn Thr Ile Ser Met Met Ile Met Ile Lys Gln Glu Ile Thr Ile
    1385                1390                1395

Leu Val Ser Ile Lys Phe Leu Ala Lys Val Asp Ile Thr Phe Lys
    1400                1405                1410

Asp Gly Ser Ile Ile Lys Ser Gly Ala Glu Leu Thr Gln Tyr Thr
    1415                1420                1425

Thr Ala Glu Val Asp Thr Ala Lys Gly Ala Ile Thr Ile Lys Phe
    1430                1435                1440

Lys Glu Ala Phe Leu Arg Ser Val Ser Ile Asp Ser Ala Phe Gln
    1445                1450                1455

Ala Glu Ser Tyr Ile Gln Met Lys Arg Ile Ala Val Gly Thr Phe
    1460                1465                1470

Glu Asn Thr Tyr Ile Asn Thr Val Asn Gly Val Thr Tyr Ser Ser
    1475                1480                1485

Asn Thr Val Lys Thr Thr Thr Pro Glu Asp Pro Thr Asp Pro Thr
    1490                1495                1500

Asp Pro Gln Asp Pro Ser Ser Pro Arg Thr Ser Thr Val Ile Asn
    1505                1510                1515

Tyr Lys Pro Gln Ser Thr Ala Tyr Gln Pro Ser Ser Val Gln Glu
    1520                1525                1530

Thr Leu Pro Asn Thr Gly Val Thr Asn Gln Cys Leu Tyr Ala Phe
    1535                1540                1545

Thr Trp Tyr Tyr Trp Leu Ser Tyr
    1550                1555
```

<210> SEQ ID NO 11
<211> LENGTH: 445
<212> TYPE: PRT
<213> ORGANISM: Streptococcus mutans

<400> SEQUENCE: 11

```
Met Lys Met Lys Arg Lys Leu Leu Ser Leu Val Ser Val Leu Thr Ile
1               5                   10                  15

Leu Leu Gly Ala Phe Trp Val Thr Lys Ile Val Lys Ala Asp Gln Val
            20                  25                  30

Thr Asn Tyr Thr Asn Thr Ala Ser Ile Thr Lys Ser Asp Gly Thr Ala
        35                  40                  45

Leu Ser Asn Asp Pro Ser Lys Ala Val Asn Tyr Trp Glu Pro Leu Ser
    50                  55                  60

Phe Ser Asn Ser Ile Thr Phe Pro Asp Glu Val Ser Ile Lys Ala Gly
65                  70                  75                  80

Asp Thr Leu Thr Ile Lys Leu Pro Glu Gln Leu Gln Phe Thr Thr Ala
                85                  90                  95

Leu Thr Phe Asp Val Met His Thr Asn Gly Gln Leu Ala Gly Lys Ala
            100                 105                 110

Thr Thr Asp Pro Asn Thr Gly Glu Val Thr Val Thr Phe Thr Asp Ile
        115                 120                 125

Phe Glu Lys Leu Pro Asn Asp Lys Ala Met Thr Leu Asn Phe Asn Ala
    130                 135                 140

Gln Leu Asn His Asn Asn Ile Ser Ile Pro Gly Val Val Asn Phe Asn
145                 150                 155                 160

Tyr Asn Asn Val Ala Tyr Ser Ser Tyr Val Lys Asp Lys Asp Ile Thr
                165                 170                 175

Pro Ile Ser Pro Asp Val Asn Lys Val Gly Tyr Gln Asp Lys Ser Asn
            180                 185                 190

Pro Gly Leu Ile His Trp Lys Val Leu Ile Asn Asn Lys Gln Gly Ala
        195                 200                 205

Ile Asp Asn Leu Thr Leu Thr Asp Val Val Gly Glu Asp Gln Glu Ile
    210                 215                 220

Val Lys Asp Ser Leu Val Ala Ala Arg Leu Gln Tyr Ile Ala Gly Asp
225                 230                 235                 240

Asp Val Asp Ser Leu Asp Glu Ala Ala Ser Arg Pro Tyr Ala Glu Asp
                245                 250                 255

Phe Ser Lys Asn Val Thr Tyr Gln Thr Asn Asp Leu Gly Leu Thr Thr
            260                 265                 270

Gly Phe Thr Tyr Thr Ile Pro Gly Ser Ser Asn Asn Ala Ile Phe Ile
        275                 280                 285

Ser Tyr Thr Thr Arg Leu Thr Ser Ser Gln Ser Ala Gly Lys Asp Val
    290                 295                 300

Ser Asn Thr Ile Ala Ile Ser Gly Asn Asn Ile Asn Tyr Ser Asn Gln
305                 310                 315                 320

Thr Gly Tyr Ala Arg Ile Glu Ser Ala Tyr Gly Arg Ala Ser Ser Arg
                325                 330                 335

Val Lys Arg Gln Ala Glu Thr Thr Thr Val Thr Glu Thr Thr Thr Ser
            340                 345                 350

Glu Ala Thr Thr Glu Thr Ser Ser Thr Thr Asn Asn Asn Ser Thr Thr
        355                 360                 365

Thr Glu Thr Ala Thr Ser Thr Thr Gly Ala Ser Thr Thr Gln Thr Lys
    370                 375                 380

Thr Thr Ala Ser Gln Thr Asn Val Pro Thr Thr Thr Asn Ile Thr Thr
385                 390                 395                 400

Thr Ser Lys Gln Val Thr Lys Gln Lys Ala Lys Phe Val Leu Pro Ser
                405                 410                 415
```

```
Thr Gly Glu Gln Ala Gly Leu Leu Leu Thr Thr Val Gly Leu Val Ile
            420                 425                 430

Val Ala Val Ala Gly Val Tyr Phe Tyr Arg Thr Arg Arg
        435                 440                 445


<210> SEQ ID NO 12
<211> LENGTH: 1561
<212> TYPE: PRT
<213> ORGANISM: Streptococcus mutans

<400> SEQUENCE: 12

Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Gln Ala Glu Gln Ser Gln Thr Lys
65                  70                  75                  80

Leu Glu Arg Gln Met Val His Thr Ile Glu Val Pro Lys Thr Asp Leu
                85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Ala Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Gly Lys Asp Met Val Ala His Lys Ala Glu Val Glu Arg Ile Asn
            180                 185                 190

Ala Ala Asn Ala Ala Ser Lys Thr Ala Tyr Glu Ala Lys Leu Ala Gln
        195                 200                 205

Tyr Gln Ala Asp Leu Ala Ala Val Gln Lys Thr Asn Ala Ala Asn Gln
    210                 215                 220

Ala Ser Tyr Gln Lys Ala Leu Ala Ala Tyr Gln Ala Glu Leu Lys Arg
225                 230                 235                 240

Val Gln Glu Ala Asn Ala Ala Ala Lys Ala Ala Tyr Asp Thr Ala Val
                245                 250                 255

Ala Ala Asn Asn Ala Lys Asn Thr Glu Ile Ala Ala Ala Asn Glu Glu
            260                 265                 270

Ile Arg Lys Arg Asn Ala Thr Ala Lys Ala Glu Tyr Glu Thr Lys Leu
        275                 280                 285

Ala Gln Tyr Gln Ala Glu Leu Lys Arg Val Gln Glu Ala Asn Ala Ala
    290                 295                 300

Asn Glu Ala Asp Tyr Gln Ala Lys Leu Thr Ala Tyr Gln Thr Glu Leu
305                 310                 315                 320

Ala Arg Val Gln Lys Ala Asn Ala Asp Ala Lys Ala Ala Tyr Glu Ala
                325                 330                 335

Ala Val Ala Ala Asn Asn Ala Lys Asn Ala Ala Leu Thr Ala Glu Asn
            340                 345                 350
```

```
Thr Ala Ile Lys Gln Arg Asn Glu Asn Ala Lys Ala Thr Tyr Glu Ala
        355                 360                 365

Ala Leu Lys Gln Tyr Glu Ala Asp Leu Ala Ala Val Lys Lys Ala Asn
    370                 375                 380

Ala Ala Asn Glu Ala Asp Tyr Gln Ala Lys Leu Thr Ala Tyr Gln Thr
385                 390                 395                 400

Glu Leu Ala Arg Val Gln Lys Ala Asn Ala Asp Ala Lys Ala Ala Tyr
                405                 410                 415

Glu Ala Ala Val Ala Ala Asn Asn Ala Ala Asn Ala Ala Leu Thr Ala
            420                 425                 430

Glu Asn Thr Ala Ile Lys Lys Arg Asn Ala Asp Ala Lys Ala Asp Tyr
        435                 440                 445

Glu Ala Lys Leu Ala Lys Tyr Gln Ala Asp Leu Ala Lys Tyr Gln Lys
    450                 455                 460

Asp Leu Ala Asp Tyr Pro Val Lys Leu Lys Ala Tyr Glu Asp Glu Gln
465                 470                 475                 480

Ala Ser Ile Lys Ala Ala Leu Ala Glu Leu Glu Lys His Lys Asn Glu
                485                 490                 495

Asp Gly Asn Leu Thr Glu Pro Ser Ala Gln Asn Leu Val Tyr Asp Leu
            500                 505                 510

Glu Pro Asn Ala Asn Leu Ser Leu Thr Thr Asp Gly Lys Phe Leu Lys
        515                 520                 525

Ala Ser Ala Val Asp Asp Ala Phe Ser Lys Ser Thr Ser Lys Ala Lys
    530                 535                 540

Tyr Asp Gln Lys Ile Leu Gln Leu Asp Asp Leu Asp Ile Thr Asn Leu
545                 550                 555                 560

Glu Gln Ser Asn Asp Val Ala Ser Ser Met Glu Leu Tyr Gly Asn Phe
                565                 570                 575

Gly Asp Lys Ala Gly Trp Ser Thr Thr Val Ser Asn Asn Ser Gln Val
            580                 585                 590

Lys Trp Gly Ser Val Leu Leu Glu Arg Gly Gln Ser Ala Thr Ala Thr
        595                 600                 605

Tyr Thr Asn Leu Gln Asn Ser Tyr Tyr Asn Gly Lys Lys Ile Ser Lys
    610                 615                 620

Ile Val Tyr Lys Tyr Thr Val Asp Pro Lys Ser Lys Phe Gln Gly Gln
625                 630                 635                 640

Lys Val Trp Leu Gly Ile Phe Thr Asp Pro Thr Leu Gly Val Phe Ala
                645                 650                 655

Ser Ala Tyr Thr Gly Gln Val Glu Lys Asn Thr Ser Ile Phe Ile Lys
            660                 665                 670

Asn Glu Phe Thr Phe Tyr Asp Glu Asp Gly Lys Pro Ile Asn Phe Asp
        675                 680                 685

Asn Ala Leu Leu Ser Val Ala Ser Leu Asn Arg Glu Asn Asn Ser Ile
    690                 695                 700

Glu Met Ala Lys Asp Tyr Thr Gly Lys Phe Val Lys Ile Ser Gly Ser
705                 710                 715                 720

Ser Ile Gly Glu Lys Asn Gly Met Ile Tyr Ala Thr Asp Thr Leu Asn
                725                 730                 735

Phe Arg Gln Gly Gln Gly Gly Ala Arg Trp Thr Met Tyr Thr Arg Ala
            740                 745                 750

Ser Glu Pro Gly Ser Gly Trp Asp Ser Ser Asp Ala Pro Asn Ser Trp
        755                 760                 765

Tyr Gly Ala Gly Ala Ile Arg Met Ser Gly Pro Asn Asn Ser Val Thr
```

```
    770                 775                 780

Leu Gly Ala Ile Ser Ser Thr Leu Val Val Pro Ala Asp Pro Thr Met
785                 790                 795                 800

Ala Ile Glu Thr Gly Lys Lys Pro Asn Ile Trp Tyr Ser Leu Asn Gly
                805                 810                 815

Lys Ile Arg Ala Val Asn Leu Pro Lys Val Thr Lys Glu Lys Pro Thr
            820                 825                 830

Pro Pro Val Lys Pro Thr Ala Pro Thr Lys Pro Thr Tyr Glu Thr Glu
        835                 840                 845

Lys Pro Leu Lys Pro Ala Pro Val Ala Pro Asn Tyr Glu Lys Glu Pro
    850                 855                 860

Thr Pro Pro Thr Arg Thr Pro Asp Gln Ala Glu Pro Lys Lys Pro Thr
865                 870                 875                 880

Pro Pro Thr Tyr Glu Thr Glu Lys Pro Leu Glu Pro Ala Pro Val Glu
                885                 890                 895

Pro Ser Tyr Glu Ala Glu Pro Thr Pro Pro Thr Arg Thr Pro Asp Gln
            900                 905                 910

Ala Glu Pro Asn Lys Pro Thr Pro Pro Thr Tyr Glu Thr Glu Lys Pro
        915                 920                 925

Leu Glu Pro Ala Pro Val Glu Pro Ser Tyr Glu Ala Glu Pro Thr Pro
    930                 935                 940

Pro Thr Pro Thr Pro Asp Gln Pro Glu Pro Asn Lys Pro Val Glu Pro
945                 950                 955                 960

Thr Tyr Glu Val Ile Pro Thr Pro Pro Thr Asp Pro Val Tyr Gln Asp
                965                 970                 975

Leu Pro Thr Pro Pro Ser Ile Pro Thr Val His Phe His Tyr Phe Lys
            980                 985                 990

Leu Ala Val Gln Pro Gln Val Asn  Lys Glu Ile Arg Asn  Asn Asn Asp
        995                 1000                1005

Val Asn  Ile Asp Arg Thr Leu  Val Ala Lys Gln Ser  Val Val Lys
    1010                1015                1020

Phe Gln  Leu Lys Thr Ala Asp  Leu Pro Ala Gly Arg  Asp Glu Thr
    1025                1030                1035

Thr Ser  Phe Val Leu Val Asp  Pro Leu Pro Ser Gly  Tyr Gln Phe
    1040                1045                1050

Asn Pro  Glu Ala Thr Lys Ala  Ala Ser Pro Gly Phe  Asp Val Ala
    1055                1060                1065

Tyr Asp  Asn Ala Thr Asn Thr  Val Thr Phe Lys Ala  Thr Ala Ala
    1070                1075                1080

Thr Leu  Ala Thr Phe Asn Ala  Asp Leu Thr Lys Ser  Val Ala Thr
    1085                1090                1095

Ile Tyr  Pro Thr Val Val Gly  Gln Val Leu Asn Asp  Gly Ala Thr
    1100                1105                1110

Tyr Lys  Asn Asn Phe Ser Leu  Thr Val Asn Asp Ala  Tyr Gly Ile
    1115                1120                1125

Lys Ser  Asn Val Val Arg Val  Thr Thr Pro Gly Lys  Pro Asn Asp
    1130                1135                1140

Pro Asp  Asn Pro Asn Asn Asn  Tyr Ile Lys Pro Thr  Lys Val Asn
    1145                1150                1155

Lys Asn  Glu Asn Gly Val Val  Ile Asp Gly Lys Thr  Val Leu Ala
    1160                1165                1170

Gly Ser  Thr Asn Tyr Tyr Glu  Leu Thr Trp Asp Leu  Asp Gln Tyr
    1175                1180                1185
```

```
Lys Asn Asp Arg Ser Ser Ala Asp Thr Ile Gln Gln Gly Phe Tyr
    1190                1195                1200

Tyr Val Asp Asp Tyr Pro Glu Glu Ala Leu Glu Leu Arg Gln Asp
    1205                1210                1215

Leu Val Lys Ile Thr Asp Ala Asn Gly Asn Glu Val Thr Gly Val
    1220                1225                1230

Ser Val Asp Asn Tyr Thr Ser Leu Glu Ala Ala Pro Gln Glu Ile
    1235                1240                1245

Arg Asp Val Leu Ser Lys Ala Gly Ile Arg Pro Lys Gly Ala Phe
    1250                1255                1260

Gln Ile Phe Arg Ala Asp Asn Pro Arg Glu Phe Tyr Asp Thr Tyr
    1265                1270                1275

Val Lys Thr Gly Ile Asp Leu Lys Ile Val Ser Pro Met Val Val
    1280                1285                1290

Lys Lys Gln Met Gly Gln Thr Gly Gly Ser Tyr Glu Asp Gln Ala
    1295                1300                1305

Tyr Gln Ile Asp Phe Gly Asn Gly Tyr Ala Ser Asn Ile Val Ile
    1310                1315                1320

Asn Asn Val Pro Lys Ile Asn Pro Lys Lys Asp Val Thr Leu Thr
    1325                1330                1335

Leu Asp Pro Ala Asp Thr Asn Asn Val Asp Gly Gln Thr Ile Pro
    1340                1345                1350

Leu Asn Thr Val Phe Asn Tyr Arg Leu Ile Gly Gly Ile Ile Pro
    1355                1360                1365

Ala Asn His Ser Glu Glu Leu Phe Glu Tyr Asn Phe Tyr Asp Asp
    1370                1375                1380

Tyr Asp Gln Thr Gly Asp His Tyr Thr Gly Gln Tyr Lys Val Phe
    1385                1390                1395

Ala Lys Val Asp Ile Thr Leu Lys Asn Gly Val Ile Ile Lys Ser
    1400                1405                1410

Gly Thr Glu Leu Thr Gln Tyr Thr Thr Ala Glu Val Asp Thr Thr
    1415                1420                1425

Lys Gly Ala Ile Thr Ile Lys Phe Lys Glu Ala Phe Leu Arg Ser
    1430                1435                1440

Val Ser Ile Asp Ser Ala Phe Gln Ala Glu Ser Tyr Ile Gln Met
    1445                1450                1455

Lys Arg Ile Ala Val Gly Thr Phe Glu Asn Thr Tyr Ile Asn Thr
    1460                1465                1470

Val Asn Gly Val Thr Tyr Ser Ser Asn Thr Val Lys Thr Thr Thr
    1475                1480                1485

Pro Glu Asp Pro Ala Asp Pro Thr Asp Pro Gln Asp Pro Ser Ser
    1490                1495                1500

Pro Arg Thr Ser Thr Val Ile Ile Tyr Lys Pro Gln Ser Thr Ala
    1505                1510                1515

Tyr Gln Pro Ser Ser Val Gln Lys Thr Leu Pro Asn Thr Gly Val
    1520                1525                1530

Thr Asn Asn Ala Tyr Met Pro Leu Leu Gly Ile Ile Gly Leu Val
    1535                1540                1545

Thr Ser Phe Ser Leu Leu Gly Leu Lys Ala Lys Lys Asp
    1550                1555                1560
```

<210> SEQ ID NO 13
<211> LENGTH: 1565
<212> TYPE: PRT
<213> ORGANISM: Streptococcus mutans

<400> SEQUENCE: 13

```
Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Glu Ala Glu Gln Ser Gln Thr Lys
65                  70                  75                  80

Leu Glu Arg Gln Met Val His Thr Ile Glu Val Pro Lys Thr Asp Leu
                85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Pro Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Glu Lys Asp Met Ala Ala His Lys Ala Glu Val Glu Arg Ile Asn
            180                 185                 190

Ala Ala Asn Ala Ala Ser Lys Thr Ala Tyr Glu Ala Lys Leu Ala Gln
        195                 200                 205

Tyr Gln Ala Asp Leu Ala Ala Val Gln Lys Thr Asn Ala Ala Asn Gln
    210                 215                 220

Ala Ala Tyr Gln Lys Ala Leu Ala Ala Tyr Gln Ala Glu Leu Lys Arg
225                 230                 235                 240

Val Gln Glu Ala Asn Ala Ala Ala Lys Ala Ala Tyr Asp Thr Ala Val
                245                 250                 255

Ala Ala Asn Asn Ala Lys Asn Thr Glu Ile Ala Ala Ala Asn Glu Glu
            260                 265                 270

Ile Arg Lys Arg Asn Ala Thr Ala Lys Ala Glu Tyr Glu Thr Lys Leu
        275                 280                 285

Ala Gln Tyr Gln Ala Glu Leu Lys Arg Val Gln Glu Ala Asn Ala Ala
    290                 295                 300

Asn Glu Ala Asp Tyr Gln Ala Lys Leu Thr Ala Tyr Gln Thr Glu Leu
305                 310                 315                 320

Ala Arg Val Gln Lys Ala Asn Ala Asp Ala Lys Ala Thr Tyr Glu Ala
                325                 330                 335

Ala Val Ala Ala Asn Asn Ala Lys Asn Ala Ala Leu Thr Ala Glu Asn
            340                 345                 350

Thr Ala Ile Lys Gln Arg Asn Glu Asn Ala Lys Ala Thr Tyr Glu Ala
        355                 360                 365

Ala Leu Lys Gln Tyr Glu Ala Asp Leu Ala Ala Val Lys Lys Ala Asn
    370                 375                 380

Ala Ala Asn Glu Ala Asp Tyr Gln Ala Lys Leu Thr Ala Tyr Gln Thr
385                 390                 395                 400

Glu Leu Ala Arg Val Gln Lys Ala Asn Ala Asp Ala Lys Ala Ala Tyr
                405                 410                 415
```

```
Glu Ala Ala Val Ala Ala Asn Asn Ala Ala Asn Ala Ala Leu Thr Ala
            420                 425                 430

Glu Asn Thr Ala Ile Lys Lys Arg Asn Ala Asp Ala Lys Ala Asp Tyr
        435                 440                 445

Glu Ala Lys Leu Ala Lys Tyr Gln Ala Asp Leu Ala Lys Tyr Gln Lys
    450                 455                 460

Asp Leu Ala Asp Tyr Pro Val Lys Leu Lys Ala Tyr Glu Asp Glu Gln
465                 470                 475                 480

Thr Ser Ile Lys Ala Ala Leu Ala Glu Leu Glu Lys His Lys Asn Glu
                485                 490                 495

Asp Gly Asn Leu Thr Glu Pro Ser Ala Gln Asn Leu Val Tyr Asp Leu
            500                 505                 510

Glu Pro Asn Ala Asn Leu Ser Leu Thr Thr Asp Gly Lys Phe Leu Lys
        515                 520                 525

Ala Ser Ala Val Asp Asp Ala Phe Ser Lys Ser Thr Ser Lys Ala Lys
    530                 535                 540

Tyr Asp Gln Lys Ile Leu Gln Leu Asp Asp Leu Asp Ile Thr Asn Leu
545                 550                 555                 560

Glu Gln Ser Asn Asp Val Ala Ser Ser Met Glu Leu Tyr Gly Asn Phe
                565                 570                 575

Gly Asp Lys Ala Gly Trp Ser Thr Thr Val Ser Asn Asn Ser Gln Val
            580                 585                 590

Lys Trp Gly Ser Val Leu Leu Glu Arg Gly Gln Ser Ala Thr Ala Thr
        595                 600                 605

Tyr Thr Asn Leu Gln Asn Ser Tyr Tyr Asn Gly Lys Lys Ile Ser Lys
    610                 615                 620

Ile Val Tyr Lys Tyr Thr Val Asp Pro Lys Ser Lys Phe Gln Gly Gln
625                 630                 635                 640

Lys Val Trp Leu Gly Ile Phe Thr Asp Pro Thr Leu Gly Val Phe Ala
                645                 650                 655

Ser Ala Tyr Thr Gly Gln Val Glu Lys Asn Thr Ser Ile Phe Ile Lys
            660                 665                 670

Asn Glu Phe Thr Phe Tyr His Glu Asp Glu Lys Pro Ile Asn Phe Asp
        675                 680                 685

Asn Ala Leu Leu Ser Val Thr Ser Leu Asn Arg Glu His Asn Ser Ile
    690                 695                 700

Glu Met Ala Lys Asp Tyr Ser Gly Lys Phe Val Lys Ile Ser Gly Ser
705                 710                 715                 720

Ser Ile Gly Glu Lys Asn Gly Met Ile Tyr Ala Thr Asp Thr Leu Asn
                725                 730                 735

Phe Lys Gln Gly Glu Gly Gly Ser Arg Trp Thr Met Tyr Lys Asn Ser
            740                 745                 750

Gln Ala Gly Ser Gly Trp Asp Ser Ser Asp Ala Pro Asn Ser Trp Tyr
        755                 760                 765

Gly Ala Gly Ala Ile Lys Met Ser Gly Pro Asn Asn His Val Thr Val
    770                 775                 780

Gly Ala Thr Ser Ala Thr Asn Val Met Pro Val Ser Asp Met Pro Val
785                 790                 795                 800

Val Pro Gly Lys Asp Asn Thr Asp Gly Lys Lys Pro Asn Ile Trp Tyr
                805                 810                 815

Ser Leu Asn Gly Lys Ile Arg Ala Val Asn Val Pro Lys Val Thr Lys
            820                 825                 830

Glu Lys Pro Thr Pro Pro Val Lys Pro Thr Ala Pro Thr Lys Pro Thr
```

-continued

```
        835                 840                 845

Tyr Glu Thr Glu Lys Pro Leu Lys Pro Ala Pro Val Ala Pro Asn Tyr
    850                 855                 860

Glu Lys Glu Pro Thr Pro Pro Thr Arg Thr Pro Asp Gln Ala Glu Pro
865                 870                 875                 880

Asn Lys Pro Thr Pro Pro Thr Tyr Glu Thr Glu Lys Pro Leu Glu Pro
                885                 890                 895

Ala Pro Val Glu Pro Ser Tyr Glu Ala Glu Pro Thr Pro Pro Thr Arg
            900                 905                 910

Thr Pro Asp Gln Ala Glu Pro Asn Lys Pro Thr Pro Pro Thr Tyr Glu
        915                 920                 925

Thr Glu Lys Pro Leu Glu Pro Ala Pro Val Glu Pro Ser Tyr Glu Ala
    930                 935                 940

Glu Pro Thr Pro Pro Thr Pro Thr Pro Asp Gln Pro Glu Pro Asn Lys
945                 950                 955                 960

Pro Val Glu Pro Thr Tyr Glu Val Ile Pro Thr Pro Pro Thr Asp Pro
                965                 970                 975

Val Tyr Gln Asp Leu Pro Thr Pro Pro Ser Asp Pro Thr Val His Phe
            980                 985                 990

His Tyr Phe Lys Leu Ala Val Gln  Pro Gln Val Asn Lys  Glu Ile Arg
        995                 1000                1005

Asn Asn  Asn Asp Ile Asn Ile  Asp Arg Thr Leu Val  Ala Lys Gln
    1010                1015                1020

Ser Val  Val Lys Phe Gln Leu  Lys Thr Ala Asp Leu  Pro Ala Gly
    1025                1030                1035

Arg Asp  Glu Thr Thr Ser Phe  Val Leu Val Asp Pro  Leu Pro Ser
    1040                1045                1050

Gly Tyr  Gln Phe Asn Pro Glu  Ala Thr Lys Ala Ala  Ser Pro Gly
    1055                1060                1065

Phe Asp  Val Thr Tyr Asp Asn  Ala Thr Asn Thr Val  Thr Phe Lys
    1070                1075                1080

Ala Thr  Ala Ala Thr Leu Ala  Thr Phe Asn Ala Asp  Leu Thr Lys
    1085                1090                1095

Ser Val  Ala Thr Ile Tyr Pro  Thr Val Val Gly Gln  Val Leu Asn
    1100                1105                1110

Asp Gly  Ala Thr Tyr Lys Asn  Asn Phe Thr Leu Thr  Val Asn Asp
    1115                1120                1125

Ala Tyr  Gly Ile Lys Ser Asn  Val Val Arg Val Thr  Thr Pro Gly
    1130                1135                1140

Lys Pro  Asn Asp Pro Asp Asn  Pro Asn Asn Asn Tyr  Ile Lys Pro
    1145                1150                1155

Thr Lys  Val Asn Lys Asn Glu  Asn Gly Val Val Ile  Asp Gly Lys
    1160                1165                1170

Thr Val  Leu Ala Gly Ser Thr  Asn Tyr Tyr Glu Leu  Thr Trp Asp
    1175                1180                1185

Leu Asp  Gln Tyr Lys Asn Asp  Arg Ser Ser Ala Asp  Thr Ile Gln
    1190                1195                1200

Lys Gly  Phe Tyr Tyr Val Asp  Asp Tyr Pro Glu Glu  Ala Leu Glu
    1205                1210                1215

Leu Arg  Gln Asp Leu Val Lys  Ile Thr Asp Ala Asn  Gly Asn Glu
    1220                1225                1230

Val Thr  Gly Val Ser Val Asp  Asn Tyr Thr Asn Leu  Glu Ala Ala
    1235                1240                1245
```

```
Pro Gln  Glu Ile Arg Asp Val  Leu Ser Lys Ala Gly  Ile Arg Pro
    1250                 1255                 1260

Lys Gly  Ala Phe Gln Ile Phe  Arg Ala Asp Asn Pro  Arg Glu Phe
    1265                 1270                 1275

Tyr Asp  Thr Tyr Val Lys Thr  Gly Ile Asp Leu Lys  Ile Val Ser
    1280                 1285                 1290

Pro Met  Val Val Lys Lys Gln  Met Gly Gln Thr Gly  Gly Ser Tyr
    1295                 1300                 1305

Glu Asn  Gln Ala Tyr Gln Ile  Asp Phe Gly Asn Gly  Tyr Ala Ser
    1310                 1315                 1320

Asn Ile  Val Ile Asn Asn Val  Pro Lys Ile Asn Pro  Lys Lys Asp
    1325                 1330                 1335

Val Thr  Leu Thr Leu Asp Pro  Ala Asp Thr Asn Asn  Val Asp Gly
    1340                 1345                 1350

Gln Thr  Ile Pro Leu Asn Thr  Val Phe Asn Tyr Arg  Leu Ile Gly
    1355                 1360                 1365

Gly Ile  Ile Pro Ala Asn His  Ser Glu Glu Leu Phe  Glu Tyr Asn
    1370                 1375                 1380

Phe Tyr  Asp Asp Tyr Asp Gln  Thr Gly Asp His Tyr  Thr Gly Gln
    1385                 1390                 1395

Tyr Lys  Val Phe Ala Lys Val  Asp Ile Thr Leu Lys  Asn Gly Val
    1400                 1405                 1410

Ile Ile  Lys Ser Gly Thr Glu  Leu Thr Gln Tyr Thr  Thr Ala Glu
    1415                 1420                 1425

Val Asp  Thr Thr Lys Gly Ala  Ile Thr Ile Lys Phe  Lys Glu Ala
    1430                 1435                 1440

Phe Leu  Arg Ser Val Ser Ile  Asp Ser Ala Phe Gln  Ala Glu Ser
    1445                 1450                 1455

Tyr Ile  Gln Met Lys Arg Ile  Ala Val Gly Thr Phe  Glu Asn Thr
    1460                 1465                 1470

Tyr Ile  Asn Thr Val Asn Gly  Val Thr Tyr Ser Ser  Asn Thr Val
    1475                 1480                 1485

Lys Thr  Thr Thr Pro Glu Asp  Pro Ala Asp Pro Thr  Asp Pro Gln
    1490                 1495                 1500

Asp Pro  Ser Ser Pro Arg Thr  Ser Thr Val Ile Ile  Tyr Lys Pro
    1505                 1510                 1515

Gln Ser  Thr Ala Tyr Gln Pro  Ser Ser Val Gln Glu  Thr Leu Pro
    1520                 1525                 1530

Asn Thr  Gly Val Thr Asn Asn  Ala Tyr Met Pro Leu  Leu Gly Ile
    1535                 1540                 1545

Ile Gly  Leu Val Thr Ser Phe  Ser Leu Leu Gly Leu  Lys Ala Lys
    1550                 1555                 1560

Lys Asp
    1565


<210> SEQ ID NO 14
<211> LENGTH: 67
<212> TYPE: PRT
<213> ORGANISM: Streptococcus mutans

<400> SEQUENCE: 14

Met Asp Thr Gln Ala Phe Glu Gln Phe Asp Val Met Asp Ser Gln Thr
1               5                   10                  15

Leu Ser Thr Val Glu Gly Gly Lys Val Ser Gly Gly Glu Ala Val Ala
            20                  25                  30
```

```
Ala Ile Gly Ile Cys Ala Thr Ala Ser Ala Ala Ile Gly Gly Leu Ala
        35                  40                  45

Gly Ala Thr Leu Val Thr Pro Tyr Cys Val Gly Thr Trp Gly Leu Ile
    50                  55                  60

Arg Ser His
65


<210> SEQ ID NO 15
<211> LENGTH: 71
<212> TYPE: PRT
<213> ORGANISM: Streptococcus mutans

<400> SEQUENCE: 15

Met Glu Leu Asn Val Asn Asn Tyr Lys Ser Leu Thr Asn Asp Glu Leu
1               5                   10                  15

Ser Glu Val Phe Gly Gly Asp Lys Gln Ala Ala Asp Thr Phe Leu Ser
            20                  25                  30

Ala Val Gly Gly Ala Ala Ser Gly Phe Thr Tyr Cys Ala Ser Asn Gly
        35                  40                  45

Val Trp His Pro Tyr Ile Leu Ala Gly Cys Ala Gly Val Gly Ala Val
    50                  55                  60

Gly Ser Val Val Phe Pro His
65                  70


<210> SEQ ID NO 16
<211> LENGTH: 1590
<212> TYPE: PRT
<213> ORGANISM: Streptococcus sobrinus

<400> SEQUENCE: 16

Met Glu Lys Asn Val Arg Phe Lys Met His Lys Val Lys Lys Arg Trp
1               5                   10                  15

Val Thr Leu Ser Val Ala Ser Ala Thr Met Leu Ala Ser Ala Leu Gly
            20                  25                  30

Ala Ser Val Ala Ser Ala Asp Thr Asp Thr Ala Ser Asp Asp Ser Asn
        35                  40                  45

Gln Ala Val Val Thr Gly Asp Gln Thr Thr Asn Asn Gln Ala Thr Asp
    50                  55                  60

Gln Thr Ser Ile Ala Ala Thr Ala Thr Ser Glu Gln Ser Ala Ser Thr
65                  70                  75                  80

Asp Ala Ala Thr Asp Gln Ala Ser Ala Ala Glu Gln Thr Gln Gly Thr
                85                  90                  95

Thr Ala Ser Thr Asp Thr Ala Ala Gln Thr Thr Thr Asn Ala Asn Glu
            100                 105                 110

Ala Lys Trp Val Pro Thr Glu Asn Glu Asn Gln Gly Phe Thr Asp Glu
        115                 120                 125

Met Leu Ala Glu Ala Lys Asn Val Ala Thr Ala Glu Ser Asp Ser Ile
    130                 135                 140

Pro Ser Asp Leu Ala Lys Met Ser Asn Val Lys Gln Val Asp Gly Lys
145                 150                 155                 160

Tyr Tyr Tyr Tyr Asp Gln Asp Gly Asn Val Lys Lys Asn Phe Ala Val
                165                 170                 175

Ser Val Gly Asp Lys Ile Tyr Tyr Phe Asp Glu Thr Gly Ala Tyr Lys
            180                 185                 190

Asp Thr Ser Lys Val Asp Ala Asp Lys Ser Ser Ser Ala Val Ser Gln
        195                 200                 205

Asn Ala Thr Ile Phe Ala Ala Asn Asn Arg Ala Tyr Ser Thr Ser Ala
```

-continued

```
    210                 215                 220

Lys Asn Phe Glu Ala Val Asp Asn Tyr Leu Thr Ala Asp Ser Trp Tyr
225                 230                 235                 240

Arg Pro Lys Ser Ile Leu Lys Asp Gly Lys Thr Trp Thr Glu Ser Gly
                245                 250                 255

Lys Asp Asp Phe Arg Pro Leu Leu Met Ala Trp Trp Pro Asp Thr Glu
            260                 265                 270

Thr Lys Arg Asn Tyr Val Asn Tyr Met Asn Lys Val Val Gly Ile Asp
        275                 280                 285

Lys Thr Tyr Thr Ala Glu Thr Ser Gln Ala Asp Leu Thr Ala Ala Ala
    290                 295                 300

Glu Leu Val Gln Ala Arg Ile Glu Gln Lys Ile Thr Ser Glu Asn Asn
305                 310                 315                 320

Thr Lys Trp Leu Arg Glu Ala Ile Ser Ala Phe Val Lys Thr Gln Pro
                325                 330                 335

Gln Trp Asn Gly Glu Ser Glu Lys Pro Tyr Asp Asp His Leu Gln Asn
            340                 345                 350

Gly Ala Leu Leu Phe Asp Asn Gln Thr Asp Leu Thr Pro Asp Thr Gln
        355                 360                 365

Ser Asn Tyr Arg Leu Leu Asn Arg Thr Pro Thr Asn Gln Thr Gly Ser
    370                 375                 380

Leu Asp Ser Arg Phe Thr Tyr Asn Pro Asn Asp Pro Leu Gly Gly Tyr
385                 390                 395                 400

Asp Phe Leu Leu Ala Asn Asp Val Asp Asn Ser Asn Pro Val Val Gln
                405                 410                 415

Ala Glu Gln Leu Asn Trp Leu His Tyr Leu Leu Asn Phe Gly Ser Ile
            420                 425                 430

Tyr Ala Asn Asp Ala Asp Ala Asn Phe Asp Ser Ile Arg Val Asp Ala
        435                 440                 445

Val Asp Asn Val Asp Ala Asp Leu Leu Gln Ile Ser Ser Asp Tyr Leu
    450                 455                 460

Lys Ala Ala Tyr Gly Ile Asp Lys Asn Asn Lys Asn Ala Asn Asn His
465                 470                 475                 480

Val Ser Ile Val Glu Ala Trp Ser Asp Asn Asp Thr Pro Tyr Leu His
                485                 490                 495

Asp Asp Gly Asp Asn Leu Met Asn Met Asp Asn Lys Phe Arg Leu Ser
            500                 505                 510

Met Leu Trp Ser Leu Ala Lys Pro Leu Asp Lys Arg Ser Gly Leu Asn
        515                 520                 525

Pro Leu Ile His Asn Ser Leu Val Asp Arg Glu Val Asp Asp Arg Glu
    530                 535                 540

Val Glu Thr Val Pro Ser Tyr Ser Phe Ala Arg Ala His Asp Ser Glu
545                 550                 555                 560

Val Gln Asp Ile Ile Arg Asp Ile Ile Lys Ala Glu Ile Asn Pro Asn
                565                 570                 575

Ser Phe Gly Tyr Ser Phe Thr Gln Glu Glu Ile Glu Gln Ala Phe Lys
            580                 585                 590

Ile Tyr Asn Glu Asp Leu Lys Lys Thr Asp Lys Lys Tyr Thr His Tyr
        595                 600                 605

Asn Val Pro Leu Ser Tyr Thr Leu Leu Leu Thr Asn Lys Gly Ser Ile
    610                 615                 620

Pro Arg Val Tyr Tyr Gly Asp Met Phe Thr Asp Asp Gly Gln Tyr Met
625                 630                 635                 640
```

```
Ala Asn Lys Thr Val Asn Tyr Asp Ala Ile Glu Ser Leu Leu Lys Ala
                645                 650                 655

Arg Met Lys Tyr Val Ser Gly Gly Gln Ala Met Gln Asn Tyr Gln Ile
            660                 665                 670

Gly Asn Gly Glu Ile Leu Thr Ser Val Arg Tyr Gly Lys Gly Ala Leu
        675                 680                 685

Lys Gln Ser Asp Lys Gly Asp Ala Thr Thr Arg Thr Ser Gly Val Gly
    690                 695                 700

Val Val Met Gly Asn Gln Pro Asn Phe Ser Leu Asp Gly Lys Val Val
705                 710                 715                 720

Ala Leu Asn Met Gly Ala Ala His Ala Asn Gln Glu Tyr Arg Ala Leu
                725                 730                 735

Met Val Ser Thr Lys Asp Gly Val Ala Thr Tyr Ala Thr Asp Ala Asp
            740                 745                 750

Ala Ser Lys Ala Gly Leu Val Lys Arg Thr Asp Glu Asn Gly Tyr Leu
        755                 760                 765

Tyr Phe Leu Asn Asp Asp Leu Lys Gly Val Ala Asn Pro Gln Val Ser
    770                 775                 780

Gly Phe Leu Gln Val Trp Val Pro Val Gly Ala Ala Asp Asp Gln Asp
785                 790                 795                 800

Ile Arg Val Ala Ala Ser Asp Thr Ala Ser Thr Asp Gly Lys Ser Leu
                805                 810                 815

His Gln Asp Ala Ala Met Asp Ser Arg Val Met Phe Glu Gly Phe Ser
            820                 825                 830

Asn Phe Gln Ser Phe Ala Thr Lys Glu Glu Glu Tyr Thr Asn Val Val
        835                 840                 845

Ile Ala Asn Asn Val Asp Lys Phe Val Ser Trp Gly Ile Thr Asp Phe
    850                 855                 860

Glu Met Ala Pro Gln Tyr Val Ser Ser Thr Asp Gly Gln Phe Leu Asp
865                 870                 875                 880

Ser Val Ile Gln Asn Gly Tyr Ala Phe Thr Asp Arg Tyr Asp Leu Gly
                885                 890                 895

Met Ser Lys Ala Asn Lys Tyr Gly Thr Ala Asp Gln Leu Val Lys Ala
            900                 905                 910

Ile Lys Ala Leu His Ala Lys Gly Leu Lys Val Met Ala Asp Trp Val
        915                 920                 925

Pro Asp Gln Met Tyr Thr Phe Pro Lys Gln Glu Val Val Thr Val Thr
    930                 935                 940

Arg Thr Asp Lys Phe Gly Lys Pro Ile Ala Gly Ser Gln Ile Asn His
945                 950                 955                 960

Ser Leu Tyr Val Thr Asp Thr Lys Ser Ser Gly Asp Asp Tyr Gln Ala
                965                 970                 975

Lys Tyr Gly Gly Ala Phe Leu Asp Glu Leu Lys Glu Lys Tyr Pro Glu
            980                 985                 990

Leu Phe Thr Lys Lys Gln Ile Ser  Thr Gly Gln Ala Ile  Asp Pro Ser
        995                 1000                1005

Val Lys  Ile Lys Gln Trp Ser  Ala Lys Tyr Phe Asn  Gly Ser Asn
    1010                1015                1020

Ile Leu  Gly Arg Gly Ala Asp  Tyr Val Leu Ser Asp  Gln Val Ser
    1025                1030                1035

Asn Lys  Tyr Phe Asn Val Ala  Ser Asp Thr Leu Phe  Leu Pro Ser
    1040                1045                1050

Ser Leu  Leu Gly Lys Val Val  Glu Ser Gly Ile Arg  Tyr Asp Gly
    1055                1060                1065
```

```
Lys Gly  Tyr Ile Tyr Asn Ser  Ser Ala Thr Gly Asp  Gln Val Lys
    1070                 1075                 1080

Ala Ser  Phe Ile Thr Glu Ala  Gly Asn Leu Tyr Tyr  Phe Gly Lys
    1085                 1090                 1095

Asp Gly  Tyr Met Val Thr Gly  Ala Gln Thr Ile Asn  Gly Ala Asn
    1100                 1105                 1110

Tyr Phe  Phe Leu Glu Asn Gly  Thr Ala Leu Arg Asn  Thr Ile Tyr
    1115                 1120                 1125

Thr Asp  Ala Gln Gly Asn Ser  His Tyr Tyr Ala Asn  Asp Gly Lys
    1130                 1135                 1140

Arg Tyr  Glu Asn Gly Tyr Gln  Gln Phe Gly Asn Asp  Trp Arg Tyr
    1145                 1150                 1155

Phe Lys  Asp Gly Asn Met Ala  Val Gly Leu Thr Thr  Val Asp Gly
    1160                 1165                 1170

Asn Val  Gln Tyr Phe Asp Lys  Asp Gly Val Gln Ala  Lys Asp Lys
    1175                 1180                 1185

Ile Ile  Val Thr Arg Asp Gly  Lys Val Arg Tyr Phe  Asp Gln His
    1190                 1195                 1200

Asn Gly  Asn Ala Ala Thr Asn  Thr Phe Ile Ala Asp  Lys Thr Gly
    1205                 1210                 1215

His Trp  Tyr Tyr Leu Gly Lys  Asp Gly Val Ala Val  Thr Gly Ala
    1220                 1225                 1230

Gln Thr  Val Gly Lys Gln Lys  Leu Tyr Phe Glu Ala  Asn Gly Gln
    1235                 1240                 1245

Gln Val  Lys Gly Asp Phe Val  Thr Ser Asp Glu Gly  Lys Leu Tyr
    1250                 1255                 1260

Phe Tyr  Asp Val Asp Ser Gly  Asp Met Trp Thr Asp  Thr Phe Ile
    1265                 1270                 1275

Glu Asp  Lys Ala Gly Asn Trp  Phe Tyr Leu Gly Lys  Asp Gly Ala
    1280                 1285                 1290

Ala Val  Thr Gly Ala Gln Thr  Ile Arg Gly Gln Lys  Leu Tyr Phe
    1295                 1300                 1305

Lys Ala  Asn Gly Gln Gln Val  Lys Gly Asp Ile Val  Lys Gly Thr
    1310                 1315                 1320

Asp Gly  Lys Ile Arg Tyr Tyr  Asp Ala Lys Ser Gly  Glu Gln Val
    1325                 1330                 1335

Phe Asn  Lys Thr Val Lys Ala  Ala Asp Gly Lys Thr  Tyr Val Ile
    1340                 1345                 1350

Gly Asn  Asp Gly Val Ala Val  Asp Pro Ser Val Val  Lys Gly Gln
    1355                 1360                 1365

Thr Phe  Lys Asp Ala Ser Gly  Ala Leu Arg Phe Tyr  Asn Leu Lys
    1370                 1375                 1380

Gly Gln  Leu Val Thr Gly Ser  Gly Trp Tyr Glu Thr  Ala Asn His
    1385                 1390                 1395

Asp Trp  Val Tyr Ile Gln Ser  Gly Lys Ala Leu Thr  Gly Glu Gln
    1400                 1405                 1410

Thr Ile  Asn Gly Gln His Leu  Tyr Phe Lys Glu Asp  Gly His Gln
    1415                 1420                 1425

Val Lys  Gly Gln Leu Val Thr  Gly Thr Asp Gly Lys  Val Arg Tyr
    1430                 1435                 1440

Tyr Asp  Ala Asn Ser Gly Asp  Gln Ala Phe Asn Lys  Ser Val Thr
    1445                 1450                 1455

Val Asn  Gly Lys Thr Tyr Tyr  Phe Gly Asn Asp Gly  Thr Ala Gln
```

```
    1460                1465                1470

Thr Ala  Gly Asn Pro Lys Gly  Gln Thr Phe Lys Asp  Gly Ser Asp
    1475                1480                1485

Ile Arg  Phe Tyr Ser Met Glu  Gly Gln Leu Val Thr  Gly Ser Gly
    1490                1495                1500

Trp Tyr  Glu Asn Ala Gln Gly  Gln Trp Leu Tyr Val  Lys Asn Gly
    1505                1510                1515

Lys Val  Leu Thr Gly Leu Gln  Thr Val Gly Ser Gln  Arg Val Tyr
    1520                1525                1530

Phe Asp  Glu Asn Gly Ile Gln  Ala Lys Gly Lys Ala  Val Arg Thr
    1535                1540                1545

Ser Asp  Gly Lys Ile Arg Tyr  Phe Asp Glu Asn Ser  Gly Ser Met
    1550                1555                1560

Ile Thr  Asn Gln Trp Lys Phe  Val Tyr Gly Gln Tyr  Tyr Tyr Phe
    1565                1570                1575

Gly Asn  Asp Gly Ala Arg Ile  Tyr Arg Gly Trp Asn
    1580                1585                1590


<210> SEQ ID NO 17
<211> LENGTH: 1554
<212> TYPE: PRT
<213> ORGANISM: Streptococcus sobrinus

<400> SEQUENCE: 17

Met Glu Lys Lys Leu His Tyr Lys Leu His Lys Val Lys Lys His Trp
1               5                   10                  15

Val Thr Ile Ala Val Ala Ser Ile Gly Leu Val Ser Leu Val Gly Ala
            20                  25                  30

Gly Thr Val Ser Ala Glu Asp Lys Val Ala Asn Asp Thr Thr Ala Gln
        35                  40                  45

Ala Thr Val Gly Val Asp Thr Gly Gln Asp Gln Ala Thr Thr Asn Asp
    50                  55                  60

Ala Asn Thr Asn Thr Thr Asp Thr Asp Thr Ala Asp Gln Ser Ala Asn
65                  70                  75                  80

Thr Asn Gln Asp Gln Ala Gly Ser Asp Gln Ser Asn Asn Gln Asp Gln
                85                  90                  95

Ala Lys Gln Asp Thr Ala Asn Thr Asp Arg Asn Gln Ala Asp Asn Ser
            100                 105                 110

Gln Thr Asp Asn Asn Gln Ala Thr Asp Gln Ala Thr Ser Pro Ala Thr
        115                 120                 125

Asp Gly Thr Ser Val Gln Arg Arg Asp Ala Ala Asn Val Ala Thr Ala
    130                 135                 140

Ala Asp Gln Glu Gly Gln Thr Ala Pro Ser Glu Gln Glu Lys Ser Ala
145                 150                 155                 160

Ala Leu Ser Leu Asp Asn Val Lys Leu Ile Asp Gly Lys Tyr Tyr Tyr
                165                 170                 175

Val Gln Ala Asp Gly Ser Tyr Lys Lys Asn Phe Ala Ile Thr Val Asn
            180                 185                 190

Gly Gln Met Leu Tyr Phe Asp Ser Asp Thr Gly Ala Leu Ser Ser Thr
        195                 200                 205

Ser Thr Tyr Ser Phe Ser Gln Gly Thr Thr Asn Leu Val Asp Asp Phe
    210                 215                 220

Ser Ser His Asn Lys Ala Tyr Asp Ser Thr Ala Lys Ser Phe Glu Leu
225                 230                 235                 240

Val Asn Gly Tyr Leu Thr Ala Asn Ser Trp Tyr Arg Pro Ala Gly Ile
```

```
                245                 250                 255

Leu Arg Asn Gly Gln Thr Trp Glu Ala Ser Asn Glu Asn Asp Leu Arg
            260                 265                 270

Pro Val Leu Met Ser Trp Trp Pro Asp Lys Asp Thr Gln Val Ala Tyr
        275                 280                 285

Val Asn Tyr Met Asn Lys Tyr Leu Ser Ala Asn Glu Thr Glu Val Thr
    290                 295                 300

Asn Glu Thr Ser Gln Val Asp Leu Asn Lys Glu Ala Gln Ser Ile Gln
305                 310                 315                 320

Thr Lys Ile Glu Gln Lys Ile Thr Ser Asp Asn Ser Thr Gln Trp Leu
                325                 330                 335

Arg Thr Ala Met Glu Ala Phe Val Ala Ala Gln Pro Lys Trp Asn Met
            340                 345                 350

Ser Thr Glu Asn Phe Asn Lys Gly Asp His Leu Gln Gly Gly Ala Leu
        355                 360                 365

Leu Tyr Thr Asn Ser Asp Leu Thr Pro Trp Ala Asn Ser Asp Tyr Arg
    370                 375                 380

Leu Leu Asn Arg Thr Pro Thr Gln Gln Asp Gly Thr Lys Lys Tyr Phe
385                 390                 395                 400

Thr Glu Gly Gly Glu Gly Gly Tyr Glu Phe Leu Leu Ser Asn Asp Val
                405                 410                 415

Asp Asn Ser Asn Pro Val Val Gln Ala Glu Gln Leu Asn Gln Leu His
            420                 425                 430

Tyr Leu Met Asn Trp Gly Asp Ile Val Met Gly Asp Lys Asp Ala Asn
        435                 440                 445

Phe Asp Gly Val Arg Val Asp Ala Val Asp Asn Val Asn Ala Asp Leu
    450                 455                 460

Leu Gln Val Tyr Ser Asn Tyr Phe Lys Asp Asn Tyr Lys Val Thr Asp
465                 470                 475                 480

Ser Glu Ala Asn Ala Leu Ala His Ile Ser Ile Leu Glu Ala Trp Ser
                485                 490                 495

Leu Asn Asp Asn Gln Tyr Asn Glu Asp Thr Asn Gly Thr Ala Leu Ser
            500                 505                 510

Ile Asp Asn Ser Ser Arg Leu Thr Ser Leu Ala Val Leu Thr Lys Gln
        515                 520                 525

Pro Gly Gln Arg Ile Asp Leu Ser Asn Leu Ile Ser Glu Ser Val Asn
    530                 535                 540

Lys Glu Arg Ala Asn Asp Thr Ala Tyr Gly Asp Thr Ile Pro Thr Tyr
545                 550                 555                 560

Ser Phe Val Arg Ala His Asp Ser Glu Val Gln Thr Val Ile Ala Lys
                565                 570                 575

Ile Val Lys Glu Lys Ile Asp Thr Asn Ser Asp Gly Tyr Thr Phe Thr
            580                 585                 590

Leu Asp Gln Leu Lys Asp Ala Phe Lys Ile Tyr Asn Glu Asp Met Ala
        595                 600                 605

Lys Val Asn Lys Thr Tyr Thr His Tyr Asn Ile Pro Ala Ala Tyr Ala
    610                 615                 620

Leu Leu Leu Ser Asn Met Glu Ser Val Pro Arg Val Tyr Tyr Gly Asp
625                 630                 635                 640

Leu Tyr Thr Asp Asp Gly Gln Tyr Met Ala Lys Lys Ser Pro Tyr Tyr
                645                 650                 655

Asp Ala Ile Ala Thr Met Leu Gln Gly Arg Ile Ala Tyr Val Ser Gly
            660                 665                 670
```

```
Gly Gln Ser Glu Glu Val His Lys Val Asn Gly Asn Asn Gln Ile Leu
        675                 680                 685

Ser Ser Val Arg Tyr Gly Gln Asp Leu Met Ser Ala Asp Asp Thr Gln
    690                 695                 700

Gly Thr Asp Leu Ser Arg Thr Ser Gly Leu Val Thr Leu Val Ser Asn
705                 710                 715                 720

Asp Pro Asn Leu Asp Leu Gly Gly Asp Ser Leu Thr Val Asn Met Gly
                725                 730                 735

Arg Ala His Ala Asn Gln Ala Tyr Arg Pro Leu Ile Leu Gly Thr Lys
            740                 745                 750

Asp Gly Val Gln Ser Tyr Leu Lys Asp Ser Asp Thr Asn Ile Val Lys
        755                 760                 765

Tyr Thr Asp Ala Asn Gly Asn Leu Thr Phe Thr Ala Asp Asp Ile Lys
    770                 775                 780

Gly Tyr Ser Thr Val Asp Met Ser Gly Tyr Leu Ala Val Trp Val Pro
785                 790                 795                 800

Val Gly Ala Lys Asp Gly Gln Asp Val Arg Val Ala Ala Asp Thr Asn
                805                 810                 815

Gln Lys Ala Asp Gly Lys Ser Leu Lys Thr Ser Ala Ala Leu Asp Ser
            820                 825                 830

Gln Val Ile Tyr Glu Gly Phe Ser Asn Phe Gln Asp Phe Ala Asn Asn
        835                 840                 845

Asp Ala Asp Tyr Thr Asn Lys Lys Ile Ala Glu Asn Ala Asp Phe Phe
    850                 855                 860

Lys Lys Leu Gly Ile Thr Ser Phe Glu Met Ala Pro Gln Tyr Val Ser
865                 870                 875                 880

Ala Thr Asp Gly Ser Phe Leu Asp Ser Ile Ile Gln Asn Gly Tyr Ala
                885                 890                 895

Phe Ser Asp Arg Tyr Asp Leu Ala Met Ser Lys Asn Asn Lys Tyr Gly
            900                 905                 910

Ser Lys Asp Asp Leu Ala Asn Ala Leu Lys Ala Leu His Ala Asn Gly
        915                 920                 925

Ile Gln Ala Ile Ala Asp Trp Val Pro Asp Gln Ile Tyr Gln Leu Pro
    930                 935                 940

Gly Glu Glu Val Val Thr Ala Lys Arg Thr Asn Ser Tyr Gly Asn Pro
945                 950                 955                 960

Thr Phe Asp Ala Tyr Ile Asn Asn Ala Leu Tyr Ala Thr Asn Thr Lys
                965                 970                 975

Ser Ser Gly Ser Asp Tyr Gln Ala Gln Tyr Gly Gly Ala Phe Leu Asp
            980                 985                 990

Glu Leu Lys Ala Lys Tyr Pro Asp  Met Phe Thr Val Asn  Met Ile Ser
        995                 1000                1005

Thr Gly  Lys Pro Ile Asp Pro  Ser Thr Lys Ile Lys  Gln Trp Glu
    1010                1015                1020

Ala Lys  Tyr Phe Asn Gly Thr  Asn Val Leu Gly Lys  Gly Ala Gly
    1025                1030                1035

Tyr Val  Leu Ser Asp Asp Ala  Thr Gly Lys Tyr Phe  Thr Val Asn
    1040                1045                1050

Glu Asn  Gly Asp Phe Leu Pro  Ala Ser Phe Thr Gly  Asp Gln Asn
    1055                1060                1065

Ala Lys  Thr Gly Phe Tyr Tyr  Asp Gly Thr Gly Met  Ala Tyr Tyr
    1070                1075                1080

Ser Thr  Ser Gly Asn Lys Ala  Val Asn Ser Phe Ile  Tyr Glu Gly
    1085                1090                1095
```

```
Gly His Tyr Tyr Tyr Phe Asp Lys Asp Gly His Met Val Thr Gly
    1100                1105                1110

Ser Tyr Lys Ala Glu Asp Gly Asn Asp Tyr Tyr Phe Leu Pro Asn
    1115                1120                1125

Gly Ile Gln Met Arg Asp Ala Ile Tyr Gln Asp Ala Gln Gly Asn
    1130                1135                1140

Ser Tyr Tyr Tyr Gly Arg Thr Gly Ile Leu Tyr Lys Gly Asp Asn
    1145                1150                1155

Trp Tyr Pro Phe Val Asp Pro Asn Asn Ala Asn Lys Thr Val Phe
    1160                1165                1170

Arg Tyr Phe Asp Ala Asn Asn Val Met Ala Ile Gly Tyr Arg Asn
    1175                1180                1185

Met Tyr Gly Gln Thr Tyr Tyr Phe Asp Glu Asn Gly Phe Gln Ala
    1190                1195                1200

Lys Gly Gln Leu Leu Thr Asp Asp Lys Gly Thr His Tyr Phe Asp
    1205                1210                1215

Glu Asp Asn Gly Ala Met Ala Lys Asn Lys Phe Val Asn Val Gly
    1220                1225                1230

Asp Asp Trp Tyr Tyr Met Asp Gly Asn Gly Asn Ala Val Lys Gly
    1235                1240                1245

Gln Tyr Pro Val Asn Asn Gln Ile Leu Tyr Phe Asn Pro Glu Thr
    1250                1255                1260

Gly Val Gln Val Lys Gly Gln Phe Ile Thr Asp Ala Gln Gly Arg
    1265                1270                1275

Thr Ser Tyr Tyr Asp Ala Asn Ser Gly Ala Leu Lys Ser Ser Gly
    1280                1285                1290

Phe Phe Thr Pro Asn Gly Ser Asp Trp Tyr Tyr Ala Glu Asn Gly
    1295                1300                1305

Tyr Val Tyr Lys Gly Phe Lys Gln Val Ala Glu Asn Gln Asp Gln
    1310                1315                1320

Trp Tyr Tyr Phe Asp Gln Thr Thr Gly Lys Gln Ala Lys Gly Ala
    1325                1330                1335

Ala Lys Val Asp Gly Arg Asp Leu Tyr Phe Asn Pro Asp Ser Gly
    1340                1345                1350

Val Gln Val Lys Gly Asp Phe Ala Thr Asp Glu Ser Gly Asn Thr
    1355                1360                1365

Ser Phe Tyr His Gly Asp Asn Gly Asp Lys Val Val Gly Gly Phe
    1370                1375                1380

Phe Thr Thr Gly Asn Asn Ala Trp Tyr Tyr Ala Asp Asn Asn Gly
    1385                1390                1395

Asn Leu Val Lys Gly Phe Gln Glu Ile Asp Gly Lys Trp Tyr His
    1400                1405                1410

Phe Asp Glu Val Thr Gly Gln Gln Ala Lys Gly Ala Ala Leu Val
    1415                1420                1425

Asn Gly Gln Gln Leu Tyr Phe Asp Val Asp Ser Gly Ile Gln Val
    1430                1435                1440

Lys Gly Asp Phe Val Thr Asp Gly Gln Gly Asn Thr Ser Tyr Tyr
    1445                1450                1455

Asp Val Asn Ser Gly Asp Lys Lys Val Asn Gly Phe Phe Thr Thr
    1460                1465                1470

Gly Asp Asn Ala Trp Tyr Tyr Ala Asp Gly Gln Gly Asn Leu Ala
    1475                1480                1485

Lys Gly Arg Lys Ser Ile Asp Asn Gln Asp Leu Tyr Phe Asp Pro
```

```
    1490                1495                1500

Ala Thr  Gly Lys Gln Val Lys  Gly Gln Leu Val Ser  Ile Asp Gly
    1505                1510                1515

Arg Asn  Tyr Tyr Phe Asp Ser  Gly Ser Gly Asn Met  Ala Lys Asn
    1520                1525                1530

Arg Phe  Val Arg Ile Gly Asp  Gln Trp Ile Tyr Phe  Gly Asn Asp
    1535                1540                1545

Gly Ala  Ala Thr Asn Leu
    1550
```

<210> SEQ ID NO 18
<211> LENGTH: 1506
<212> TYPE: PRT
<213> ORGANISM: Streptococcus sobrinus

<400> SEQUENCE: 18

```
Met Glu Arg Lys Leu His Tyr Lys Leu His Lys Val Lys Lys Gln Trp
1               5                   10                  15

Val Thr Ile Ala Val Ala Ser Ala Gly Leu Ala Ser Ile Val Gly Ala
            20                  25                  30

Gly Ser Leu Ser Gln Thr Val Ser Ala Asp Asp Leu Ala Lys Glu Gln
        35                  40                  45

Ala Ala Ala Ser Gln Gln Lys Ala Ala Ala Asn Gln Asn Glu Asp Glu
    50                  55                  60

Val Ala Ser Asp Ala Ala Asp Thr Ala Ser Ala Lys Ala Thr Ser Glu
65                  70                  75                  80

Lys Glu Val Val Gln Ser Ser Asp Thr Asn Ser Glu Thr Asn Gln Val
                85                  90                  95

Glu Thr Lys Asp Gln Ala Ser Ala Lys Glu Ser Ala Asp Ala Val Ala
            100                 105                 110

Lys Gln Ala Pro Gln Ala Gly Pro Ala Thr Thr Ser Gln Val Ala Ser
        115                 120                 125

Ser Glu Ser Ser Ser Val Ala Pro Ser Lys Glu Ala Asp Lys Ala Ala
    130                 135                 140

Ala Gly Ser Val Ser Gln Asn Glu Glu Glu Ala Ala Leu Ser Leu Ala
145                 150                 155                 160

Asn Ile Lys Lys Ile Asp Gly Lys Tyr Tyr Tyr Val Met Ala Asp Gly
                165                 170                 175

Ser Tyr Lys Lys Asn Phe Ala Ile Thr Val Asp Gly Gln Met Leu Tyr
            180                 185                 190

Phe Asp Ala Lys Thr Gly Ala Leu Ser Ser Thr Ser Thr Tyr Ser Phe
        195                 200                 205

Ser Gln Gly Leu Thr Pro Ile Val Ser Asp Phe Ser Val Asn Asn Lys
    210                 215                 220

Ala Phe Asp Ser Ser Glu Lys Ser Phe Glu Leu Val Asp Gly Tyr Leu
225                 230                 235                 240

Thr Ala Glu Ser Trp Tyr Arg Pro Ala Lys Ile Leu Glu Asn Gly Lys
                245                 250                 255

Thr Trp Val Asp Ser Lys Glu Thr Asp Leu Arg Pro Val Leu Met Ser
            260                 265                 270

Trp Trp Pro Asn Lys Asp Thr Gln Val Ala Tyr Leu Asn Tyr Met Ser
        275                 280                 285

Lys Ala Leu Gly Gly Lys Glu Glu Phe Thr Thr Glu Thr Ser Gln Leu
    290                 295                 300

Thr Leu Asn Thr Ala Ala Glu Leu Ile Gln Ala Lys Ile Glu Ala Arg
```

-continued

```
305                 310                 315                 320

Val Ser Lys Glu Gln Gly Thr Lys Trp Leu Arg Glu Ala Met Ala Ala
                325                 330                 335

Phe Val Ala Thr Gln Ser Arg Trp Asn Lys Asp Ser Glu Gln Tyr Asp
            340                 345                 350

Lys Ala Asp His Leu Gln Gly Gly Ala Leu Leu Tyr Thr Asn Asn Asn
        355                 360                 365

Leu Thr Glu Trp Ala Asn Ser Asn Trp Arg Leu Leu Asn Arg Thr Pro
    370                 375                 380

Thr Arg Gln Asp Gly Lys Thr His Tyr Ser Lys Ala Asp Lys Tyr Gly
385                 390                 395                 400

Gly Tyr Glu Phe Leu Leu Ala Asn Asp Val Asp Asn Ser Asn Pro Val
                405                 410                 415

Val Gln Ala Glu Met Leu Asn Gln Ile His Tyr Leu Met Asn Trp Gly
            420                 425                 430

Glu Ile Val Met Gly Asp Lys Asn Ala Asn Phe Asp Gly Ile Arg Val
        435                 440                 445

Asp Ala Val Asp Asn Val Asn Ala Asp Thr Leu Gln Leu Tyr Thr Asn
    450                 455                 460

Tyr Phe Asn Ser Val Tyr Gly Val Asn Lys Ser Glu Ala Gln Ala Leu
465                 470                 475                 480

Ala His Ile Ser Val Leu Glu Ala Trp Ser Tyr Asn Asp Asn Asp Tyr
                485                 490                 495

Asn Gln Asp Thr Asn Gly Ala Ala Leu Ala Met Asp Asn Gly Leu Arg
            500                 505                 510

Phe Ser Leu Leu Tyr Thr Leu Thr Arg Pro Ile Asn Glu Arg Thr Pro
        515                 520                 525

Gly Met Ser Thr Leu Ile Lys Ser Glu Tyr Gly Leu Thr Asp Arg Thr
    530                 535                 540

Lys Asn Asp Lys Tyr Gly Asp Thr Gln Pro Ser Tyr Val Phe Val Arg
545                 550                 555                 560

Ala His Asp Ser Glu Val Gln Thr Val Ile Ala Gln Ile Ile Lys Glu
                565                 570                 575

Lys Ile Asp Pro Thr Thr Asp Gly Phe Thr Phe Thr Leu Asp Gln Leu
            580                 585                 590

Lys Gln Ala Phe Glu Ile Tyr Asn Lys Asp Met Asn Ser Val Asn Lys
        595                 600                 605

His Tyr Thr His Tyr Asn Ile Pro Ala Ala Tyr Ala Val Met Leu Ser
    610                 615                 620

Asn Met Glu Ser Val Thr Arg Val Tyr Tyr Gly Asp Leu Phe Thr Asp
625                 630                 635                 640

Asp Gly Gln Tyr Met Ala Ser Lys Ser Pro Tyr Tyr Asp Ala Ile Asn
                645                 650                 655

Thr Leu Leu Arg Ala Arg Ile Arg Tyr Ala Ala Gly Gly Gln Ile Met
            660                 665                 670

Glu His Asn Ser Tyr Lys Pro Ser Ala Ala Met Lys Ala Ala His Pro
        675                 680                 685

Asp Ala Gly Asn Val Leu Gly Asn Ser Glu Val Leu Val Ser Val Arg
    690                 695                 700

Phe Gly Gln Asp Val Met Ser Ala Asp Asp Met Thr Gly Gly Lys Leu
705                 710                 715                 720

Ala Lys Thr Ser Gly Met Phe Thr Leu Ile Ser Asn Asn Pro Glu Leu
                725                 730                 735
```

```
Glu Leu Asp Val Asn Glu Glu Ile Lys Val Asn Val Gly Lys Ile His
            740                 745                 750

Ala Gly Gln Ala Tyr Arg Pro Leu Leu Leu Thr Thr Asp Lys Gly Leu
        755                 760                 765

Gln Lys Tyr Leu Asn Asp Ser Asp Thr Lys Leu Thr Lys Ile Ala Asp
    770                 775                 780

Lys Asp Gly Phe Ile Thr Phe Lys Gly Ser Glu Ile Lys Gly Tyr Lys
785                 790                 795                 800

Gln Val Glu Val Asn Gly Tyr Leu Ser Val Trp Val Pro Val Gly Ala
                805                 810                 815

Lys Ala Asp Gln Asp Ile Arg Val Ala Pro Ser Thr Ala Ala Lys Gly
            820                 825                 830

Glu Lys Ala Lys Thr Tyr Thr Ala Ser Gln Ala Leu Glu Ser Gln Leu
        835                 840                 845

Ile Tyr Glu Gly Phe Ser Asn Phe Gln Asp Phe Val Gln Lys Asp Ser
    850                 855                 860

Gln Tyr Thr Asn Lys Lys Ile Ala Glu Asn Thr Asp Leu Phe Lys Ala
865                 870                 875                 880

Trp Gly Val Thr Ser Phe Glu Met Ala Pro Gln Tyr Val Ser Ala Thr
                885                 890                 895

Asp Gly Thr Phe Leu Asp Ser Ile Ile Glu Asn Gly Tyr Ala Phe Thr
            900                 905                 910

Asp Arg Tyr Asp Leu Ala Met Ser Lys Asn Asn Lys Tyr Gly Ser Lys
        915                 920                 925

Glu Asp Leu Ala Asn Ala Leu Lys Ala Leu His Ala Ala Gly Ile Gln
    930                 935                 940

Ala Ile Ala Asp Trp Val Pro Asp Gln Ile Tyr Gln Leu Pro Gly Lys
945                 950                 955                 960

Glu Val Val Thr Ala Ser Arg Val Asp Asn Tyr Gly Arg Val Lys Val
                965                 970                 975

Asp Gln Pro Leu Val Glu Lys Leu Tyr Leu Ala Asn Thr Lys Ser Ser
            980                 985                 990

Gly Lys Asp Phe Gln Ala Lys Tyr  Gly Gly Glu Phe Leu  Ala Glu Leu
        995                 1000                 1005

Gln Lys  Lys Tyr Pro Glu Met  Phe Thr Thr Lys Met  Ile Ser Thr
    1010                 1015                 1020

Gly Lys  Thr Ile Asp Pro Ser  Val Lys Leu Lys Glu  Trp Ser Ala
    1025                 1030                 1035

Lys Tyr  Phe Asn Gly Thr Asn  Val Leu Asp Arg Gly  Thr Asp Tyr
    1040                 1045                 1050

Ile Leu  Ser Asp Glu Gly Thr  Gly Lys Tyr Phe Thr  Val Asn Glu
    1055                 1060                 1065

Lys Gly  Asp Phe Leu Pro Ala  Ser Leu Thr Gly Asn  Lys Asp Ala
    1070                 1075                 1080

Lys Thr  Gly Phe Tyr Asn Asp  Gly Lys Gly Ile Val  Tyr Tyr Thr
    1085                 1090                 1095

Thr Ala  Gly Asn Lys Ala Arg  Ser Ala Phe Val Thr  Glu Ala Gly
    1100                 1105                 1110

Asn Thr  Tyr Tyr Phe Asp Tyr  Thr Gly His Met Val  Thr Gly Pro
    1115                 1120                 1125

Asn Val  Ile Asn Thr Lys Phe  Tyr Tyr Phe Leu Pro  Asn Gly Ile
    1130                 1135                 1140

Met Leu  Lys Asp Ala Ile Lys  Gln Asp Glu Lys Gly  Arg Ser Val
    1145                 1150                 1155
```

```
Tyr Tyr Gly Lys Thr Gly Val Met Tyr Lys Gly Gly Arg Asp Asn
    1160                1165                1170

Glu Trp Phe Ala Met Thr Asp Ser Lys Gly Gln Met Arg Phe Arg
    1175                1180                1185

His Phe Asp Arg Tyr Gly Phe Met Ser Ile Gly Leu Val Thr Ile
    1190                1195                1200

Asn Gln Asn Val Gln Tyr Tyr Asp Glu Asn Gly Phe Gln Val Lys
    1205                1210                1215

Gly Glu Phe Val Thr Asp Gln Asp Gly Gln Thr Arg Tyr Phe Asp
    1220                1225                1230

Gln Gly Ser Gly Asn Leu Val Lys Gly Gln Phe Leu Asn Lys Asp
    1235                1240                1245

Gly Asn Trp Tyr Tyr Leu Asp Asp Gln Gly Leu Val Ala Lys Gly
    1250                1255                1260

Ala Gln Thr Ile Lys Gly Gln Lys Leu Tyr Phe Asp Thr Lys Thr
    1265                1270                1275

Gly Val Gln Val Lys Gly Asp Phe Val Thr Asp Lys Asp Gly Asn
    1280                1285                1290

Thr Phe Phe Tyr Ser Gly Asp Thr Gly Asp Leu Ile Leu Gly Gln
    1295                1300                1305

Phe Phe Ser Thr Gly Asn Asn Ala Trp Phe Tyr Ala Asp Glu Asn
    1310                1315                1320

Gly His Val Ala Lys Gly Ala Lys Thr Ile Arg Gly Gln Lys Leu
    1325                1330                1335

Tyr Phe Asp Thr Lys Thr Gly Gln Gln Ala Lys Gly Arg Phe Ile
    1340                1345                1350

Arg Asp Asp Lys Gly Val Arg Tyr Tyr Asp Ala Asp Thr Gly Thr
    1355                1360                1365

Leu Val Thr Asn Ala Phe Leu Glu Thr Lys Ala Gly Ser Asn Gln
    1370                1375                1380

Trp Tyr Tyr Met Gly Ala Asp Gly Tyr Ala Val Lys Gly Asn Gln
    1385                1390                1395

Thr Ile Lys Asn Gln His Met Tyr Phe Asp Ala Glu Thr Gly Gln
    1400                1405                1410

Gln Ala Lys Gly Ile Ile Val Thr Asp Ala Asn Gly Arg Lys Tyr
    1415                1420                1425

Phe Tyr Asp Thr Phe Thr Gly Ser Arg Val Val Asn Gln Phe Val
    1430                1435                1440

Leu Val Asn Gly Asn Trp Tyr Phe Phe Gly Tyr Asp Gly Ala Ala
    1445                1450                1455

Val Thr Gly Phe His Asp Ile Lys Gly Gln His Leu Tyr Phe Asn
    1460                1465                1470

Ser Asp Gly Thr Gln Ala Lys Gly Thr Thr Val Lys Ile Gly Asn
    1475                1480                1485

Arg Ser Tyr Thr Phe Asp Ala His Thr Gly Glu Leu Thr Ser Val
    1490                1495                1500

His Tyr Gly
    1505
```

<210> SEQ ID NO 19
<211> LENGTH: 330
<212> TYPE: PRT
<213> ORGANISM: Streptococcus sobrinus

<400> SEQUENCE: 19

```
Met Gln Gly Lys Lys Thr Tyr Lys Met His Lys Val Lys Lys His Trp
1               5                   10                  15

Val Ser Ile Ala Gly Thr Ala Thr Val Leu Ser Val Ala Leu Leu Ala
            20                  25                  30

Asn Asn Gln Val Lys Ala Asp Glu Gln Thr Glu Ser Thr Val Val Arg
        35                  40                  45

Ala Asp Ser Ala Ala Val Val Thr Lys Pro Ala Asp Glu Thr Ser Gln
    50                  55                  60

Thr Asp Gln Ala Gln Pro Ala Thr Ala Glu Gln Thr Ala Thr Ala Asn
65                  70                  75                  80

Gln Asn Gln Gln Ala Ser Ala Asn Thr Ala Asp Gln Ala Gln Glu Gln
                85                  90                  95

Arg Gln Asp Thr Ala Asn Gln Asp Lys Trp Gln Ala Val Asp Gln Ala
            100                 105                 110

Ser Gln Pro Glu Gln Val Ala Thr Ala Val Asp Gln Val Gln Asn Ala
        115                 120                 125

Ala Lys Ser Asp Ala Asn Gln Val Val Ser Thr Asp Val Lys Asp Ser
    130                 135                 140

His Ala Val Val Ser Lys Asp Asp Ala Lys Ser Ser Ser Asp Gln Ala
145                 150                 155                 160

Ala Glu Gln Ala Gly Phe Tyr Thr Thr Gly Asn Asn Asp Trp Tyr Tyr
                165                 170                 175

Lys Gln Glu Asp Gly Asn Leu Ala Lys Gly Leu Gln Thr Ile Asn Gly
            180                 185                 190

Gln Thr Leu Tyr Phe Asp Thr Asn Thr Gly Lys Gln Val Lys Gly Ser
        195                 200                 205

Ala Val Thr Ile Asp Gly Lys Glu Tyr Tyr Phe Asp Gln Asp Thr Gly
    210                 215                 220

Asp Met Trp Lys Asp Arg Phe Arg Gln Ile Asp Lys Gln Asp Tyr Arg
225                 230                 235                 240

Gly Val Ala Pro Gly Ser Lys Val Gly Ile Ala Trp Leu Tyr Tyr Gln
                245                 250                 255

Ala Asp Gly Ser Val Ala Ser Gly Leu Thr Asn Thr Pro Asp Gly Arg
            260                 265                 270

Thr Leu Met Phe Asn Thr Tyr Asn His Glu Gln Val Lys Gly Lys Leu
        275                 280                 285

Val Asn Thr Asp Gly Ser Asn Tyr Arg Tyr Phe Asp Leu His Thr Gly
    290                 295                 300

Asp Met Leu Arg Asn Thr Ser Ile Tyr Asp Gly Ser Gln Lys Tyr Asn
305                 310                 315                 320

Ile Asp Glu Asn Gly Ile Ala Thr Lys Ala
                325                 330


<210> SEQ ID NO 20
<211> LENGTH: 302
<212> TYPE: PRT
<213> ORGANISM: Streptococcus sobrinus

<400> SEQUENCE: 20

Leu Asp Ser Gln Lys Glu Ile Cys Val Leu Gly Gly Ser Lys Ile Gly
1               5                   10                  15

Leu Val Glu Leu Pro Trp Ala Leu Met Asn Pro Gly Asp Leu Leu Leu
            20                  25                  30

Leu Pro Asp Pro Gly Tyr Pro Asp Tyr Leu Ser Gly Val Ala Leu Gly
        35                  40                  45
```

```
Arg Val Asp Tyr Glu Thr Phe Pro Leu Leu Ala Glu Asn Asp Phe Leu
    50                  55                  60

Pro Asp Leu Ala Ala Ile Pro Glu Glu Ile Ala Arg Arg Ala Lys Phe
65                  70                  75                  80

Ile Tyr Ile Asn Tyr Pro Asn Asn Pro Thr Gly Arg Val Ala Thr Ser
                85                  90                  95

Asp Phe Tyr Gln Asp Leu Val Ala Trp Ala Lys Lys Tyr Gln Val Gly
            100                 105                 110

Val Val Ser Asp Phe Ala Tyr Val Pro Trp Ala Thr Arg Ala Met Lys
        115                 120                 125

Ile Leu Ala Phe Cys Leu His Arg Gly Pro Arg Arg Ser Val Leu Asn
    130                 135                 140

Ser Ile Pro Ser Pro Arg Pro Leu Thr Trp Pro Ala Gly Arg Leu Ala
145                 150                 155                 160

Phe Ala Ala Gly Asn Ala Asp Met Ile Glu Ala Leu Asn Leu Ile Gln
                165                 170                 175

Asp His Leu Phe Val Ser Ile Phe Pro Ala Ile Gln Asp Ala Gly Val
            180                 185                 190

Ala Ala Leu Leu Asp Pro Gln Ala Lys Glu Ala Ile Val Gln Leu Asn
        195                 200                 205

Gln Ile Tyr Asp Gln Arg Arg Glu Ala Phe Val Gln Ala Ser Ala Lys
    210                 215                 220

Ile Gly Trp Gln Ala Phe Pro Ser Lys Gly Ser Phe Tyr Ala Trp Met
225                 230                 235                 240

Pro Val Pro Arg Gly Tyr Thr Ser Gln Ser Phe Ala Asp Leu Leu Leu
                245                 250                 255

Glu Lys Ala His Val Ala Val Ala Pro Gly Val Gly Phe Gly Gln Ala
            260                 265                 270

Gly Asp Gly Tyr Val Arg Ile Gly Leu Leu Val Glu Pro Glu Arg Leu
        275                 280                 285

Ala Glu Ala Val Glu Arg Ile Gly Ala Leu Asn Leu Phe Gly
    290                 295                 300


<210> SEQ ID NO 21
<211> LENGTH: 1528
<212> TYPE: PRT
<213> ORGANISM: Streptococcus sobrinus

<400> SEQUENCE: 21

Met Leu Gln Lys Cys Lys Leu Glu Gly Ile Ile Ile Cys Asn Glu Lys
1               5                   10                  15

Arg Leu Leu Gly Ala Ala Lys Val Lys Ser Gly Arg Thr Leu Ser Gly
            20                  25                  30

Ala Leu Leu Gly Thr Ala Ile Leu Ala Ser Gly Ala Gly Gln Lys Ala
        35                  40                  45

Leu Ala Glu Glu Thr Ser Thr Thr Ser Thr Ser Gly Gly Asp Thr Ala
    50                  55                  60

Val Val Gly Thr Glu Thr Gly Asn Pro Ala Thr Asn Leu Pro Asp Lys
65                  70                  75                  80

Gln Asp Asn Pro Ser Ser Gln Ala Glu Thr Ser Gln Ala Gln Ala Arg
                85                  90                  95

Gln Lys Thr Gly Ala Met Ser Val Asp Val Ser Thr Ser Glu Leu Asp
            100                 105                 110

Glu Ala Ala Lys Ser Pro Gln Glu Ala Gly Val Thr Val Ser Gln Asp
        115                 120                 125
```

```
Ala Thr Val Asn Lys Gly Thr Val Glu Pro Ser Asp Glu Ala Asn Gln
    130                 135                 140

Lys Glu Pro Glu Ile Lys Asp Asp Tyr Ser Lys Gln Ala Ala Asp Ile
145                 150                 155                 160

Gln Lys Ala Thr Glu Asp Tyr Lys Ala Ser Val Ala Ala Asn Gln Ala
                165                 170                 175

Glu Thr Asp Arg Ile Asn Gln Glu Ile Ala Ala Lys Lys Ala Gln Tyr
            180                 185                 190

Glu Gln Asp Leu Ala Ala Asn Lys Ala Glu Val Glu Arg Ser Leu Met
        195                 200                 205

Arg Met Arg Lys Pro Arg Pro Ile Tyr Glu Ala Lys Leu Ala Gln Asn
    210                 215                 220

Gln Lys Asp Leu Ala Ala Ile Gln Gln Ala Asn Ser Asp Ser Gln Ala
225                 230                 235                 240

Ala Tyr Ala Ala Ala Lys Glu Ala Tyr Asp Lys Glu Trp Ala Arg Val
                245                 250                 255

Gln Ala Ala Asn Ala Ala Ala Lys Lys Ala Tyr Glu Glu Ala Leu Ala
            260                 265                 270

Ala Asn Thr Ala Lys Asn Asp Gln Ile Lys Ala Glu Ile Glu Ala Ile
        275                 280                 285

Gln Gln Arg Ser Ala Lys Ala Asp Tyr Glu Ala Lys Leu Ala Gln Tyr
    290                 295                 300

Glu Lys Asp Leu Ala Ala Ala Gln Ala Gly Asn Ala Ala Asn Glu Ala
305                 310                 315                 320

Asp Tyr Gln Ala Lys Lys Ala Ala Tyr Glu Gln Glu Leu Ala Arg Val
                325                 330                 335

Gln Ala Ala Asn Ala Ala Ala Lys Gln Ala Tyr Glu Gln Ala Leu Ala
            340                 345                 350

Ala Asn Ser Ala Lys Asn Ala Gln Ile Thr Ala Glu Asn Glu Ala Ile
        355                 360                 365

Gln Gln Asn Ala Gln Ala Lys Ala Asp Tyr Glu Ala Lys Leu Ala Gln
    370                 375                 380

Tyr Gln Lys Asp Leu Ala Ala Ala Gln Ser Gly Asn Ala Ala Asn Glu
385                 390                 395                 400

Ala Asp Tyr Gln Glu Lys Leu Ala Ala Tyr Glu Lys Glu Leu Ala Arg
                405                 410                 415

Val Gln Ala Ala Asn Ala Ala Ala Lys Gln Ala Tyr Glu Gln Gln Val
            420                 425                 430

Gln Gln Ala Asn Ala Lys Asn Ala Glu Ile Thr Glu Ala Asn Arg Ala
        435                 440                 445

Ile Arg Glu Arg Asn Ala Lys Ala Lys Thr Asp Tyr Glu Leu Lys Leu
    450                 455                 460

Ser Lys Tyr Gln Glu Glu Leu Ala Gln Tyr Lys Lys Asp Leu Ala Glu
465                 470                 475                 480

Tyr Pro Ala Lys Leu Gln Ala Tyr Gln Asp Glu Gln Ala Ala Ile Lys
                485                 490                 495

Ala Ala Leu Ala Glu Leu Glu Lys His Lys Asn Glu Asp Gly Asn Leu
            500                 505                 510

Ser Glu Pro Ser Ala Gln Ser Leu Val Tyr Asp Leu Glu Pro Asn Ala
        515                 520                 525

Gln Val Ala Leu Val Thr Asp Gly Lys Leu Leu Lys Ala Ser Ala Leu
    530                 535                 540

Asp Glu Ala Phe Ser His Asp Glu Lys Asn Tyr Asn Asn His Leu Leu
```

```
545                 550                 555                 560

Gln Pro Asp Asn Leu Asn Val Thr Tyr Leu Glu Gln Ala Asp Asp Val
                565                 570                 575

Ala Ser Ser Val Glu Leu Phe Gly Asn Phe Gly Asp Lys Ala Gly Trp
            580                 585                 590

Thr Thr Thr Val Ser Asn Gly Ala Glu Val Lys Phe Ala Ser Val Leu
        595                 600                 605

Leu Lys Arg Gly Gln Ser Ala Thr Ala Thr Tyr Thr Asn Leu Lys Asn
    610                 615                 620

Ser Tyr Tyr Asn Gly Lys Lys Ile Ser Lys Val Val Tyr Lys Tyr Thr
625                 630                 635                 640

Val Asp Pro Asp Ser Lys Phe Gln Asn Pro Thr Gly Asn Val Trp Leu
                645                 650                 655

Gly Ile Phe Thr Asp Pro Thr Leu Gly Val Phe Ala Ser Ala Tyr Thr
            660                 665                 670

Gly Gln Asn Glu Lys Asp Thr Ser Ile Phe Ile Lys Asn Glu Phe Thr
        675                 680                 685

Phe Tyr Asp Glu Asp Gly Asn Pro Ile Asp Phe Asp Asn Ala Leu Leu
    690                 695                 700

Ser Val Ala Ser Leu Asn Arg Glu His Asn Ser Ile Glu Met Ala Lys
705                 710                 715                 720

Asp Tyr Ser Gly Thr Phe Val Lys Ile Ser Gly Ser Ser Ile Gly Glu
                725                 730                 735

Lys Asn Gly Met Ile Tyr Ala Thr Asp Thr Leu Asn Phe Lys Lys Gly
            740                 745                 750

Glu Gly Gly Ser Leu His Thr Met Tyr Thr Arg Ala Ser Glu Pro Gly
        755                 760                 765

Ser Gly Trp Asp Ser Ala Asp Ala Pro Asn Ser Trp Tyr Gly Ala Gly
    770                 775                 780

Ala Val Arg Met Ser Gly Pro Asn Asn Tyr Ile Thr Leu Gly Ala Thr
785                 790                 795                 800

Ser Ala Thr Asn Val Leu Ser Leu Ala Glu Met Pro Gln Val Pro Gly
                805                 810                 815

Lys Asp Asn Thr Ala Gly Lys Lys Pro Asn Ile Trp Tyr Ser Leu Asn
            820                 825                 830

Gly Lys Ile Arg Ala Val Asn Val Pro Lys Val Thr Lys Glu Lys Pro
        835                 840                 845

Thr Pro Pro Val Glu Pro Thr Lys Pro Asp Glu Pro Thr Tyr Glu Val
    850                 855                 860

Glu Lys Glu Leu Val Asp Leu Pro Val Glu Pro Lys Tyr Glu Pro Glu
865                 870                 875                 880

Pro Thr Pro Pro Ser Lys Asn Pro Asp Gln Ser Ile Pro Glu Lys Pro
                885                 890                 895

Val Glu Pro Thr Tyr Glu Val Glu Lys Glu Leu Glu Pro Ala Pro Val
            900                 905                 910

Glu Pro Ser Tyr Glu Lys Glu Pro Thr Pro Pro Gln Ser Thr Pro Asp
        915                 920                 925

Gln Glu Glu Pro Glu Lys Pro Val Glu Pro Ser Tyr Gln Ser Leu Pro
    930                 935                 940

Thr Pro Pro Val Glu Pro Val Tyr Glu Thr Val Pro Gly Pro Val Ser
945                 950                 955                 960

Val Pro Thr Val Arg Tyr His Tyr Tyr Lys Leu Ala Val Gln Pro Gly
                965                 970                 975
```

```
Val Thr Lys Glu Ile Lys Asn Gln Asp Asp Leu Asp Ile Asp Lys Thr
            980                 985                 990

Leu Val Ala Lys Gln Ser Thr Val  Lys Phe Gln Leu Lys  Thr Ala Asp
        995                 1000                1005

Leu Pro  Ala Gly Arg Pro Glu  Thr Thr Ser Phe Val  Leu Met Asp
    1010                 1015                1020

Pro Leu  Pro Ser Gly Tyr Gln  Leu Asn Leu Glu Ala  Thr Lys Val
    1025                 1030                1035

Ala Ser  Pro Gly Phe Glu Ala  Ser Tyr Asp Ala Met  Thr His Thr
    1040                 1045                1050

Val Thr  Phe Thr Ala Thr Ala  Glu Thr Leu Ala Ala  Leu Asn Gln
    1055                 1060                1065

Asp Leu  Thr Lys Ala Val Ala  Thr Ile Tyr Pro Thr  Val Val Gly
    1070                 1075                1080

Gln Val  Leu Asn Asp Gly Ala  Thr Tyr Thr Asn Asn  Phe Thr Leu
    1085                 1090                1095

Met Val  Asn Asp Ala Tyr Gly  Ile Lys Ser Asn Ile  Val Arg Val
    1100                 1105                1110

Thr Thr  Pro Gly Lys Pro Asn  Asp Pro Asp Asn Pro  Ser Asn Asn
    1115                 1120                1125

Tyr Ile  Thr Pro His Lys Val  Asn Lys Asn Glu Asn  Gly Val Val
    1130                 1135                1140

Ile Asp  Gly Lys Ser Val Leu  Ala Gly Thr Thr Asn  Tyr Tyr Glu
    1145                 1150                1155

Leu Thr  Trp Asp Leu Asp Gln  Tyr Lys Gly Asp Lys  Ser Ala Lys
    1160                 1165                1170

Glu Ile  Ile Gln Lys Gly Phe  Phe Tyr Val Asp Asp  Tyr Pro Glu
    1175                 1180                1185

Glu Ala  Leu Asp Leu Arg Thr  Asp Leu Ile Lys Leu  Thr Asp Ala
    1190                 1195                1200

Asn Gly  Lys Ala Val Thr Gly  Val Ser Val Ala Asp  Tyr Ala Ser
    1205                 1210                1215

Leu Glu  Ala Ala Pro Ala Ala  Val Gln Asp Met Leu  Lys Lys Ala
    1220                 1225                1230

Asn Ile  Ile Pro Lys Gly Ala  Phe Gln Val Phe Thr  Ala Asp Asp
    1235                 1240                1245

Pro Gln  Ala Phe Tyr Asp Ala  Tyr Val Val Thr Gly  Thr Asp Leu
    1250                 1255                1260

Thr Ile  Val Thr Pro Met Thr  Val Lys Ala Glu Met  Gly Lys Thr
    1265                 1270                1275

Gly Gly  Ser Tyr Glu Asn Arg  Ala Tyr Gln Ile Asp  Phe Gly Asn
    1280                 1285                1290

Gly Tyr  Glu Ser Asn Leu Val  Val Asn Asn Val Pro  Lys Ile Asn
    1295                 1300                1305

Pro Glu  Lys Asp Val Thr Leu  Thr Met Asp Pro Ala  Asp Ser Thr
    1310                 1315                1320

Asn Val  Asp Gly Gln Thr Ile  Ala Leu Asn Gln Val  Phe Asn Tyr
    1325                 1330                1335

Arg Leu  Ile Gly Gly Ile Ile  Pro Ala Asp His Ala  Glu Glu Leu
    1340                 1345                1350

Phe Glu  Tyr Ser Phe Ser Asp  Asp Tyr Asp Gln Thr  Gly Asp Gln
    1355                 1360                1365

Tyr Thr  Gly Gln Tyr Lys Ala  Phe Ala Lys Val Asp  Leu Thr Leu
    1370                 1375                1380
```

```
Lys Asp  Gly Thr Ile Ile Lys  Ala Gly Thr Asp Leu  Thr Ser Tyr
    1385                 1390                 1395

Thr Glu  Ala Gln Val Asp Glu  Ala Asn Gly Gln Ile  Val Val Thr
    1400                 1405                 1410

Phe Lys  Glu Asp Phe Leu Arg  Ser Val Ser Val Asp  Ser Ala Phe
    1415                 1420                 1425

Gln Ala  Glu Val Tyr Leu Gln  Met Lys Arg Ile Ala  Val Gly Thr
    1430                 1435                 1440

Phe Ala  Asn Thr Tyr Val Asn  Thr Val Asn Gly Ile  Thr Tyr Ser
    1445                 1450                 1455

Ser Asn  Thr Val Arg Thr Ser  Thr Pro Glu Pro Lys  Gln Pro Ser
    1460                 1465                 1470

Pro Val  Asp Pro Lys Thr Thr  Thr Thr Val Val Phe  Gln Pro Arg
    1475                 1480                 1485

Gln Gly  Lys Ala Tyr Gln Pro  Ala Pro Pro Ala Gly  Ala Gln Leu
    1490                 1495                 1500

Pro Ala  Thr Gly Asp Ser Ser  Asn Ala Tyr Leu Pro  Leu Leu Gly
    1505                 1510                 1515

Leu Val  Ser Leu Thr Ala Gly  Phe Ser Cys
    1520                 1525


<210> SEQ ID NO 22
<211> LENGTH: 81
<212> TYPE: PRT
<213> ORGANISM: Lactobacillus

<400> SEQUENCE: 22

Met Ile Ser Met Ile Ser Ser His Gln Lys Thr Leu Thr Asp Lys Glu
1               5                   10                  15

Leu Ala Leu Ile Ser Gly Gly Lys Thr Tyr Tyr Gly Thr Asn Gly Val
            20                  25                  30

His Cys Thr Lys Lys Ser Leu Trp Gly Lys Val Arg Leu Lys Asn Val
        35                  40                  45

Ile Pro Gly Thr Leu Cys Arg Lys Gln Ser Leu Pro Ile Lys Gln Asp
    50                  55                  60

Leu Lys Ile Leu Leu Gly Trp Ala Thr Gly Ala Phe Gly Lys Thr Phe
65                  70                  75                  80

His


<210> SEQ ID NO 23
<211> LENGTH: 91
<212> TYPE: PRT
<213> ORGANISM: Lactobacillus

<400> SEQUENCE: 23

Met Val Thr Lys Tyr Gly Arg Asn Leu Gly Leu Ser Lys Val Glu Leu
1               5                   10                  15

Phe Ala Ile Trp Ala Val Leu Val Val Ala Leu Leu Leu Ala Thr Ala
            20                  25                  30

Asn Ile Tyr Trp Ile Ala Asp Gln Phe Gly Ile His Leu Ala Thr Gly
        35                  40                  45

Thr Ala Arg Lys Leu Leu Asp Ala Val Ala Ser Gly Ala Ser Leu Gly
    50                  55                  60

Thr Ala Phe Ala Ala Ile Leu Gly Val Thr Leu Pro Ala Trp Ala Leu
65                  70                  75                  80

Ala Ala Ala Gly Ala Leu Gly Ala Thr Ala Ala
```

85 90

<210> SEQ ID NO 24
<211> LENGTH: 83
<212> TYPE: PRT
<213> ORGANISM: Lactobacillus

<400> SEQUENCE: 24

Ser Arg Asp Leu Leu Leu Phe Ser Asn Phe Gly Gly Gly Ala Val Leu
1 5 10 15

Leu Ser Tyr Lys Glu Leu Asp Thr Ala Lys Leu Gln Glu Ile Ser Gly
20 25 30

Gly Tyr Ser Tyr Phe Gly Gly Ser Asn Gly Tyr Ser Trp Arg Asp Lys
35 40 45

Arg Gly His Trp His Tyr Thr Val Thr Lys Gly Gly Phe Glu Thr Val
50 55 60

Ile Gly Ile Ile Gly Asp Gly Trp Gly Ser Ala Gly Ala Pro Gly Pro
65 70 75 80

Gly Gln His

<210> SEQ ID NO 25
<211> LENGTH: 46
<212> TYPE: PRT
<213> ORGANISM: Lactobacillus

<400> SEQUENCE: 25

Met Ile Ser Ser His Gln Lys Thr Leu Thr Asp Lys Glu Leu Ala Leu
1 5 10 15

Ile Ser Gly Gly Lys Thr His Tyr Pro Thr Asn Ala Trp Lys Ser Leu
20 25 30

Trp Lys Gly Phe Trp Glu Ser Leu Arg Tyr Thr Asp Gly Phe
35 40 45

<210> SEQ ID NO 26
<211> LENGTH: 4689
<212> TYPE: DNA
<213> ORGANISM: Streptococcus mutans

<400> SEQUENCE: 26
atgaaagtca aaaaaactta cggttttcgt aaaagtaaaa ttagtaaaac actgtgtggt 60
gctgttctag gaacagtagc agcagtctct gtagcaggac aaaaggtttt tgccgatgaa 120
acgaccacta ctagtgatgt agatactaaa gtagttggaa cacaaactgg aaatccagcg 180
accaatttgc cagaggctca agggagtgcg agtaaggaag ctgaacaaag tcaaaaccaa 240
gctggagaga caaatggttc aataccagtt gaagtaccta aaactgatct tgatcaagca 300
gcaaaagatg ctaagtctgc tggtgtcaat gttgtccaag atgccgatgt taataaagga 360
actgttaaaa cagctgaaga agcagtccaa aaagaaactg aaattaaaga agattacaca 420
aaacaagctg aggatattaa gaagacaaca gatcaatata aatcggatgt agctgctcat 480
gaggcagaag ttgctaaaat caaagctaaa aatcaggcaa ctaaagaaca gtatgaaaaa 540
gatatggcag ctcataaagc cgaggttgaa cgcattaatg ctgcaaatgc tgccagtaaa 600
acagcttatg aagctaaatt ggctcaatat caagcagatt tagcagccgt tcaaaaaacc 660
aatgctgcca atcaagcagc ctatcaaaaa gcccttgctg cttatcaggc tgaactgaaa 720
cgtgttcagg aagctaatgc agccgccaaa gccgcttatg atactgctgt agcagcaaat 780
aatgctaaaa atacagaaat tgccgctgcc aatgaagaaa ttagaaaacg caatgcaacg 840

```
gccaaagctg aatatgagac taagttagct caatatcaag ctgaactaaa gcgtgttcag     900
gaagctaatg ccgcaaacga agcagactat caagctaaat tgaccgccta tcaaacagag     960
cttgctcgcg ttcaaaaagc caatgcggat gctaaagcgg cctatgaagc agctgtagca    1020
gcaaataatg ccaaaaatgc ggcactcaca gctgaaaata ctgcaattaa gcaacgcaat    1080
gagaatgcta aggcgactta tgaagctgca ctcaagcaat atgaggccga tttggcagcg    1140
gtgaaaaaag ctaatgccgc aaacgaagca gactatcaag ctaaattgac cgcctatcaa    1200
acagagctcg ctcgcgttca aaaagccaat gcggatgcta aagcggccta tgaagcagct    1260
gtagcagcaa ataatgccgc aaatgcagcg ctcacagctg aaaatactgc aattaaaaag    1320
cgcaatgcgg atgctaaagc tgattacgaa gcaaaacttg ctaagtatca agcagatctt    1380
gccaaatatc aaaaagattt agcagactat ccagttaagt taaaggcata cgaagatgaa    1440
caagcttcta ttaaagctgc actggcagag cttgaaaaac ataaaaatga agacggaaac    1500
ttaacagaac catctgctca aaatttggtc tatgatcttg agccaaatgc gaacttatct    1560
ttgacaacag atgggaagtt ccttaaggct tctgctgtgg atgatgcttt tagcaaaagc    1620
acttcaaaag caaaatatga ccaaaaaatt cttcaattag atgatctaga tatcactaac    1680
ttagaacaat ctaatgatgt tgcttcttct atggagcttt atgggaattt tggtgataaa    1740
gctggctggt caacgacagt aagcaataac tcacaggtta aatggggatc ggtactttta    1800
gagcgcggtc aaagcgcaac agctacatac actaacctgc agaattctta ttacaatggt    1860
aaaaagattt ctaaaattgt ctacaagtat acagtggacc ctaagtccaa gtttcaaggt    1920
caaaaggttt ggttaggtat ttttaccgat ccaactttag gtgtttttgc ttccgcttat    1980
acaggtcaag ttgaaaaaaa cacttctatt tttattaaaa atgaattcac tttctatgac    2040
gaagatggaa aaccaattaa ttttgataat gcccttctat cagtagcttc tcttaaccgt    2100
gaaaataatt ctattgagat ggccaaagat tatacgggta aatttgtcaa aatctctgga    2160
tcatctatcg gtgaaaagaa tggcatgatt tatgctacag atactctcaa ctttaggcag    2220
ggtcaaggtg gtgctcgttg gaccatgtat accagagcta gcgaaccggg atctggctgg    2280
gatagttcag atgcgcctaa ctcttggtat ggtgctggtg ctatccgcat gtctggtcct    2340
aataacagtg tgactttggg tgctatctca tcaacacttg ttgtgcctgc tgatcctaca    2400
atggcaattg aaactggcaa aaaaccaaat atttggtatt ctttaaatgg taaaatccgt    2460
gcggttaatg ttcctaaagt taccaaggaa aaacccacac cgccggttaa accaacagct    2520
ccaactaaac caacttatga aacagaaaag ccattaaaac cggcaccagt agctccaaat    2580
tatgaaaagg agccaacacc gccgacaagg acaccggatc aagcagagcc aaacaaaccc    2640
acaccgccga cctatgaaac agaaaagccg ttggagccag cacctgttga gccaagctat    2700
gaagcagagc caacaccgcc gacaaggaca ccggatcagg cagagccaaa taaacccaca    2760
ccgccgacct atgaaacaga aaagccgttg gagccagcac ctgttgagcc aagctatgaa    2820
gcagagccaa cgccaccgac accaacacca gatcaaccag aaccaaacaa acctgttgag    2880
ccaacttatg aggttattcc aacaccgccg actgatcctg tttatcaaga tcttccaaca    2940
cctccatctg taccaactgt tcatttccat tactttaaac tagctgttca gccgcaggtt    3000
aacaaagaaa ttagaaacaa taacgatatt aatattgaca gaactttggt ggctaaacaa    3060
tctgttgtta agttccagct gaagacagca gatctccctg ctggacgtga tgaaacaact    3120
tcctttgtct tggtagatcc cctgccatct ggttatcaat ttaatcctga agctacaaaa    3180
gctgcaagcc ctggctttga tgtcacttat gataatgcaa ctaatacagt caccttcaag    3240
```

```
gcaactgcag caactttggc tacgtttaat gctgatttga ctaagtcagt ggcaacgatt   3300

tatccaacag tggtcggaca agttcttaat gatggcgcaa cttataagaa taatttcacg   3360

ctcacagtca atgatgctta tggcattaaa tccaatgttg ttcgggtgac aactcctggt   3420

aaaccaaatg atccagataa tccaaataat aattatatta aaccaactaa ggttaataaa   3480

aacgaaaatg gcgttgttat tgatggtaaa acagttcttg ccggttcaac gaattattat   3540

gagctaactt gggatttgga tcaatataaa aacgaccgct cttcagcaga taccattcaa   3600

aaaggatttt actatgtaga tgattatcca gaagaagcgc ttgaattgcg tcaggattta   3660

gtgaagatta cagatgctaa tggtaatgaa gttactggtg ttagtgtgga taattatact   3720

aatcttgaag cagcccctca agaaattaga gatgttcttt ctaaggcagg aattagacct   3780

aaaggtgctt tccaaatttt ccgtgccgat aatccaagag aattttatga tacttatgtc   3840

aaaactggaa ttgatttgaa gattgtatca ccaatggttg ttaaaaaaca aatgggacaa   3900

acaggcggca gttatgaaaa tcaagcttac caaattgact ttggtaatgg ttatgcatca   3960

aatatcatta tcaataatgt tcctaagatt aaccctaaga aagatgtgac cttaacactt   4020

gatccggctg atacaaataa tgttgatggt cagactattc cacttaatac agtctttaat   4080

taccgtttga ttggtggcat tatccctgca gatcactcag aagaactctt tgaatacaat   4140

ttttatgatg attatgatca aacaggagat cactatactg gtcagtataa agtttttgct   4200

aaggttgata tcactttttaa agacggttct attatcaagt caggtgctga gttaactcag   4260

tatacgacag cggaagttga taccgctaaa ggtgctatca caattaagtt caaggaagcc   4320

tttctgcgtt ctgtttcaat tgattcagcc ttccaagctg aaagttatat ccaaatgaaa   4380

cgtattgcgg ttggtacttt tgaaaatact tatattaata ctgtcaatgg ggtaacttac   4440

agttcaaata cagtgaaaac aactactcct gaggatccta cagaccctac tgatccgcaa   4500

gatccatcat caccgcggac ttcaactgta attaactaca aacctcaatc aactgcttat   4560

caaccaagct ctgttcaaga aacattacca aatacgggag taacaaacaa tgcttatatg   4620

cctttacttg gtattattgg cttagttact agttttagtt tgcttggctt aaaggctaag   4680

aaagattga                                                           4689
```

<210> SEQ ID NO 27
<211> LENGTH: 1362
<212> TYPE: DNA
<213> ORGANISM: Streptococcus mutans

<400> SEQUENCE: 27

```
atgaaaatga aacgtaaact attaagcttg gtttcagtcc ttactatttt attgggagct     60

ttttgggtaa cgaagattgt aaaagctgac caagtcacaa attatacaaa tacggcttct    120

atcacaaaat cagatggtac agcactttct aatgatccat ctaaggctgt taattattgg    180

gaaccacttt ctttcagtaa ttctattact ttcccagatg aagtcagtat taaggctggg    240

gatactttaa ccattaagtt gccagagcaa ttacaattta cgactgctct aactttcgat    300

gttatgcata ccaatgggca attagctggt aaagcaacaa ctgatcctaa tacaggagaa    360

gtaacagtta cctttactga tatttttgaa aaactgccta atgataaggc tatgacatta    420

aattttaatg cacaattgaa tcataacaat atttctattc ctggtgttgt aaactttaac    480

tataataatg ttgcttatag ctcttatgtt aaagacaaag atattacgcc aataagtcca    540

gatgttaaca aagtgggtta tcaggataaa agtaatcctg gtttgattca ctggaaagtt    600

ctcattaaca acaaacaagg tgctattgat aatttgactt tgactgatgt tgtcggagaa    660
```

```
gatcaagaaa tcgtaaaaga ttccttggtt gctgcacgct tgcagtacat tgctggtgat    720

gatgttgaca gtttagatga agctgcttcg cgaccttatg ctgaggattt ttcaaaaaat    780

gttacttatc aaactaatga tttaggattg acaacaggat ttacctatac aattccagga    840

tccagtaaca acgctatctt tatctcttat actactcgtt taacttcttc tcaatctgct    900

ggtaaagatg tcagcaacac tattgctatt tcaggaaata atattaatta ttccaatcaa    960

acaggctacg ctcgtattga atccgcatat ggtagagcta gttctagagt aaagaggcaa   1020

gcagaaacaa caactgttac tgaaacaaca acttcgtcat cttctgaaac gacaactagt   1080

gaagcgacaa cagaaacaag tagtacaaca aataataatt caactactac agaaacagct   1140

actagcacaa caggagcttc aacaacacaa acaaaaacga ctgcttctca aacgaatgtt   1200

ccgacaacaa caaacataac aacaacttca aaacaagtaa ccaagcaaaa agcgaaattt   1260

gttttaccat caacaggtga acaagcaggg cttttgttaa ctactgtagg tcttgtaatt   1320

gttgctgtgg caggtgtcta tttctataga acacgtcgtt aa                      1362
```

<210> SEQ ID NO 28
<211> LENGTH: 1698
<212> TYPE: DNA
<213> ORGANISM: Streptococcus mutans

<400> SEQUENCE: 28

```
ctagttacta ttgataactt caccgctgtc tttgtcaaaa gtatattctt taccatcgat     60

agtgatggtt tgtcctttaa tttgacggcc ctttgtcttt tcatcttggc taaagtagta    120

gcgcttaccg tcgatagttt gccagcctga tacacgtttg ccatcgcttc cataataata    180

ccaaatatta ctgtagtcgt attttctgac aaatctattc gttacgaatt gaccttgagt    240

atcaaaaaag taaccatctc catcaatctc tgcaaaaccg tcatcaggca cagaaccacc    300

aatttgacta tactctgact ttgcttttat gctgtgatca tccttaaagt aataagtttt    360

accatcaata atctgccaac cagttagatc tttgcggctg ccgtccgctc caaaataata    420

agttttaggg aaacgagcct caactgtact gatacgctcg gcaggtgttg tgccaaaacg    480

attcttaaca acttgtccac tgtcttcatc taaataatag accttgccat cacgctcagc    540

aatgtcgcct ttaacctgaa taccactgga aggttcgaaa tagtaatcca taccatcgat    600

cttttgccag tcggtcacgc cgataccatc ggctcccata tagaaccagt ctgtcgtaga    660

gacgtatcct gcaaagttgt agaaataata ctttgcattg acaaaaacgat tagtccaagc    720

ttcaccggtg tcaggatcta ggaaagattt cttgccatac ttctggctaa ttagattata    780

attgccatct gtactaatta gctttccttt gacttgaaca ccattagtgt caaaatagta    840

ttttttgccg ccaatagttc tccagccgat agcagccttt ccatcttctc caagatagaa    900

ccagccttca tgtttaatat tttcataatg gaggggatct gcataactag aatagacaaa    960

acgatccttc cagagttcac cactatcagg atcaaagtag taaatcttat tgacttccaa   1020

aactgaaggt gaatcactta tgaaaacagg atgataaatg atttgatccc ctgtctccac   1080

atgaatttct cctttgacct gactaccatc ttggttgaaa tagagctgct ttccatcaat   1140

tgtctgccaa ccggttgcca gctgtccatc ggcctttttg tagtaccatt taccatcttt   1200

ttcaaagaag ctattggttg gggcagcgtc attattttct gcagcagtcg ctggttcggt   1260

tttagccgtt tcctgctggg cagcattttc tgatggagca ttttgcactg actgagcttc   1320

tccagaaacg gctgtcgctt tttctgctgg atggtgctct tcagagtttg tttggtttgt   1380

tactgcttca gtttggctgg ctctgcctcc atcggatact tcagctgcct ctgctgtttc   1440
```

```
agaactttta acagcgttag cactgttatt ttctacagat gaatcagctg ctggagcttc   1500

tgtaactggt tgttctgagc tttcctgtac agttgctgtc agtcttggct tactgtcagt   1560

accgccgccg gattgttcct cagcctgagt caagtgagct cctgacaata tcgcagccag   1620

agctagacta gtcacggcaa tcgccatcca ctgcttttta accttgtgca gtttaaaacg   1680

tgtcttttct ttcatcat                                                 1698
```

<210> SEQ ID NO 29
<211> LENGTH: 1752
<212> TYPE: DNA
<213> ORGANISM: Streptococcus mutans

<400> SEQUENCE: 29

```
ctagttttct ttttttctag ctgcaatcaa agtagccgca gcaaatgcag ttgaaatagc     60

accaagagta gctaaaccat tttgtttagc agccccagca tgtggaagag tcggttgata    120

atcacgctct ctaacacgca tttctccttt tcttgccgtt ctaaagctta ctgacttagc    180

tacgacaggt gattgaggat cctctggtgt ttttggcttt tctggcgttg gttcatcagg    240

agttgttggt ggtgtcactg gaggaacttc ctcagtttta gtttcaacaa caagattttt    300

atgccaagtc acagtaggtt ttttcaactc tggtttttct ggcggtgttg gtttagctcc    360

cggatcttta ggcacagcta cagctgaatt agtcgcaaac caaatggttg ttggtaagtt    420

ttgatcatta ccaccaacag taaaggtgaa gggttctccc ttgtaagtca tagcacctgc    480

accataataa gccgtcgcag cacgtggcgt tccatcagca ttgacagcat cccagccatc    540

tgctccatca ccattaaagg ttgcaccatt agctttatat tggttgtcct tagccgaata    600

gatttcattg ccatgtaagt caacagatga gcccggtatt ttaacgaatt cattatcccc    660

aaggtttact ttttccacat gatcgccata cttagtcgtc caatggttta acgatgagag    720

actcataatg gcattattgc cgcttaaatc gatttcattg ccattttcat cataaaaaat    780

aatttgcatc gtcacactga ttttatcatt tctgccagca ttagatgtct gtgcaccaat    840

gaaaattgtc ttagttggat catggaacaa attgaccagt gcactgcctt cattattcgt    900

tgaactattg agagtataat taatctttac cttactaatc tttttatcat tatattttga    960

attaacgata ttatcgtagg taactgaaat ctgatctccc actttcattt tgaaccaagt   1020

atcttctttt ggatcatatg gatttgcttg ggtaaaatca gaagctgtat aattatcagt   1080

attatattgc tgaagaatat cttcagttgc atgtttttga cgtgcttctt ttgttaggta   1140

ctgattaaca ccctcaatag aaagttttgc ctcaggttca ttaataaaca caagtccttg   1200

ggctttttca acacgcccag atgccaaacc ttgtgcaact tctttttttat attgctcgta   1260

agctgccttt tgagcttcat actccttgac atcagactga tacttttcaa aatctttatt   1320

atattgttct tgtttttgag gaaattcagc ttttgccttt tgataatcag ctaccgctgt   1380

attaattgtt tgtgcctgtg ctttgttatc tgcatctgca gcttctaccg aaggctgttt   1440

ttgagcttca gtttcagtga cttctaaacc ttcctgatta gcattagcct tagcatcttc   1500

caattcttta gaagtaactt gagatgttgt cgttgttgta tttccttgtg tgtgactttc   1560

gacaacagct acaacaggag actgttcttt ttctgttgca gccggttctg atgcttgtgt   1620

atcagcagta ggtgctgcaa cagtatcaga atttaattga gttgatgctt catctgcaaa   1680

aacattcgtt gctccaaaag ccgccaaagc aaggctgctt agcaaagtaa ttttagcagt   1740

tttcgatttc at                                                       1752
```

<210> SEQ ID NO 30

<211> LENGTH: 4431
<212> TYPE: DNA
<213> ORGANISM: Streptococcus mutans

<400> SEQUENCE: 30

```
atggacaaga aagtgcgtta taaactgcgc aaagttaaaa aaagatgggt gacagtatct     60

gttgcatctg ctgtgatgac tttaactaca ctttcgggtg gcttggttaa agcagattct    120

aatgaatcga aatcccaaat ttctaatgat tctaatacta gtgttgttac tgctaatgaa    180

gaatctaatg taacaaccga agtgacatct aagcaagaag ctgctagtag tcaaactaat    240

catacagtaa cgacaatcag tagctctact tcagtagtta atcccaaaga ggttgtaagt    300

aatccttata ctgttgggga aacagcttct aatggtgaaa agcttcaaaa tcaaacaact    360

acagttgaca aaacttctga agctgctgct aataatatta gtaaacaaac aaccgaagct    420

gatacagatg ttattgatga tagcaatgca gccaatctac aaatattgga aaaacttccc    480

aatgtaaaag aaattgatgg taagtattat tattatgaca ataacggcaa agttcgtact    540

aattttacat taattgctga tggcaaaatt ttacattttg atgaaactgg cgcttatact    600

gatacatcaa ttgacactgt aaataaagat atcgtcacaa caagaagtaa tctatacaaa    660

aaatataatc aagtttatga tcgctctgca cagagctttg agcatgttga tcattatttg    720

acagccgaaa gttggtatcg tcctaagtac atcttgaagg atggcaaaac atggacacag    780

tcaacagaaa aagattttcg tcccttactg atgacatggt ggccgagcca agaaacacag    840

cgtcaatatg ttaactacat gaatgcacag cttggcatta acaagactta tgatgataca    900

agtaatcaat tgcaattaaa tattgcagct gcaactattc aagcaaaaat tgaggccaaa    960

attacaactt taaagaatac tgattggctg cgtcagacta tttccgcatt tgttaagaca   1020

cagtcagctt ggaacagtga cagcgaaaaa ccgtttgatg atcatttaca aaatggagca   1080

gtgctttacg ataatgaagg aaaattaacg ccttatgcta attccaacta ccgtatctta   1140

aatcgcaccc cgaccaatca aactgggaag aaggatccaa gatatacagc tgataacact   1200

atcggcggtt acgaattcct tttggccaac gatgtggata attccaatcc tgtcgtgcag   1260

gccgaacaat tgaactggct gcattttctc atgaactttg gcaacattta tgccaatgat   1320

ccggatgcta actttgattc cattcgtgtt gatgcggtgg ataatgtgga tgctgacttg   1380

ctccaaattg ctggggatta cctcaaagct gctaagggga tccataaaaa tgataaggct   1440

gctaatgatc atttgtctat tttagaggca tggagtgaca acgacactcc ttaccttcat   1500

gatgatggcg acaatatgat taatatggac aataagctgc gtttgtctct attattttca   1560

ttagctaaac ccttaaatca acgttcaggc atgaatcctc tgatcactaa cagtttggtg   1620

aatcgaactg atgataatgc tgaaactgcc gcagtccctt cttattcctt catccgtgcc   1680

catgacagtg aagtgcagga tttgattcgt gatatcatca aggcagaaat caatcctaat   1740

gttgtcgggt attcattcac tatggaggaa atcaagaagg ctttcgagat ttacaacaaa   1800

gacttattag ctacagagaa gaaatacaca cactataata cggcactttc ttatgccctg   1860

cttttaacca acaaatccag tgtgccgcgt gtctattatg ggatatgtt tacagatgac   1920

gggcaataca tggctcataa gacgatcaat tacgaagcca tcgaaaccct gcttaaagct   1980

cgtattaagt atgtttcagg cggtcaagcc atgcgcaatc aacaggttgg caattctgaa   2040

attattacgt ctgtccgcta tggtaaaggt gctttgaaag caacggatac aggggaccgc   2100

accacacgaa cttcaggagt ggccgtgatt gaaggcaata acccttcttt acgtttgaag   2160

gcttctgatc gcgtggttgt caatatggga gcagcccata agaaccaagc ttaccgacct   2220
```

```
ttactcttga ccacagataa cggtatcaag gcttatcatt ccgatcaaga agcggctggt   2280

ttggtgcgct acaccaatga cagaggggaa ttgatcttca cagcggctga tattaaaggc   2340

tatgccaacc ctcaagtttc tggctattta ggtgtttggg ttccagtagg cgctgccgct   2400

gatcaagatg ttcgcgttgc ggctagcacg gccccatcaa cagatggcaa gtctgtgcat   2460

caaaatgcgg cccttgattc acgcgtcatg tttgaaggtt tctctaattt ccaagctttc   2520

gccactaaaa aagaggaata taccaatgtt gtgattgcta agaatgtgga taagtttgcg   2580

gaatggggtg tcacagattt tgaaatggca ccgcagtatg tgtcttcaac agatggttct   2640

ttcttggatt ctgtgatcca aaacggctat gcttttacgg accgttatga cttaggaatt   2700

tccaaaccta ataaatacgg gacagccgat gatttggtga aagccatcaa agcgttacac   2760

agcaagggca ttaaggtaat ggctgactgg gtgcctgatc aaatgtatgc ttttcctgaa   2820

aaagaagtgg taacagcaac ccgtgttgat aagtttggaa aaccggttga aggctcacaa   2880

attaagagtg ttctttatgt tgctgacagt aagagttctg gtaaagatca acaagccaag   2940

tatgggggag ctttcttaga ggagctgcaa gcgaagtatc cggagctttt tgcgagaaaa   3000

caaatttcca caggggttcc gatggatcct tctgttaaga ttaagcaatg gtctgccaag   3060

tactttaatg ggacaaatat tttagggcgc ggagcaggct atgtcttaaa agatcaggca   3120

actaatactt actttaatat ttcagataat aaagaaataa acttccttcc taaaacattg   3180

ttaaaccaag atagtcaagt tggtttctct tatgacggta aaggttatgt ttattattca   3240

acgagtggtt accaagccaa aaatactttc atcagcgaag gtgataaatg gtattatttt   3300

gataataacg gttatatggt cactggtgct caatcaatta acggtgttaa ttattatttc   3360

ttatcaaatg gtctacagct cagagatgct attcttaaga atgaagatgg aacttacgct   3420

tattatggaa atgacggtcg ccgttatgaa aatggttatt atcaattcat gagtggtgta   3480

tggcgtcact tcaataatgg tgaaatgagt gttggattaa ctgtaattga tggtcaggtt   3540

caatactttg atgaaatggg ctatcaagcc aaaggaaaat ttgtaacaac tgccgatggt   3600

aaaataagat attttgataa gcaatctggg aacatgtatc gtaatcgttt tattgaaaac   3660

gaagaaggta aatggctgta tctcggtgaa gatggtgcag cagtgacagg atctcaaacc   3720

attaacggtc aacacctgta ctttagagca aacggtgttc aggtcaaggg tgaatttgtc   3780

actgaccgct acggccgtat cagctattac gacagcaatt caggggatca aatccgcaac   3840

cgctttgtcc gcaatgctca gggtcagtgg ttctactttg ataacaatgg ctatgccgta   3900

accggtgcca gaaccattaa cggtcaacac ctatacttta gagcaaacgg tgttcaggtc   3960

aagggtgaat ttgtcactga ccgccacggt cgtatcagct attacgacgg caattcaggg   4020

gatcaaatcc gcaaccgctt tgtccgcaat gctcagggtc aatggttcta ctttgataac   4080

aatggctatg ccgtaaccgg tgccagaacc attaacggtc aacacctata ctttagagca   4140

aacggtgttc aggtcaaggg tgaatttgtc actgaccgct acggccgtat cagctattac   4200

gacagcaatt caggggatca aatccgcaac cgctttgtcc gcaatgctca gggtcagtgg   4260

ttctactttg ataacaatgg ctatgccgta accggtgcca gaaccattaa cggtcaacac   4320

ctgtacttta gagcaaacgg tgttcaggtc aaaggtgaat ttgtcactga ccgctacggc   4380

cgtatcagtt attacgatgc taactctgga gaacgagttc ggattaacta a            4431
```

<210> SEQ ID NO 31
<211> LENGTH: 4389
<212> TYPE: DNA
<213> ORGANISM: Streptococcus mutans

<400> SEQUENCE: 31

```
atggaaacca aacgacgtta caaaatgtac aaggttaaaa agcactgggt aaccattgct     60
gtcgcttctg gtttgattac cttgggcacc acaacactgg gaagctcagt ttcagcagaa    120
acagaacagc agacctcaga taaagtggta actcagaaaa gtgaggatga taaggcggca    180
tctgaatcca gccaaacaga tgcacctaaa actaagcaag cacaaacaga acaaacgcag    240
gcccaaagtc aggcaaacgt tgctgataca agcactagca taactaagga aactccttca    300
caaaatatta caacacaagc caactctgat gacaaaacag taacaaatac gaaatcagaa    360
gaagcacaaa cttctgaaga gcgcacaaag caagcagaag aagcacaggc tactgcttcc    420
agtcaggctt taacacaggc aaaagctgaa ttaacaaagc aaagacaaac agcagctcaa    480
gaaaataaaa atcctgttga cttagcggcc attccaaatg tgaaacaaat tgatggcaaa    540
tattattata ttggttctga tggtcagcct aagaaaaatt ttgctctaac cgttaataac    600
aaagtactct acttcgataa aaatacaggt gccttaacgg acacttctca gtatcaattt    660
aaacaagggt taacaaaatt aaacaacgat tatactcccc acaatcaaat tgtcaatttt    720
gaaaatacca gtcttgaaac gattgataac tatgtcacag ctgattcgtg gtatcgtcct    780
aaggatattt taaagaatgg caaaacgtgg acagcttcat ctgagtctga tcttcgtccg    840
cttttaatgt cttggtggcc agataaacaa acgcaaattg cttatcttaa ctacatgaac    900
cagcaaggac ttggaactgg tgaaaattac acagcagaca gcagccaaga aagtctcaac    960
cttgctgcac aaaccgttca agttaagatt gaaactaaaa tttctcaaac gcagcaaacc   1020
cagtggctgc gtgatattat caatagtttt gttaaaacgc aaccaaattg gaatagtcaa   1080
acagaatcgg atacttcagc tggtgaaaaa gatcacttgc aaggcggtgc tctgctttac   1140
agcaacagcg ataagacagc ctatgctaat tccgattacc gtcttttgaa ccgcacacca   1200
accagtcaaa cgggtaaacc aaaatatttt gaagacaatt cttctggtgg ctatgacttc   1260
ctcctagcta atgatattga taattcaaat ccagtggttc aagctgaaca attaaactgg   1320
cttcattatc tgatgaatta tggttctatt gtcgctaatg atcctgaggc taattttgac   1380
ggtgttcgtg ttgatgccgt tgataatgtt aatgccgact tgctgcagat tgcttcggac   1440
tatttgaaag cccattatgg tgttgataag agtgagaaaa atgcgattaa tcatctttcc   1500
attttagaag cttggtcaga taatgatccc caatacaata aagatactaa gggtgcacaa   1560
ttaccgattg ataataaact gcgcctatcg cttttatatg ctttgacgcg tcctcttgaa   1620
aaagatgcaa gcaataaaaa tgaaattcgc agcggacttg agcctgtcat aacaaatagc   1680
ttgaataacc gttcagctga aggtaaaaat agtgaacgta tggctaacta tatttttatc   1740
cgcgctcacg acagtgaagt ccaaacggtt attgctaaaa ttattaaagc tcagattaat   1800
cccaaaacag atggtttgac ctttactttg gatgaattga agcaagcctt taagatctac   1860
aatgaagaca tgcgtcaggc taagaaaaag tacacacaat ccaatattcc gacagcctat   1920
gctttgatgc tgtccaataa agattcaatt acacgtcttt attatggtga tatgtacagt   1980
gatgacggtc aatatatggc gactaaatcc ccttattatg atgctattga tactttatta   2040
aaggcacgta ttaaatatgc cgccggtggt caagacatga agatcaccta tgttgaaggt   2100
gataaaagtc atatggattg ggattataca ggcgttttga cttctgttcg ttatggtaca   2160
ggagctaatg aagctacaga tcaaggcagt gaagcaacca aaacacaagg aatggctgtc   2220
attaccagca ataaccctag ccttaaattg aatcaaaatg ataaagtaat tgtcaatatg   2280
gggactgcgc ataaaaatca agagtaccgt ccgctcctct taacaactaa agatggtttg   2340
```

```
acaagctaca cttctgatgc cgctgctaaa tccctttatc gcaaaacgaa tgataaagga   2400

gaattagtct ttgatgctag tgacattcaa ggttacctga atccgcaagt atcaggttat   2460

ttagccgttt gggttccagt aggagctagt gataatcaag atgttcgtgt agcagcaagc   2520

aataaggcaa atgctactgg tcaagtctac gaatcatcaa gtgctcttga ttctcaattg   2580

atttatgaag gcttctcaaa cttccaagat tttgtgacga aagattcaga ctatactaat   2640

aagaagattg ctcaaaatgt ccaactcttc aaatcttggg gtgtcacttc ctttgaaatg   2700

gcaccgcaat atgtctcttc tgaagatggt tcttttctag actctattat tcaaaatggt   2760

tatgcctttg aggatcgtta tgatcttgct atgagtaaga ataacaaata cggttctcag   2820

caagacatga ttaatgcagt taaagctctg cataaaagcg gtattcaggt tattgcggat   2880

tgggtaccag atcaaatcta taatcttccg ggcaaagaag tcgtaacggc tacacgtgtc   2940

aacgattatg gtgagtatcg caaagactct gaaatcaaaa atacactcta tgctgccaac   3000

actaagagta atggtaagga ttatcaagcg aagtatggcg gtgctttcct tagtgaactc   3060

gctgctaagt accctagtat ctttaaccgc acacaaattt caaatggtaa gaagattgat   3120

ccaagcgaaa aaatcacagc atggaaagca aaatacttca atgggacaaa tattctaggc   3180

cgtggtgttg gttatgttct taaagataat gctagtgata aatactttga actgaaaggg   3240

aatcaaacct atctgccaaa acagatgact aacaaagaag cttcgactgg ttttgttaat   3300

gatggcaatg ggatgacttt ctattcaact agtggttatc aagccaagaa cagctttgtt   3360

caagatgcca aaggaaactg gtattacttt gataataatg gccatatggt ttatggcttg   3420

cagcatctaa atggcgaagt gcaatacttt ttatcaaatg gtgttcaatt gcgtgaatct   3480

ttcttggaaa acgctgatgg cagcaagaac tattttggtc atctaggaaa tagatatagt   3540

aatggttatt attcatttga taatgatagt aagtggcgtt attttgatgc cagtggagtc   3600

atggctgtag gtttgaaaac aattaacggc aatacgcagt actttgatca agatggttat   3660

caagtcaaag gtgcttggat aacaggcagc gatggcaaaa agcgttattt tgatgacgga   3720

tctggaaata tggctgttaa tcgttttgca aatgataaaa acggcgattg gtactatctc   3780

aattcagatg gcattgcctt ggttggtgtc caaaccatta atggtaagac ttattacttt   3840

ggccaagatg gtaagcaaat caaaggtaaa attattacag acaatggtaa gctgaaatat   3900

ttccttgcca attcaggaga attagcacgc aatatctttg caacagacag tcaaaacaat   3960

tggtattact ttggttcaga cggtgttgcg gttacaggca gtcagacaat tgctggtaaa   4020

aagctctatt ttgcaagcga cggaaaacaa gtcaaaggca gctttgtcac tttataatggt   4080

aaagttcatt attatcatgc tgactcagga gaattacaag ttaaccgctt tgaagcagat   4140

aaggatggta attggtatta tcttgattca aatggtgaag ctctgacagg cagccaacgc   4200

attaacggtc agcgtgtctt ctttacgcga gaaggaaaac aagttaaagg tgatgttgct   4260

tatgatgagc gagggcttct tcgttattat gataagaata gtggtaacat ggtttacaac   4320

aaagtcgtca ctttagccaa tggaagacgt attggcattg accgttgggg tatcgctaga   4380

tattattaa                                                            4389
```

<210> SEQ ID NO 32
<211> LENGTH: 4389
<212> TYPE: DNA
<213> ORGANISM: Streptococcus mutans

<400> SEQUENCE: 32

```
atggaaacca aacgacgtta caaaatgtac aaggttaaaa agcactgggt aaccattgct     60
```

-continued

```
gtcgcttctg gtttgattac cttgggcacc acaacactgg gaagctcagt ttcagcagaa    120
acagaacagc agacctcaga taaagtggta actcagaaaa gtgaggatga taaggcggca    180
tctgaatcca gccaaacaga tgcacctaaa actaagcaag cacaaacaga acaaacgcag    240
gcccaaagtc aggcaaacgt tgctgataca agcactagca taactaagga aactccttca    300
caaaatatta caacacaagc caactctgat gacaaaacag taacaaatac gaaatcagaa    360
gaagcacaaa cttctgaaga gcgcacaaag caagcagaag aagcacaggc tactgcttcc    420
agtcaggctt taacacaggc aaaagctgaa ttaacaaagc aaagacaaac agcagctcaa    480
gaaaataaaa atcctgttga cttagcggcc attccaaatg tgaaacaaat tgatggcaaa    540
tattattata ttggttctga tggtcagcct aagaaaaatt ttgctctaac cgttaataac    600
aaagtactct acttcgataa aaatacaggt gccttaacgg acacttctca gtatcaattt    660
aaacaagggt taacaaaatt aaacaacgat tatactcccc acaatcaaat tgtcaatttt    720
gaaaatacca gtcttgaaac gattgataac tatgtcacag ctgattcgtg gtatcgtcct    780
aaggatattt taaagaatgg caaaacgtgg acagcttcat ctgagtctga tcttcgtccg    840
cttttaatgt cttggtggcc agataaacaa acgcaaattg cttatcttaa ctacatgaac    900
cagcaaggac ttggaactgg tgaaaattac acagcagaca gcagccaaga aagtctcaac    960
cttgctgcac aaaccgttca agttaagatt gaaactaaaa tttctcaaac gcagcaaacc   1020
cagtggctgc gtgatattat caatagtttt gttaaaacgc aaccaaattg gaatagtcaa   1080
acagaatcgg atacttcagc tggtgaaaaa gatcacttgc aaggcggtgc tctgctttac   1140
agcaacagcg ataagacagc ctatgctaat tccgattacc gtcttttgaa ccgcacacca   1200
accagtcaaa cgggtaaacc aaaatatttt gaagacaatt cttctggtgg ctatgacttc   1260
ctcctagcta atgatattga taattcaaat ccagtggttc aagctgaaca attaaactgg   1320
cttcattatc tgatgaatta tggttctatt gtcgctaatg atcctgaggc taattttgac   1380
ggtgttcgtg ttgatgccgt tgataatgtt aatgccgact tgctgcagat tgcttcggac   1440
tatttgaaag cccattatgg tgttgataag agtgagaaaa atgcgattaa tcatctttcc   1500
attttagaag cttggtcaga taatgatccc caatacaata aagatactaa gggtgcacaa   1560
ttaccgattg ataataaact gcgcctatcg cttttatatg ctttgacgcg tcctcttgaa   1620
aaagatgcaa gcaataaaaa tgaaattcgc agcggacttg agcctgtcat aacaaatagc   1680
ttgaataacc gttcagctga aggtaaaaat agtgaacgta tggctaacta tatttttatc   1740
cgcgctcacg acagtgaagt ccaaacggtt attgctaaaa ttattaaagc tcagattaat   1800
cccaaaacag atggtttgac ctttactttg gatgaattga agcaagcctt taagatctac   1860
aatgaagaca tgcgtcaggc taagaaaaag tacacacaat ccaatattcc gacagcctat   1920
gctttgatgc tgtccaataa agattcaatt acacgtcttt attatggtga tatgtacagt   1980
gatgacggtc aatatatggc gactaaatcc ccttattatg atgctattga tactttatta   2040
aaggcacgta ttaaatatgc cgccggtggt caagacatga agatcaccta tgttgaaggt   2100
gataaaagtc atatggattg ggattataca ggcgttttga cttctgttcg ttatggtaca   2160
ggagctaatg aagctacaga tcaaggcagt gaagcaacca aaacacaagg aatggctgtc   2220
attaccagca ataaccctag ccttaaattg aatcaaaatg ataaagtaat tgtcaatatg   2280
gggactgcgc ataaaaatca agagtaccgt ccgctcctct taacaactaa agatggtttg   2340
acaagctaca cttctgatgc cgctgctaaa tccctttatc gcaaaacgaa tgataaagga   2400
gaattagtct ttgatgctag tgacattcaa ggttacctga atccgcaagt atcaggttat   2460
```

```
ttagccgttt gggttccagt aggagctagt gataatcaag atgttcgtgt agcagcaagc   2520
aataaggcaa atgctactgg tcaagtctac gaatcatcaa gtgctcttga ttctcaattg   2580
atttatgaag gcttctcaaa cttccaagat tttgtgacga aagattcaga ctatactaat   2640
aagaagattg ctcaaaatgt ccaactcttc aaatcttggg gtgtcacttc ctttgaaatg   2700
gcaccgcaat atgtctcttc tgaagatggt tcttttctag actctattat tcaaaatggt   2760
tatgcctttg aggatcgtta tgatcttgct atgagtaaga ataacaaata cggttctcag   2820
caagacatga ttaatgcagt taaagctctg cataaaagcg gtattcaggt tattgcggat   2880
tgggtaccag atcaaatcta taatcttccg ggcaaagaag tcgtaacggc tacacgtgtc   2940
aacgattatg gtgagtatcg caaagactct gaaatcaaaa atacactcta tgctgccaac   3000
actaagagta atggtaagga ttatcaagcg aagtatggcg gtgctttcct tagtgaactc   3060
gctgctaagt accctagtat ctttaaccgc acacaaattt caaatggtaa gaagattgat   3120
ccaagcgaaa aaatcacagc atggaaagca aaatacttca atgggacaaa tattctaggc   3180
cgtggtgttg gttatgttct taaagataat gctagtgata aatactttga actgaaaggg   3240
aatcaaacct atctgccaaa acagatgact aacaaagaag cttcgactgg ttttgttaat   3300
gatggcaatg ggatgacttt ctattcaact agtggttatc aagccaagaa cagctttgtt   3360
caagatgcca aaggaaactg gtattacttt gataataatg gccatatggt ttatggcttg   3420
cagcatctaa atggcgaagt gcaatacttt ttatcaaatg gtgttcaatt gcgtgaatct   3480
ttcttggaaa acgctgatgg cagcaagaac tattttggtc atctaggaaa tagatatagt   3540
aatggttatt attcatttga taatgatagt aagtggcgtt attttgatgc cagtggagtc   3600
atggctgtag gtttgaaaac aattaacggc aatacgcagt actttgatca agatggttat   3660
caagtcaaag gtgcttggat aacaggcagc gatggcaaaa agcgttattt tgatgacgga   3720
tctggaaata tggctgttaa tcgttttgca aatgataaaa acggcgattg gtactatctc   3780
aattcagatg gcattgcctt ggttggtgtc caaaccatta atggtaagac ttattacttt   3840
ggccaagatg gtaagcaaat caaaggtaaa attattacag acaatggtaa gctgaaatat   3900
ttccttgcca attcaggaga attagcacgc aatatctttg caacagacag tcaaaacaat   3960
tggtattact ttggttcaga cggtgttgcg gttacaggca gtcagacaat tgctggtaaa   4020
aagctctatt ttgcaagcga cggaaaacaa gtcaaaggca gctttgtcac ttataatggt   4080
aaagttcatt attatcatgc tgactcagga gaattacaag ttaaccgctt tgaagcagat   4140
aaggatggta attggtatta tcttgattca aatggtgaag ctctgacagg cagccaacgc   4200
attaacggtc agcgtgtctt ctttacgcga gaaggaaaac aagttaaagg tgatgttgct   4260
tatgatgagc gagggcttct tcgttattat gataagaata gtggtaacat ggtttacaac   4320
aaagtcgtca ctttagccaa tggaagacgt attggcattg accgttgggg tatcgctaga   4380
tattattaa                                                           4389
```

<210> SEQ ID NO 33
<211> LENGTH: 1968
<212> TYPE: DNA
<213> ORGANISM: Streptococcus mutans

<400> SEQUENCE: 33

```
ccggctataa gttgaaatat tgtaggtatt aaaaactatc tttagtttag tatttacatt     60
aattttaaaa atgttatagt ggaagtgtca tgttgattac tattttttta aggaggtaaa    120
atgatgaaag aaaagacacg ttttaaactg cacaaggtta aaaagcagtg ggtggcgatt    180
```

```
gccgtgacta gtctagctct agctgcgata ttgtcaggag ctcacttgac tcaggctgag    240
gaacaatccg gcggtactga cagtaagcca agactgacag cgactgtaca ggaaagctca    300
gaacaaccaa ttacaaaagc tccagcagct gattcatctg tagaaaataa cagtgctaac    360
gctgttaaaa gttctgaaac agcagaggca gctgaagtat ccgatggagg cagagccagc    420
caaactgaag cagtaacaaa ccaaacaaac tctgaagagc accatccagc agaaaaagcg    480
acagccgttt ctggagaagc tcagtcagtg caaaatgctc catcagaaaa tgctgcccag    540
caggaaacgg ctaaaaccga gccagcgact gctgcagaaa ataatgacgc tgctccaacc    600
aatagcttct ttaaaaaaga tggtaaatgg tactacaaaa aggccgatgg acagctggca    660
accggttggc agataattga tggaaagcag ctctatttca accaagatgg tagtcaggtc    720
aaaggagaaa ttcatgtgga gacaggggat caaatcattt atcatcctgt tttcataagt    780
gattcacctt cagttttgga agtcaataag atttattact ttgatcctga tagtggtgaa    840
ctctggaagg atcgttttgt ctattctagt tatgcagatc ccctccatta tgaaaatatt    900
aaacatgaag gctggttcta tcttggagaa gatggaaagg ctgctatcgg ctggagaact    960
attggcggta aaaaatacta ttttgacact aatggtgttc aagtcaaagg aaagctaatt   1020
agtacagatg gcaattataa tctaattagc cagaagtatg gcaagaaatc tttcctagat   1080
cctgacaccg gtgaagcttg gactaatcgt tttgtcaatg caaagtatta tttctacaac   1140
tttgcaggat acgtctctac gacagactgg ttctatatgg gagccgatgg tatcggcgtg   1200
accgattggc aaaagatcga tggtatggat tactatttcg aaccttccag tggtattcag   1260
gttaaaggcg acattgctga gcgtgatggc aaggtctatt atttagatga agacagtgga   1320
caagttgtta agaatcgttt tggcacaaca cctgccgagc gtatcagtac agttgaggct   1380
cgtttcccta aaacttatta ttttggagcg gacggtagcc gcaaagatct aactggttgg   1440
cagattattg atggtaaaac ttattacttt aaggatgatc acagcataaa agcaaagtca   1500
gagtatagtc aaattggtgg ttctgtgcct gatgacggtt ttgcagagat tgatggtgat   1560
ggttactttt ttgatactca aggtcaattc gtaacgaata gatttgtcag aaaatacgac   1620
tacagtaata tttggtatta ttatggaagc gatggcaaac gtgtatcagg ctggcaaact   1680
atcgacggta agcgctacta ctttagccaa gatgaaaaga caaagggccg tcaaattaaa   1740
ggacaaacca tcactatcga tggtaaagaa tatacttttg acaaagacag cggtgaagtt   1800
atcaatagta actagttggt aaatcccatg gcacacaaaa acgagcagat ttcatactct   1860
gttcgttttt tcgccttaaa acttatatat ttataaatcg tcaataaagt gtttacttga   1920
aaacggtaaa tatgccaaga gtttgactgt tatcaattaa tgggaaag                 1968
```

<210> SEQ ID NO 34
<211> LENGTH: 1950
<212> TYPE: DNA
<213> ORGANISM: Streptococcus mutans

<400> SEQUENCE: 34

```
ctgtgatgac ttcactagct actttgctat aatccatttg caaaaaactc cttaataatt     60
attttgtttt gaaagcgttt ttttactttc cacgttattc attttatcat tttttccaat    120
atgtcaatcg ttttacataa aattcttttt tgcaacaaaa gattgatttt tagaaagaaa    180
acgtttacta tattagtatg tagataaact attattagga gtagataaac gatgaatttg    240
cctcaaaata tcagatatcg ccgctatcaa gattggactg aagaagaaat aaaaagtatt    300
aaaaccaatg tagctttgtc tccttggcat acaacgtatc atatagaacc taaaacagga    360
```

ctccttaatg atccaaacgg tttttcctat tttaatggaa aatttaacct tttttatcaa 420
aattggccat ttggagcagc tcacggctta aaatcttgga tccatactga aagtgaagac 480
ttagtccatt tcaaagaaac aggtacagtc ctttatcccg atacttccca tgacagccat 540
ggtgcatact cgggcagtgc ctatgaaatc ggtgatcagc tttttctctt ttatacagga 600
aatgtccgag atgaaaattg ggttcgtcat ccacttcaaa tcggcgcttt tatggataaa 660
aaaggtaata tccaaaaatt tactgatgtc cttattaaac agccaaatga tgttactgaa 720
cactttcgcg atccccaaat ttttaattat aaaggacaat tttatgctat tgttggagca 780
caaagtctag actttggcgg aagtaaatct gagtatatga ttgagtgccc aaatcttgtt 840
tttataaacg aacagcctgt cctgatttat agtcctcagg gactcagtaa atctgaatta 900
gattatcata atatttatcc taatacttac aaagtatgtc aatcgtttga cacagaaaag 960
cctgccctag ttgatgcatc ggaaattcaa aatcttgact tcggatttga atgttatgct 1020
acccaagctt tcaatgctcc tgatggccgt gtttatgctg tctcatggat tgggttacca 1080
gatattgatt atccaagtga ttcatacgac tatcaaggag ctttgagcct cgtcaaagag 1140
ctaagcctta aacacggtaa actctatcaa tatcccgttg aagctgttcg ttcattacgt 1200
tctgaaaaag aagcagtcac ttacaagcca gaaaccaata atacttatga attagagtta 1260
acttttgact cttcatcagt taatgaattg ctcctttttg ctgataataa aggcaatggt 1320
ctagctatta cagttgatac taagatggga accattctga tcgatcgctc taaagcaggg 1380
gagcaatatg ccttagaatt tggaagccaa cgttcttgct ctatccaagc aaaagagact 1440
gttgtcaata tttttgttga caaatctatt tttgaaattt ttattaataa gggagaaaaa 1500
gtttttactg gacgtgtttt tccaaatgac aaacaaactg gtattgtgat taaatctgga 1560
aagccaagcg gtaattacta cgaattgaaa tattaactat ggttgcaaaa ttaacagatg 1620
tcgcaaaact cgctggcgta agtccaacaa ccgtttcacg cgtgattaat cgaaaaggct 1680
atctctctga aaaaacaatt actaaagtac aggctgccat gaaaactcta ggatacaagc 1740
ccaataatct cgctcgcagc cttcagggga aatctgccaa gctaattgga cttattttcc 1800
ctaatatcag tcacatcttc tattctgaac ttattgaata tttagaaata gagttgttta 1860
aacatggcta caaagccatt atttgtaaca gtcagaataa tcccgataaa gaacgggatt 1920
atctcgaaat gttagaagct aatcaggttg 1950

<210> SEQ ID NO 35
<211> LENGTH: 5212
<212> TYPE: DNA
<213> ORGANISM: Streptococcus mutans

<400> SEQUENCE: 35 tttttgtgc tttagaatta atgttggata aagtgtggag tttgtgctcg aaaaatagca 60
gcgattgaat gtgtttataa tttgattcag acattagttt ttatttcaag caaaaaattt 120
gacaaatcaa atcaattata ttacaatttt ttaacgtata ttacaaaaat atatttggaa 180
gatttattca gatttggagg atttatgaaa gtcaaaaaaa cttacggttt tcgtaaaagt 240
aaaattagta aaacactgtg tggtgctgtt ctaggaacag tagcagcagt ctctgtagca 300
ggacaaaagg tttttgccga tgaaacgacc actactagtg atgtagatac taaagtagtt 360
ggaacacaaa ctggaaatcc agcgaccaat ttgccagagc gtcaagggag tgcgagtaag 420
gaagctgaac aaagtcaaaa ccaagctgga gagacaaatg gttcaatacc agttgaagta 480
cctaaaactg atcttgatca agcagcaaaa gatgctaagt ctgctggtgt caatgttgtc 540

-continued

```
caagatgccg atgttaataa aggaactgtt aaaacagctg aagaagcagt ccaaaaagaa    600

actgaaatta aagaagatta cacaaaacaa gctgaggata ttaagaagac aacagatcaa    660

tataaatcgg atgtagttgc tcatgaggca gaagttgcta aaatcaaagc taaaaatcag    720

gcaactaaag aacagtatga aaaagatatg gcagctcata aagccgaggt tgaacgcatt    780

aatgctgcaa atgctgccag taaaacagct tatgaagcta aattggctca atatcaagca    840

gatttagcag ccgttcaaaa aaccaatgct gccaatcaag cagcctatca aaaagccctt    900

gctgcttatc aggctgaact gaaacgtgtt caggaagcta atgcagccgc caaagccgct    960

tatgatactg ctgtagcagc aaataatgct aaaaatacag aaattgccgc tgccaatgaa   1020

gaaattagaa aacgcatggc aacggccaaa gctgaatatg agactaagtt agctcaatat   1080

caagctgaac taaagcgtgt tcaggaagct aatgccgcaa acgaagcaga ctatcaagct   1140

aaattgaccg cctatcaaac agagcttgct cgcgttcaaa aagctaatgc ggatgctaaa   1200

gcggcctatg aagcagctgt agcagcaaat aatgccaaaa atgcggcact cacagctgaa   1260

aatactgcaa ttaagcaacg caatgagaat gctaaggcga cttatgaagc tgcactcaag   1320

caatatgagg ccgatttggc agcggtgaaa aaagctaatg ccgcaaacga agcagactat   1380

caagctaaat tgaccgccta tcaaacagag ctcgctcgcg ttcaaaaagc caatgcggat   1440

gctaaagcgg cctatgaagc agctgtagca gcaaataatg ccgcaaatgc agcgctcaca   1500

gctgaaaata ctgcaattaa aaagcgcaat gcggatgcta aagctgatta cgaagcaaaa   1560

cttgctaagt atcaagcaga tcttgccaaa tatcaaaaag atttagacga ctatccagtt   1620

aagttaaagg acatgcaaga tgaacaagct tctattaaac gtcgactggc agaacttgaa   1680

aaacataaaa atgaagacgg aaacttaaca gaaccatctg ctcaaaattt ggtctatgat   1740

cttgagccaa atgcgaactt atctttgaca acagatggga agttccttaa ggcttctgct   1800

gtggatgatg cttttagcaa aagcacttca aaagcaaaat atgtccaaaa aattcttcaa   1860

ttagatgatc tagatatcac taacttagaa caatctaatg atgttgcttc ttctatggag   1920

ctttatggga attttggtga taaagctggc tggtcaacga cagtaagcaa taactcacag   1980

gttaaatggg gatcggtact tttagagcgc ggtcaaagcg caacagctac atacactaac   2040

ctgcagaatt cttattacaa tggtaaaaag atttctaaaa ttgtctacaa gtatacagtg   2100

gaccctaagt ccaagtttca aggtcaaaag gtttggttag gtatttttac cgatccaact   2160

ttaggtgttt ttgcttccgc ttatacaggt caagttgaaa aaaacacttc tatttttatt   2220

aaaaatgaat tcactttcta tgacgaagat ggaaaaccaa ttaattttga taatgccctt   2280

ctctcagtag cttctcttaa ccgtgaacat aactctattg agatggccaa agattatagt   2340

ggtaaatttg tcaaaatctc tggttcatct attggtgaaa agaatggcat gatttatgct   2400

acagatactc ttaactttaa acagggtgaa ggtggctctc gctggactat gtataaaaat   2460

agtcaagctg gttcaggatg ggatagttca gatgcgccga attcttggta tggagcaggg   2520

gctattaaaa tgtctggtcc gaataaccat gttactgtag gagcaacttc tgcaacaaat   2580

gtgatgccag tttctgacat gcctgttgtt cctggtaagg acaatactga tggcaaaaaa   2640

ccaaatattt ggtattcttt aaatggtaaa atccgtgcgg ttaatgttcc taaagttacc   2700

aaggaaaaac ccacaccgcc ggttaaacca acagctccaa ctaaaccaac ttatgaaaca   2760

gaaaagccat taaaaccggc accagtagct ccaaattatg aaaaggagcc aacaccgccg   2820

acaaggacac cggatcaacg agagccaaac aaacccacac cgccgaccta tgaaacagaa   2880

aagccgttgg agccagcacc tgttgagcca agctatgaag cagagccaac accgccgaca   2940
```

```
aggacaccgg atcagcagag ccaaataaac ccacaccgcc agacctatga aacagaaaag   3000
ccgttggagc cagcacctgt tgagccaagc tatgaagcag agccaacgcc accgacacca   3060
acaccagatc aaccagaacc aaacaaacct gttgagccaa cttatgaggt tattccaaca   3120
ccgccgactg atcctgttta tcaagatctt ccaacacctc catctgtacc aactgttcat   3180
ttccattact ttaaactagc tgttcagccg caggttaaca aagaaattag aaacaataac   3240
gatgttaata ttgacagaac tttggtggct aaacaatctg ttgttaagtt ccagctgaag   3300
acagcagatc tccctgctgg acgtgatgaa acaacttcct ttgtcttggt agatcccctg   3360
ccatctggtt atcaatttaa tcctgaagct acaaaagctg ccagccctgg ctttgatgtc   3420
acttatgata atgcaactaa tacagtcacc ttcaaggcaa ctgcagcaac tttggctacg   3480
tttaatgctg atttgactaa gtcagtggca acagtttatc caacagtggt cggacaagtt   3540
cttaatgatg gcgcaactta taagaataat ttcacgctca cagtcaatga tgcttatggc   3600
attaaatcca atgttgttcg ggtgacaact ctggtaaacc aaatgatcca gataacccaa   3660
ataataatta cattagcaac taaggttata aaaatgaaaa tggcgttgtt attgatggga   3720
aaagaccttc ttgccggttc aacgaattat tatgaactaa cttgggattt ggatcatata   3780
aaacgaccgt cttcagcaga taccattcaa aggatttact atgtagatga ttatccagaa   3840
gaagacgact tgaagattga cgatcaggat ttagatgaag attacagaat gctaatggta   3900
atgaagttac tggtgttagt gtggataatt atactagtct tgaagcagcc cctcaagaaa   3960
ttagagatgt tctttctaag ggcaggaatt agactaaagg gtgctttcca aattttccgt   4020
gccgataatc caagagaatt ttatgatact tatgtcaaaa ctggaattga tttgaagatt   4080
gtatcaccaa tggttgttaa aacaatggga caaacaggcg gtagttatga aaatcaagct   4140
taccaaattg actttggtaa tggttatcga tcaaatatcg ttatcaataa atggcttcct   4200
aagattaacc ctaagaagga tatgacctta acacttgatc cggctgatac aaataaatgc   4260
gttgatggtc agactattcc acttaataca gtctttaatt accgtttgat tgggtggcat   4320
ttatccctgc aaatcactca gaagaactct ttgaatacaa tttctatgat gattatgatc   4380
aaacaggaga tcactatact ggtcagtata aagtttttgg ccaaggttga tatcactttt   4440
aaagacggtt ctattatcaa gtcaggtgct gagttaactc agtatacgac agcggaagtt   4500
gataccgcta aaggtgctat cacaattaag ttcaaggaag cctttctgcg ttctgtttca   4560
attgattcag ccttccaagc tgaaagttat atccaaatga aacgtattgc ggttggtact   4620
tttgaaaata cttatattaa tactgtcaat ggggtaactt acagttcaaa tacagtgaag   4680
acaactactc ctgaggatcc tacagaccct actgatccgc aagatccatc atcaccgcgg   4740
acttcaactg taattaacta taaacctcaa tcaactgctt atcaaccaag ctctgttcaa   4800
gaaacattac caaatacggg agtaacaaac caatgcttat atgcctttac ttggtattat   4860
tggcttagtt actagtttta gtttgcttgg tttaaaggct aagaaagatt gacagccatt   4920
agaccattta ccattagaat taaaaagtga gatagaagcg ataaatcaca gattgagctt   4980
ttatctcatt ttttgattaa ttaaaagaga aataactagc ctatctttgt tctattaaaa   5040
aaacagttag tcttaaatag gaatatcatt aaccaatttt tgaaaacgat catttagtgt   5100
gagtttttaa ctatctttct taaagaaaaa atgctataat gttttagttg cacattacta   5160
acgtttgata aggtacgttc gcactgcctt ttagaaagag aaaacattga aa           5212
```

<210> SEQ ID NO 36
<211> LENGTH: 3137
<212> TYPE: DNA

<213> ORGANISM: Streptococcus mutans

<400> SEQUENCE: 36

```
gaattctttt tggcataaac tcaccccaat caattatttt atataatatt ataaataatt     60
atttagatat agtcaattag ttaaagatat aaaataaaat taatcagtca attattttat    120
atctttaaga tttatggtgt tgcttgttgt agttgttgag tattgatgtg aaataattgt    180
gcataaaacc ttcaaaacaa aattttatga tacaaagata agcgaaaaat tatagaaata    240
ttaaaataac aaaataataa caattgaaga cttcttgtta aaaacagtat ttttatgtta    300
aaatgtagat gtagatataa caattcaaaa tattctacag attaactaag gagaaaattc    360
tattatgaaa atgaaacgta aactattaag cttggtttca gtccttacta ttttattggg    420
agctttttgg gtaacgaaga ttgtaaaagc tgaccaagtc acaaattata caaatacggc    480
ttctatcaca aaatcagatg gtacagcact ttctaatgat ccatctaagg ctgttaatta    540
ttgggaacca ctttctttca gtaattctat tactttccca gatgaagtca gtattaaggc    600
tggggatact ttaaccatta agttgccaga gcaattacaa tttacgactg ctctaacttt    660
cgatgttatg cataccaatg ggcaattagc tggtaaagca acaactgatc ctaatacagg    720
agaagtaaca gttaccttta ctgatatttt tgaaaaactg cctaatgata aggctatgac    780
attaaatttt aatgcacaat tgaatcataa caatatttct attcctggtg ttgtaaactt    840
taactataat aatgttgctt atagttctta tgttaaagac aaagatatta cgccaataag    900
tccagatgtt aacaaagtgg gttatcagga taaaagtaat cctggtttga ttcactggaa    960
agttctcatc aacaacaaac aaggtgctat tgataatttg actttgactg atgttgtcgg   1020
agaagatcaa gaaatcgtaa aagattcctt ggttgctgca cgcttgcagt acattgctgg   1080
tgatgatgtt gacagtttag atgaagctgc ttcgcgacct tatgctgagg atttttcaaa   1140
aaatgttact tatcaaacta atgatttagg attgacaaca ggatttacct atacaattcc   1200
aggatccagt aacaacgcta tctttatctc ttatactact cgtttaactt cttctcaatc   1260
tgctggtaaa gatgtcagca acactattgc tatttcagga aataatatta attattccaa   1320
tcaaacaggc tacgctcgta ttgaatccgc atatggtaga gctagttcta gagtaaagag   1380
gcaagcagaa acaacaactg ttactgaaac aacaactagt gaagcgacaa cagaaacaag   1440
tagtacaaca aataataatt caactactac agaaacagct actagcacaa caggagcttc   1500
aacaacacaa acaaaaacga ctgcttctca aacgaatgtt ccgacaacaa caaacataac   1560
aacaacttca aaacaagtaa ccaagcaaaa agcgaaattt gttttaccat caacaggtga   1620
acaagcaggg cttttgttaa ctactgtagg tcttgtaatt gttgctgtgg caggtgtcta   1680
tttctataga acacgtcgtt aacattgatt atgctaataa aaccgaggtt ggaatcgaag   1740
ctgattttcc tacctcgttt tttattgctt tttaaaaaac gactgtttat ttgtgttata   1800
ataacctttg atatctgttt taggaggaca aaatcattag taataacaat acggttaaaa   1860
gattattgaa gaaaagtaaa agaggtattt taagaggaat atttagtcgt gccacgatta   1920
ttgttgtttt acttcttgtt caagtttttc ttttgttatc aacctttctc tggtttaatc   1980
actatagact tcatcttgaa attttaggaa ttgtcttaat gataggatct gttctttatc   2040
ttgtgaatag tcagatggat acgctttcga ttattacttg gcttttggtt attttgcctt   2100
ttcctatttt aggaacactt tttttaatct atacaaagca agattggggt tatcgtgagt   2160
tgaaatcgct tatcaaaaaa tcaacacaag ctattaaacc ttattttcag tatgatcaac   2220
gtattttgta taaactaaaa gaaagtcacg ctagaactta taatttagcc caatatctcc   2280
```

```
atagaagcgg aggatttcct gtttacaaaa acaccaaagt cacgtacttt ccgaatggac   2340
aatctaaatt tgaagagatg aaaaaacagt tgctaaaagc tgaaaaattc atctttttag   2400
aatatttcat tatagctgaa ggattgatgt ggggtgaaat tctttctatt ttagaacaaa   2460
aagttcaaga aggagtagaa gttagggtga tgtatgatgg catgttagaa ttatcaacgc   2520
tttcttttga ctatgctaaa agactggaaa aaattgggat aaaagccaag gtttttttcac   2580
ccataactcc atttgtgtct acctattaca attaccgaga ccatcgtaaa attttagtta   2640
ttgataataa ggtcgctttt aatgggggga ttaatcttgc ggatgaatat atcaatcaaa   2700
ttgaacgatt tggttactgg aaagatactg ctgttatgct ggaaggtgaa ggtgtcgctt   2760
cttttacttt aatgttttta caaatgtggt ctactaccaa taaagattat gaatttgcac   2820
cttatttaac ccaaaatttt catgagattg ttgctaatgg ttatgtcatt ccctacagtg   2880
attcaccgct tgaccatgaa aaagtagggg aaaatgttta cattgatatc ctcaatcaag   2940
cgcgggatta tgtttacatt atgacgcctt atttaatttt agatagtgaa atggagcatg   3000
ctttacaatt tgctgctgaa cgtggtgttg atgttaaaat tattatgcca ggtattcctg   3060
ataagaaggt tccctttgcc ttagctaagc gctattttcc tgctcttctt gatgcgggag   3120
tcaagattta tgaattc                                                  3137

<210> SEQ ID NO 37
<211> LENGTH: 4865
<212> TYPE: DNA
<213> ORGANISM: Streptococcus mutans

<400> SEQUENCE: 37

atttcagcaa aaattgacaa atcaaatcaa ttatattaca attttttaac gtatattaca     60
aaaatatatt tggaagattt attcagattt ggaggattta tgaaagtcaa aaaaacttac    120
ggttttcgta aaagtaaaat tagtaaaaca ctgtgtggtg ctgttctagg aacagtagca    180
gcagtctctg tagcaggaca aaaggttttt gccgatgaaa cgaccactac tagtgatgta    240
gatactaaag tagttggaac acaaactgga aatccagcga ccaatttgcc agaggctcaa    300
ggaagtgcga gtaagcaagc tgaacaaagt caaaccaagc tggagagaca aatggttcat    360
accattgaag tacctaaaac tgatcttgat caagcagcaa aagatgctaa gtctgctggt    420
gtcaatgttg tccaagatgc cgatgttaat aaaggaactg ttaaaacagc tgaagaagca    480
gtccaaaaag aaactgaaat taaagaagat tacacaaaac aagctgagga tattaagaag    540
acaacagatc aatataaatc ggatgtagct gctcatgagg cagaagttgc taaaatcaaa    600
gctaaaaatc aggcaactaa agaacagtat ggaaaagata tggtagctca taaagccgag    660
gttgaacgca ttaatgctgc aaatgctgcc agtaaaacag cttatgaagc taaattggct    720
caatatcaag cagatttagc agccgttcaa aaaaccaatg ctgccaatca agcatcctat    780
caaaaagccc ttgctgctta tcaggctgaa ctgaaacgtg ttcaggaagc taatgcagcc    840
gccaaagccg cttatgatac tgctgtagca gcaaataatg ccaaaaatac agaaattgcc    900
gctgccaatg aagaaattag aaaacgcaat gcaacggcca aagctgaata tgagactaag    960
ttagctcaat atcaagctga actaaagcgt gttcaggaag ctaatgccgc aaacgaagca   1020
gactatcaag ctaaattgac cgcctatcaa acagagcttg ctcgcgttca gaaagccaat   1080
gcagatgcta aagcggccta tgaagcagct gtagcagcaa ataatgccaa aaatgcggca   1140
cttacagctg aaaatactgc aattaagcaa cgcaatgaga atgctaaggc gacttatgaa   1200
gctgcactca agcaatatga ggctgatttg gcagcggtga aaaaagctaa tgccgcaaac   1260
```

-continued

```
gaagcagact atcaagctaa attgaccgcc tatcaaacag agctcgctcg cgttcaaaag   1320
gccaatgcgg atgctaaagc ggcctatgaa gcagctgtag cagcaaataa tgccgcaaat   1380
gcagcgctca cagctgaaaa tactgcaatt aagaagcgca atgcggatgc taaagctgat   1440
tacgaagcaa aacttgctaa gtatcaagca gatcttgcca aatatcaaaa agatttagca   1500
gactatccag ttaagttaaa ggcatacgaa gatgaacaag cttctattaa agctgcactg   1560
gcagaacttg aaaaacataa aaatgaagac ggaaacttaa cagaaccatc tgctcaaaat   1620
ttggtctatg atcttgagcc aaatgcgaac ttatctttga caacagatgg gaagttcctt   1680
aaggcttctg ctgtggatga tgcttttagc aaaagcactt caaaagcaaa atatgaccaa   1740
aaaattcttc aattagatga tctagatatc actaacttag aacaatctaa tgatgttgct   1800
tcttctatgg agctttatgg caattttggt gataaagctg gctggtcaac gacagtaagc   1860
aataactcac aggttaaatg gggatcggta cttttagagc gcggtcaaag cgcaacagct   1920
acatacacta acctgcagaa ttcttattac aatggtaaaa agatttctaa aattgtctac   1980
aagtatacag tggaccctaa gtccaagttt caaggtcaaa aggtttggtt aggtattttt   2040
accgatccaa ctttaggtgt ttttgcttcc gcttatacag gtcaagttga aaaaaacact   2100
tctattttta ttaaaaatga attcactttc tatgacgaag atggaaaacc aattaatttt   2160
gataatgccc ttctatcagt agcttctctt aaccgagaaa ataattctat tgagatggcc   2220
aaagattata cgggtaaatt tgtcaaaatc tctggatcat ctatcggtga aaagaatggc   2280
atgatttatg ctacagatac tctcaacttt aggcagggtc aaggtggtgc tcgttggacc   2340
atgtatacca gagctagcga accgggatct ggctgggata gttcagatgc gcctaactct   2400
tggtatggtg ctggtgctat ccgcatgtct ggtcctaata acagtgtgac tttgggtgct   2460
atctcatcaa cacttgttgt gcctgctgat cctacaatgg caattgaaac cggcaaaaaa   2520
ccaaatattt ggtattcatt aaatggtaaa atccgtgcgg ttaatcttcc taaagttact   2580
aaggaaaaac ccacacctcc ggttaaacca acagctccaa ctaaaccaac ttatgaaaca   2640
gaaaagccat taaaaccggc accagtagct ccaaattatg aaaaggagcc aacaccaccg   2700
acaagaacac cggatcaagc agagccaaag aaacccactc cgccgaccta tgaaacagaa   2760
aagccgttgg agccagcacc tgttgagcca agctatgaag cagagccaac accgccgaca   2820
aggacaccgg atcaggcaga gccaaataaa cccacaccgc cgacctatga aacagaaaag   2880
ccgttggagc cagcacctgt tgagccaagc tatgaagcag agccaacgcc accgacacca   2940
acaccagatc aaccagaacc aaacaaacct gttgagccaa cttatgaggt tattccaaca   3000
ccgccgactg atcctgttta tcaagatctt ccaacacctc catctatacc aactgttcat   3060
ttccattact ttaaactagc tgttcagccg caggttaaca aagaaattag aaacaataac   3120
gatgttaata ttgacagaac tttggtggct aaacaatctg ttgttaagtt ccagctgaag   3180
acagcagatc tccctgctgg acgtgatgaa acaacttcct ttgtcttggt agatcccctg   3240
ccatctggtt atcaatttaa tcctgaagct acaaaagctg ccagccctgg ctttgatgtc   3300
gcttatgata atgcaactaa tacagtcacc ttcaaggcaa ctgcagcaac tttggctacg   3360
tttaatgctg atttgactaa gtcagtggca acgatttatc caacagtggt cggacaagtt   3420
cttaatgatg gcgcaactta taagaataat ttctcgctca cagtcaatga tgcttatggc   3480
attaaatcca atgttgttcg ggtgacaact cctggtaaac caaatgatcc agataaccca   3540
aataataatt acattaagcc aactaaggtt aataaaaatg aaaatggcgt tgttattgat   3600
ggtaaaacag ttcttgccgg ttcaacgaat tattatgagc taacttggga tttggatcaa   3660
```

```
tataaaaacg accgctcttc agcagatacc attcaacaag gattttacta tgtagatgat   3720

tatccagaag aagcgcttga attgcgtcag gatttagtga agattacaga tgctaatggc   3780

aatgaagtta ctggtgttag tgtggataat tatactagtc ttgaagcagc ccctcaagaa   3840

attagagatg ttctttctaa ggcaggaatt agacctaaag gtgctttcca aattttccgt   3900

gccgataatc caagagaatt ttatgatact tatgtcaaaa ctggaattga tttgaagatt   3960

gtatcaccaa tggttgttaa aaaacaaatg ggacaaacag gcgggagtta tgaagatcaa   4020

gcttaccaaa ttgactttgg taatggttat gcatcaaata tcgttatcaa taatgttcct   4080

aagattaacc ctaagaaaga tgtgacctta acacttgatc cggctgatac aaataatgtt   4140

gatggtcaga ctattccact taatacagtc tttaattacc gtttgattgg tggcattatc   4200

cctgcaaatc actcagaaga actctttgaa tacaatttct atgatgatta tgatcaaaca   4260

ggagatcact atactggtca gtataaagtt tttgccaagg ttgatatcac tcttaaaaac   4320

ggtgttatta tcaagtcagg tactgagtta actcagtata cgacagcgga agttgatacc   4380

actaaaggtg ctatcacaat taagttcaag gaagcctttc tgcgttctgt ttcaattgat   4440

tcagccttcc aagctgaaag ttatatccaa atgaaacgta ttgcggttgg tacttttgaa   4500

aatacctata ttaatactgt caatggggta acttacagtt caaatacagt gaaaacaact   4560

actcctgagg atcctgcaga ccctactgat ccgcaagatc catcatcacc gcggacttca   4620

actgtaatta tctacaaacc tcaatcaact gcttatcaac caagctctgt ccaaaaaacg   4680

ttaccaaata cgggagtaac aaacaatgct tatatgcctt tacttggtat tattggctta   4740

gttactagtt ttagtttgct tggcttaaag gctaagaaag attgacagca tagatattac   4800

attagaatta aaaagtgaga tgaagcgata aatcacagat tgagctttta tctcattttt   4860

tgatt                                                                4865
```

<210> SEQ ID NO 38
<211> LENGTH: 5170
<212> TYPE: DNA
<213> ORGANISM: Streptococcus mutans

<400> SEQUENCE: 38

```
tttgtgcttt agaattaatg ttggataaag tgtggagttt gtgctcgaaa aatagcagcg     60

attgaatgtg tttataattc tgattcagac attagttttt atttcagcaa aaattgacaa    120

atcaaatcaa ttatattaca attttttaac gtatattaca aaaatatatt tggaagattt    180

attcagattt ggaggattta tgaaagtcaa aaaaacttac ggttttcgta aaagtaaaat    240

tagtaaaaca ctgtgtggtg ctgttctagg aacagtagca gcagtctctg tagcaggaca    300

aaaggttttt gccgatgaaa cgaccactac tagtgatgta gatactaaag tagttggaac    360

acaaactgga aatccagcga ccaatttgcc agaggctcaa gggagtgcga gtaaggaagc    420

tgaacaaagt caaaccaagc tggagagaca aatggttcat accattgaag tacctaaaac    480

tgatcttgat caagcagcaa aagatgctaa gtctgctggt gtcaatgttg tccaagatgc    540

cgatgttaat aaaggaactg ttaaaacacc tgaagaagca gtccaaaaag aaactgaaat    600

taaagaagat tacacaaaac aagctgagga tattaagaag acaacagatc aatataaatc    660

ggatgtagct gctcatgagg cagaagttgc taaaatcaaa gctaaaaatc aggcaactaa    720

agaacagtat gaaaaagata tggcagctca taaagccgag gttgaacgca ttaatgctgc    780

aaatgctgcc agtaaaacag cttatgaagc taaattggct caatatcaag cagatttagc    840

agccgttcaa aaaaccaatg ctgccaatca agcagcctat caaaaagccc ttgctgctta    900
```

-continued

```
tcaggctgaa ctgaaacgtg ttcaggaagc taatgcagcc gccaaagccg cttatgatac    960
tgctgtagca gcaaataatg ccaaaaatac agaaattgcc gctgccaatg aagaaattag   1020
aaaacgcaat gcaacggcca aagctgaata tgagactaag ttagctcaat atcaagctga   1080
actaaagcgt gttcaggaag ctaatgccgc aaacgaagca gactatcaag ctaaattgac   1140
cgcctatcaa acagagcttg ctcgtgttca aaaagccaat gcggatgcta aagcgaccta   1200
tgaagcagct gtagcagcaa ataatgccaa aaatgcggca ctcacagctg aaaatactgc   1260
aattaagcaa cgcaatgaga atgctaaggc gacttatgaa gctgcactca agcaatatga   1320
ggccgatttg gcagcggtga aaaaagctaa tgccgcaaac gaagcagact atcaagctaa   1380
attgaccgcc tatcaaacag agctcgctcg cgttcaaaaa gccaatgcgg atgctaaagc   1440
ggcctatgaa gcagctgtag cagcaaataa tgccgcaaat gcagcgctca cagctgaaaa   1500
tactgcaatt aagaagcgca atgcggatgc taaagctgat tacgaagcaa aacttgctaa   1560
gtatcaagca gatcttgcca aatatcaaaa agatttagca gactatccag ttaagttaaa   1620
ggcatacgaa gatgaacaaa cttctattaa agctgcactg gcagaacttg aaaaacataa   1680
aaatgaagac ggaaacttaa cagaaccatc tgctcaaaat ttggtctatg atcttgagcc   1740
aaatgcgaac ttatctttga caacagatgg gaagttcctt aaggcttctg ctgtggatga   1800
tgcttttagc aaaagcactt caaaagcaaa atatgaccaa aaaattcttc aattagatga   1860
tctagatatc actaacttag aacaatctaa tgatgttgct tcttctatgg agctttatgg   1920
gaattttggt gataaagctg gctggtcaac gacagtaagc aataactcac aggttaaatg   1980
gggatcggta cttttagagc gcggtcaaag cgcaacagct acatacacta acctgcagaa   2040
ttcttattac aatggtaaaa agatttctaa aattgtctac aagtatacag tggaccctaa   2100
gtccaagttt caaggtcaaa aggtttggtt aggtattttt accgatccaa ctttaggtgt   2160
ttttgcttct gcttatacag gtcaagttga aaaaaacact tctattttta ttaaaaatga   2220
attcactttc tatcacgaag atgaaaaacc aattaatttt gataatgccc ttctctcagt   2280
gacttctctt aaccgtgaac ataactctat tgagatggct aaagattata gtggtaaatt   2340
tgtcaaaatc tctggttcat ctattggtga aaagaatggc atgatttatg ctacagatac   2400
tcttaacttt aaacagggtg aaggtggctc tcgctggact atgtataaaa atagtcaagc   2460
tggttcagga tgggatagtt cagatgcgcc gaattcttgg tatggagcag ggctattaa    2520
aatgtctggt ccgaataacc atgttactgt aggagcaact tctgcaacaa atgtaatgcc   2580
agtttctgac atgcctgttg ttcctggtaa ggacaatact gatggcaaaa aaccaaatat   2640
ttggtattct ttaaatggta aaatccgtgc ggttaatgtt cctaaagtta ctaaggaaaa   2700
acccacacct ccggttaaac caacagctcc aactaaacca acttatgaaa cagaaaagcc   2760
attaaaaccg gcaccagtag ctccaaatta tgaaaaggag ccaacaccgc cgacaaggac   2820
accggatcaa gcagagccaa acaaacccac accgccgacc tatgaaacag aaaagccgtt   2880
ggagccagca cctgttgagc caagctatga agcagagcca acaccgccga caaggacacc   2940
ggatcaggca gagccaaata aacccacacc gccgacctat gaaacagaaa agccgttgga   3000
gccagcacct gttgagccaa gctatgaagc agagccaacg ccaccgacac caacaccaga   3060
tcaaccagaa ccaaacaaac ctgttgagcc aacttatgag gttattccaa caccgccgac   3120
tgatcctgtt tatcaagatc ttccaacacc tccatctgat ccaactgttc atttccatta   3180
ctttaaacta gctgttcagc cgcaggttaa caaagaaatt agaaacaata acgatattaa   3240
tattgacaga actttggtgg ctaaacaatc tgttgttaag ttccagctga agacagcaga   3300
```

```
tctccctgct ggacgtgatg aaaccacttc ctttgtcttg gtagatcccc tgccatctgg   3360

ttatcaattt aatcctgaag ctacaaaagc tgcaagccct ggctttgatg tcacttatga   3420

taatgcaact aatacagtca ccttcaaggc aactgcagca actttggcta cgtttaatgc   3480

tgatttgact aagtcagtgg caacgattta tccaacagtg gtcggacaag ttcttaatga   3540

tggcgcaact tataagaata atttcacgct cacagtcaat gatgcttatg gcattaaatc   3600

caatgttgtt cgggtgacaa ctcctggtaa accaaatgat ccagataatc caaataataa   3660

ttatattaaa ccaactaagg ttaataaaaa cgaaaatggc gttgttattg atggtaaaac   3720

agttcttgcc ggttcaacga attattatga gctaacttgg gatttggatc aatataaaaa   3780

cgaccgctct tcagcagata ccattcaaaa aggattttac tatgtagatg attatccaga   3840

agaagcgctt gaattgcgtc aggatttagt gaagattaca gatgctaatg gtaatgaagt   3900

tactggtgtt agtgtggata attatactaa tcttgaagca gcccctcaag aaattagaga   3960

tgttctttct aaggcaggaa ttagacctaa aggtgctttc caaattttcc gtgccgataa   4020

tccaagagaa ttttatgata cttatgtcaa aactggaatt gatttgaaga ttgtatcacc   4080

aatggttgtt aaaaaacaaa tgggacaaac aggcggcagt tatgaaaatc aagcttacca   4140

aattgacttt ggtaatggtt atgcatcaaa tatcgttatc aataatgttc ctaagattaa   4200

ccctaagaaa gatgtgacct taacacttga tccggctgat acaaataatg ttgatggtca   4260

gactattcca cttaatacag tctttaatta ccgtttgatt ggtggcatta tccctgcaaa   4320

tcactcagaa gaactctttg aatacaattt ctatgatgat tatgatcaaa caggagatca   4380

ctatactggt cagtataaag tttttgccaa ggttgatatc actcttaaaa acggtgttat   4440

tatcaagtca ggtactgagt taactcagta tacgacagcg gaagttgata ccactaaagg   4500

tgctatcaca attaagttca aggaagcctt tctgcgttct gtttcaattg attcagcctt   4560

ccaagctgaa agttatatcc aaatgaaacg tattgcggtt ggtacttttg aaaataccta   4620

tattaatact gtcaatgggg taacttacag ttcaaataca gtgaaaacaa ctactcctga   4680

ggatcctgca gaccctactg atccgcaaga tccatcatca ccgcggactt caactgtaat   4740

tatctacaaa cctcaatcaa ctgcttatca gccaagctct gttcaagaaa cattaccaaa   4800

tacgggagta acaaacaatg cttatatgcc tttacttggt attattggct tagttactag   4860

ttttagtttg cttggtttaa aggctaagaa agattgacag catagacatt acattagaat   4920

taaaaagtga gatagaagcg ataaatcaca gattgagctt ttatctcatt ttttgattaa   4980

ttaaaagaga aataactagc ctatctttgt tctattaaaa aaacagttat gcttaaatag   5040

gaatatcatt aaccaatttt agcaaaacga tcatttagtg tgagtttttta actatctttc   5100

ttaaagaaaa aatgctataa tattttagtt gcacattact aacgtttgat aaggtacttc   5160

gcactgcctt                                                          5170
```

<210> SEQ ID NO 39
<211> LENGTH: 201
<212> TYPE: DNA
<213> ORGANISM: Streptococcus mutans

<400> SEQUENCE: 39

```
atggatacac aggcatttga acaatttgat gtaatggaca gccaaacact ttcaactgtt     60

gaaggtggga aggtatcggg tggagaagca gtcgcggcaa ttggaatatg tgcaactgct    120

tcagcagcaa ttggaggact ggcaggtgcg actcttgtta ccccatattg tgtaggcact    180

tggggactca ttcgatctca t                                              201
```

<210> SEQ ID NO 40
<211> LENGTH: 214
<212> TYPE: DNA
<213> ORGANISM: Streptococcus mutans

<400> SEQUENCE: 40

```
atggaattaa atgtaaataa ttataaaagt ttaactaatg atgaattgtc agaagttttt     60

ggtggagata aacaagctgc tgatacgttt ctttcagcgg taggaggagc tgcatcagga    120

ttcacctatt gtgcgtcaaa tggtgtgtgg cacccatata ttcttgctgg atgtgctgga    180

gttggtgcgg ttggatctgt agtttttcca cact                                214
```

<210> SEQ ID NO 41
<211> LENGTH: 6334
<212> TYPE: DNA
<213> ORGANISM: Streptococcus sobrinus

<400> SEQUENCE: 41

```
ctgcagacgg ccaaactgta acaggtggtt caatccttta ccgtcaacgc ggaactcata     60

tctatccagg tgctaatgtt ggccgtgggg gagatgatac cctcttcgct aaggttgaag    120

gtgtggttcg tttcgaacgt aaaggacgcg ataagaaaca agtttctgtt tacccaatcg    180

caaaataagt ttaaaaagca ggcttcaagc ctgttttttt tgcaaaattt ttgtctttcc    240

tgaaaatatc catatttctt tcttattaaa tctcattctg tctgaaagcc tattaagata    300

atgctagttt tttaacagaa tattacaaaa attgtggact agaaacgctg taagatcagt    360

cctcagcaga aattgcctta tttaaaaaga aattaagaaa aaaacgttta atataatgtt    420

aataactaga aataaattgc aaattgtggt aaaattaatt gatggttaga ataatttaac    480

tcgtaaaaaa gttaactgtc gttatttttc aaattaggag gactccattc atggagaaga    540

atgtacgttt taagatgcat aaggtgaaaa agagatgggt aaccctctct gtcgcatctg    600

ccaccatgtt ggcatcagcc cttggtgctt cagtagctag tgcggataca gacactgcta    660

gtgatgatag caaccaagcc gtggtaactg gtgaccagac tactaacaat caagccactg    720

accagacttc tattgcagca acagctacat cagaacagtc tgcttcaact gatgcagcaa    780

cagatcaagc atcagcagca gagcaaactc aaggaacaac agctagcaca gacacggcag    840

ctcaaacaac cacaaatgct aatgaagcta agtgggttcc gactgaaaat gagaaccaag    900

gttttacaga tgagatgtta gcagaagcca agaatgtggc tactgctgaa tctgattcaa    960

ttccatcaga cttggctaaa atgtcaaatg ttaagcaggt tgacggtaaa tattattact   1020

acgaccaaga tggcaatgtt aagaaaaact ttgctgtcag cgttggtgat aagatttatt   1080

actttgatga aactggcgct tacaaggaca ctagcaaggt tgatgccgac aagtccagtt   1140

cagctgtaag tcaaaatgca acaatatttg cagctaataa ccgtgcctac agcacctcag   1200

ctaaaaattt tgaagccgtt gataactacc tgacagctga ctcttggtat cgtccaaaat   1260

caatcctgaa agacggaaaa acttggacag aatctggcaa agatgacttc cgcccgcttc   1320

tcatggcttg gtggcctgat accgaaacca aacgtaacta cgttaattac atgaacaagg   1380

ttgttggtat tgataagacc tataccgctg aaacgagcca agctgattta acggcagcag   1440

cagaattggt tcaagctcgt attgaacaaa aaattacaag tgaaaataac actaagtggc   1500

tccgtgaggc gatttctgcc tttgtgaaaa ctcagccgca atggaatggt gaaagcgaaa   1560

agccttacga tgatcacttg caaaatggtg ctcttctctt tgacaatcaa actgatttaa   1620

caccagatac gcaatcgaac tatcgtttgc tcaatcgcac accaactaac caaactggtt   1680
```

-continued ccttggattc tcgtttcacc tataacccaa atgacccact gggcggctat gatttccttt 1740
tagccaacga tgttgataat tccaatccag tcgtgcaagc ggaacaactc aactggctgc 1800
actacctgct gaactttggc tctatctatg ccaatgatgc agatgccaat tttgactcaa 1860
tccgtgtaga tgcggttgat aatgttgatg ctgaccttct gcaaatctct agtgattacc 1920
ttaaggcagc ttacggtatt gataaaaaca acaaaaatgc taataaccac gtttctatcg 1980
tagaagcatg gagcgacaac gataccccct atctccatga tgatggcgac aacctcatga 2040
acatggacaa caagttccgt ttgtctatgc tttggtcttt ggctaaacca ttggacaaac 2100
gttctggctt gaatcccctc atccacaaca gtctggttga ccgtgaggtt gatgaccgtg 2160
aggttgaaac tgttccaagt tacagctttg ctcgggctca tgatagcgaa gttcaggata 2220
tcattcgtga tattattaag gctgagatta atccaaattc atttggttat tcattcaccc 2280
aagaagaaat tgaacaagct ttcaagattt acaacgaaga tctcaagaag actgataaaa 2340
aatacactca ctacaatgtg ccgctctctt acaccctgct tctcacaaac aagggctcta 2400
tcccacgtgt ctactatgga gatatgttca ccgatgatgg ccaatacatg gctaataaga 2460
ctgtgaacta cgatgctatc gaatcactcc taaaggctcg tatgaagtac gtttcaggtg 2520
gtcaggctat gcaaaattac caaatcggta atggcgaaat cttgacttct gtccgttatg 2580
gtaagggtgc ccttaaacaa agcgataagg gtgatgcgac aactcgtacg tcaggtgtcg 2640
gcgttgttat gggaaaccaa cccaacttta gcttggatgg aaaggttgta gccctcaaca 2700
tgggtgctgc ccacgctaac caagaatacc gtgctcttat ggtatcaact aaagacggtg 2760
ttgcaaccta tgctacagat gctgatgcta gcaaggctgg tctggttaag cgcacagatg 2820
aaaatggtta cctctacttc ttgaacgacg atctcaaggg ggttgctaac cctcaggttt 2880
ctggtttcct tcaagtctgg gtaccagtgg gagcagcaga tgaccaagat attcgtgtag 2940
cagctagcga tacagcaagt accgatggaa aatcactcca tcaagatgct gctatggact 3000
ctcgcgtcat gtttgaaggt ttctctaact tccaatcttt tgcgacaaaa gaagaagagt 3060
ataccaatgt tgttattgct aacaatgttg ataaatttgt ttcatgggga atcactgact 3120
ttgaaatggc tcctcagtat gtctcatcta ctgacggtca gttccttgac tctgtcattc 3180
aaaatggtta tgcctttacc gaccgttatg acttgggtat gtctaaagca aacaagtatg 3240
gtacagccga ccaattggtt aaggctatca aggctctcca tgctaaaggc ctgaaggtta 3300
tggcagactg ggttccagac caaatgtaca ccttccctaa acaagaagtg gtcactgtta 3360
ctcggacaga taagtttggc aaaccaatcg caggaagcca aattaatcac agtctctacg 3420
taacagatac aaagagctct ggtgatgact atcaagctaa atacggcggt gccttccttg 3480
acgaattaaa ggaaaaatat ccagaactct ttaccaagaa acaaatctct actggtcagg 3540
cgattgatcc atctgttaag attaaacaat ggtctgctaa gtactttaat ggaagtaata 3600
ttcttggccg gggtgccgat tatgtcctca gcgaccaagt cagcaacaag tacttcaacg 3660
ttgccagcga tacactcttc ttaccaagca gcttactcgg caaggttgta gagtctggta 3720
ttcgttatga tggtaagggt tatatttata actcaagtgc aactggtgac caagtcaaag 3780
caagcttcat taccgaagca ggcaatctat actacttcgg taaagacggt tatatggtga 3840
ctggcgctca aaccattaat ggtgctaact atttcttcct tgaaaatggt acggctcttc 3900
gcaacactat ttatacagat gctcaaggca atagccatta ctacgcaaat gacggtaaac 3960
gctatgaaaa tggttaccaa caatttggta atgactggcg ttacttcaag gacggtaata 4020
tggccgttgg cttgacaact gttgatggca atgttcaata ctttgataaa gatggtgttc 4080

```
aagctaagga taagattatt gtcacccgtg atggtaaggt tcgttacttt gaccaacata   4140

atggaaatgc tgcaaccaat accttcatcg ctgacaagac tggtcactgg tactatctag   4200

gtaaagatgg tgtcgctgtt accggtgctc aaaccgttgg gaaacaaaaa ctttactttg   4260

aagcaaacgg tcaacaagtt aagggtgact tcgtaacttc tgacgaaggt aaactttact   4320

tctacgatgt cgattcaggt gacatgtgga ctgatacctt cattgaagat aaggcaggca   4380

attggttcta ccttggtaaa gatggtgcag ctgtgactgg tgctcaaact attcgtggcc   4440

aaaaacttta cttcaaggct aacggccaac aagtcaaggg agatatcgtc aagggtactg   4500

atggtaagat ccgttactac gacgctaaat ctggtgaaca agtcttcaac aagactgtta   4560

aggccgctga tggcaagacc tatgttatcg gaaatgatgg cgttgcggtt gatccaagcg   4620

ttgtcaaagg acaaaccttc aaggatgctt caggtgctct tcgtttctat aacctcaaag   4680

gacaactggt aacaggcagc ggttggtatg aaactgcaaa tcacgattgg gtttatatcc   4740

aatctggtaa agccttgact ggggaacaga ccatcaatgg tcaacatctt tacttcaagg   4800

aagatggaca tcaagtcaaa ggacaactgg taacaggaac tgatggtaag gttcgctatt   4860

atgatgcaaa ttcaggcgac caagccttca acaagtctgt aacagttaac ggtaagactt   4920

actacttcgg taatgatggc actgctcaaa cagcgggaaa tcctaaggga caaaccttca   4980

aagatggttc agatatccgc ttttacagca tggaaggcca attagtgact ggcagtggtt   5040

ggtacgaaaa cgcacaaggt cagtggctct atgtgaaaaa tggtaaagtc ttgacaggcc   5100

tgcaaacagt tggtagccaa cgtgtttact ttgacgaaaa tggtattcaa gccaaaggta   5160

aagcagtaag aacttccgac ggtaagatac gctacttcga tgaaaattca ggtagcatga   5220

ttaccaacca atggaaattc gtttacggtc aatattatta cttcggtaat gatggcgcac   5280

gtatctaccg tggctggaac taatatttga gattttattt tctcaataca gagaagactt   5340

cctcggactg aggaagtctt ttttggttta gcgctttaag tccatttttc ttagattaga   5400

aaagaccacc cgtgaaattt tcccgagtgg ttttgtctat ttgacttagt taccataaac   5460

tctagtagcg ataccattag cgtcaatgac gtaggtttga ttgccaatgg tgatgcttgt   5520

gtccttggct aagtcaccac tatccttata gaagtagtga taattattgt cctcggtctt   5580

aacgaggcgt cccttggctt gtacagaagt ataagggtca aaatagtagg tttctccatt   5640

gatggtttgg gttccctgaa cggaggctcc ctcctgattg acgtaatacc aattgccata   5700

ctggtcagcg acaaagctat tggtcaaaat ctctccgcta ttgccatcat agaagtattt   5760

gtaaggtcca gaaggagcgg cataataact tcccttgatt tgtgttcccg ctcggtctgt   5820

gaaggcgtaa tgcttgccat gaatggtcac gcggccgtga gcagtgtttc cattttcatc   5880

attgtagtac caatctccgc cttgctttgg aagaaaaggt cggtagctat ttctccattg   5940

tctttaaaat aatgagtttg gagctcatca gtattaagag ctgtgttttt tgcctgtacc   6000

ccagtcaagc gatcaaagaa gtatcgtttg ccatcaatgg tttgccaacc tttaacagct   6060

tttccgtcct gaccaaaata gaaccagtta ccatccgtat tagcagcaaa gcgattggtc   6120

cacatatctc cagtatcagc atcgaagtag taggtgtctt tgtcgatttt agcagtagct   6180

cccttaactt gctgaccagt tgtctgatca aagtaaagct tttgactgtt gatggtttgc   6240

agccccttgg ctaagttacc atcttcttgc ctgtagtacc aatcgttttt cccagttgtt   6300

aagaagccaa cttgaacctt ggcatcttct gcag                               6334
```

<210> SEQ ID NO 42
<211> LENGTH: 4665
<212> TYPE: DNA

<213> ORGANISM: Streptococcus sobrinus

<400> SEQUENCE: 42

```
atggaaaaaa agctacatta taagcttcac aaggttaaaa aacattgggt tacgattgcg     60
gtagcctcta ttggtttagt aagcctcgtt ggtgctggta ctgtttccgc agaggataag    120
gtagctaatg atacgacggc ccaagcaaca gtaggagtag atactggtca ggatcaggct    180
actaccaatg acgcgaatac gaacactaca gatactgaca cggctgacca atcagccaat    240
actaatcaag atcaagcagg ttctgatcaa agtaacaatc aagatcaggc caagcaagat    300
acggccaata ccgatcgaaa tcaggcggat aacagtcaaa ctgataataa tcaagcgact    360
gaccaagcca ctagtccagc gacagatgga accagtgtcc aacgaagaga tgccgccaac    420
gtggcaacag cagcagatca agagggacaa acagctcctt ctgaacaaga aaaatcagca    480
gccctgtccc ttgacaatgt taagttgatt gatgggaaat actattatgt ccaagctgat    540
ggctcttaca agaagaattt tgccattact gtcaacggac aaatgctcta ctttgatagc    600
gatactggtg ccctttcgtc aacatcaacc tattccttct cacaagggac aaccaacttg    660
gttgatgact tctccagtca taacaaggcc tacgattcaa ctgccaaaag ttttgaattg    720
gttaatggtt atttaacagc taactcttgg taccgtccag ctggcattct gcgcaatggt    780
caaacttggg aagcttcaaa tgaaaacgac ctgcgccctg ttttgatgag ctggtggcct    840
gacaaggata cccaagttgc ttatgtcaac tacatgaata agtacttgag tgcaaatgag    900
acagaagtca ctaatgaaac atctcaggta gatttgaata aagaagctca atctattcaa    960
accaagattg aacaaaagat cacctctgat aatagtaccc aatggttacg gacagctatg   1020
gaggccttcg ttgctgctca gcctaagtgg aacatgagta ctgaaaactt caataagggt   1080
gaccacctgc aaggtggggc tctgctctat accaattcag atttgacccc ttgggcaaat   1140
tctgactacc gtctgctcaa ccgcacccca actcaacaag atggtactaa gaaatacttt   1200
actgaaggtg gtgaaggggg ttatgaattc ctgttgtcta atgacgttga taactcaaac   1260
cctgtcgttc aagcagaaca actgaaccaa ttgcactacc tgatgaactg gggcgatatt   1320
gtcatgggag ataaggatgc caattttgat ggcgttcgag tcgatgcggt cgataatgtc   1380
aatgccgact tgcttcaagt ctacagcaat tacttcaagg acaactataa ggtaacagat   1440
tccgaagcca atgctttagc tcatatttct atccttgaag cttggtcact aaatgataac   1500
caatataatg aagatacaaa tggtaccgcc ctgtctattg ataactcatc tcgtttgacc   1560
tctctagctg ttttaaccaa gcaacctggt caacggattg acctctcaaa cttgattagt   1620
gaatcggtca ataaggagcg ggctaatgat acggcctacg gcgatactat tccgacctat   1680
tcctttgttc gagctcatga ctcagaagta caaaccgtta tcgctaagat tgttaaggaa   1740
aagattgata ccaattcaga tggttatacc tttactcttg atcagttaaa ggatgccttc   1800
aagatttata atgaggatat ggctaaggtt aataagacct atacccatta taatattccg   1860
gcagcctatg cgcttttgct aagcaacatg gaatctgtcc ctcgagtgta ttacggtgat   1920
ctttataccg atgacggcca gtacatggct aaaaaatctc cttactatga tgctatcgca   1980
actatgctgc aaggtcgcat agcctatgtc tcaggcggtc aaagtgaaga agttcataag   2040
gttaatggga ataaccaaat cctttcatct gtccgttacg gtcaagatct catgtctgcc   2100
gatgatactc agggtaccga ccttagtcgg acttctggtc tagtaactct ggtcagcaat   2160
gatccaaacc tcgacctagg cggagacagc cttacagtca atatgggccg agctcatgct   2220
aaccaagcct atcgtccatt gattttaggg actaaggatg gtgttcaatc ctatctcaag   2280
```

-continued

```
gattctgata ccaacattgt taaatacact gatgccaatg gtaatttaac cttcacagcc   2340

gatgatatta agggttactc aaccgttgat atgagtggtt atttggctgt ttgggtgcca   2400

gttggcgcta aggatggtca agatgtgcgt gttgcagcag ataccaatca aaaggcagat   2460

ggtaagtccc tcaagacttc agctgccctt gattctcaag tcatctatga aggcttctca   2520

aatttccaag actttgcaaa taatgatgca gattatacca acaagaaaat tgctgaaaat   2580

gccgacttct tcaagaaatt gggtatcact tcgtttgaaa tggctccaca atacgtttca   2640

gccacagacg gtagcttttt ggattctatc attcaaaatg gttatgcctt ctcagaccgc   2700

tatgaccttg ccatgagcaa gaacaataaa tacggttcta aggatgattt ggctaatgcc   2760

ctcaaggccc tccacgctaa tggtattcaa gccattgccg actgggtacc agaccaaatt   2820

tatcaattac caggtgaaga agtggtaacg gctaaacgga ccaatagcta tggtaatcca   2880

acctttgatg cctacatcaa taatgccctc tatgctacca atactaagag cagcggtagt   2940

gactaccaag ctcaatatgg tggtgccttc ttggatgagc tcaaggctaa atacccagac   3000

atgttcaccg ttaacatgat ttcaactggt aagccaattg atccatcaac caagattaaa   3060

caatgggaag ctaaatactt caatggtacc aacgtccttg gcaagggtgc tggttatgtc   3120

ctcagtgatg atgcaaccgg taagtacttc accgtaaatg aaaatggtga cttcctacca   3180

gccagcttca ccggtgacca aaatgccaag acaggcttct actatgatgg cactggcatg   3240

gcttattact caacttcggg taataaggct gtcaacagct ttatctacga aggtggtcac   3300

tattattact tcgataaaga tggtcacatg gtgactggta gctacaaggc cgaagacggt   3360

aatgattatt acttcttgcc aaatggtatt cagatgcggg atgccatcta tcaagatgct   3420

caaggaaata gttactatta cggtcggaca ggtattcttt acaagggaga caactggtat   3480

ccatttgtag atcctaataa tgctaacaag acggtcttcc gttacttcga tgctaataat   3540

gtcatggcta ttggctatag aaacatgtat ggtcaaacct actactttga tgaaaatggt   3600

ttccaagcta aaggccaact cttaactgac gataagggta cccattactt cgatgaagat   3660

aatggtgcca tggctaagaa taaatttgtc aatgttggtg atgactggta ctacatggat   3720

ggtaacggta atgcggtcaa gggacaatac cctgtcaaca accaaatcct ttacttcaat   3780

ccagaaacgg gtgttcaggt taagggacaa tttattaccg atgctcaagg ccggacctca   3840

tactacgatg ctaattcagg tgccctcaag tccagtggtt tcttcacacc aaatggtagc   3900

gactggtact atgctgaaaa cggttatgtt tataaaggtt tcaaacaagt agctgaaaac   3960

caagatcaat ggtattactt cgaccaaact actggtaagc aagccaaggg agctgccaaa   4020

gttgacggac gagaccttta ctttaaccct gattcaggtg tccaagtcaa gggtgacttc   4080

gcaacagacg aatctggtaa taccagcttc taccatggtg ataacggtga taaggtcgtc   4140

ggaggtttct tcacaaccgg taacaatgct tggtactacg ctgataacaa tggtaatctt   4200

gtcaaaggct tccaagaaat agatggcaaa tggtaccact ttgacgaagt aactggccaa   4260

caagctaagg gagcagcctt ggttaatggt caacaactct atttcgatgt agattctggt   4320

atccaagtca agggtgactt tgtcacagat ggtcaaggaa atacttccta ttatgatgtc   4380

aattctggtg ataagaaggt caatggcttc ttcacaactg gtgataatgc ttggtactat   4440

gctgatggtc agggtaatct agccaaaggt cgcaagtcta ttgataatca agacctctac   4500

tttgatcctg caacaggtaa gcaagttaag gggcaactcg tttctattga tggtcgcaat   4560

tattacttcg atagtggctc tggtaatatg gccaagaacc gttttgtccg catcggtgat   4620

caatggattt acttcggcaa cgacggtgcc gctaccaacc tataa                  4665
```

<210> SEQ ID NO 43
<211> LENGTH: 4954
<212> TYPE: DNA
<213> ORGANISM: Streptococcus sobrinus

<400> SEQUENCE: 43

```
tgtaattaat ttgtaatggc ttttcatagt gtcaaagacc ctatttagag ctttttaaga     60
aaaaacgttt tcttgtttat aaaaaatgta aataactagt aatttttttg aaaaagtgct    120
actatagttt ggaaagtgaa atagttttta ggtcaatatt attttactat cgaaaatatt    180
atgggagaat gattttcatg gaaagaaaat tgcattacaa attacacaag gtaaaaaaac    240
agtgggtaac gattgccgtt gcctctgctg gtttggctag cattgttggt gctggttcat    300
taagccaaac tgtttctgcc gatgacttag ccaaggaaca agctgcggct agtcaacaaa    360
aggcagcagc caatcagaat gaggacgaag tggcttctga tgcagctgat actgctagtg    420
caaaagcgac ttccgaaaaa gaagttgtcc aatcttctga tacaaattca gaaactaacc    480
aagttgaaac taaagatcaa gctagcgcta aggaaagtgc tgacgcagta gccaagcaag    540
caccacaagc tggccctgca accactagcc aggttgcaag ctcagaaagc agctctgtag    600
cgcctagcaa ggaagctgat aaggcagctg ctggatcagt tagccaaaat gaagaagaag    660
cagccctatc gcttgccaat attaaaaaga ttgatggtaa gtattactat gttatggcag    720
acggttctta taagaagaac tttgccatta cagttgatgg tcaaatgctt tactttgatg    780
ccaaaacagg tgccctgtct tcaacctcta cctattcttt cagtcaaggt ttgacaccaa    840
ttgtttctga tttctcagtc aacaacaagg ctttcgattc ttctgaaaag agttttgaat    900
tggttgatgg ctatttgaca gctgaaagct ggtaccgtcc tgctaagatt cttgaaaatg    960
gtaaaacttg ggttgattct aaagaaactg acctacgccc agttctgatg agctggtggc   1020
caaacaagga tacgcaagtt gcctacctta actacatgag caaggcactt ggtggcaagg   1080
aagaattcac aactgaaacc tcccaattga ccttgaatac agccgctgag ttgattcaag   1140
ctaaaattga agctcgcgtt tctaaagaac aaggaacaaa gtggttgcgt gaagctatgg   1200
cagccttcgt tgctacccaa tctcgttgga ataaggacag cgaacaatac gataaggctg   1260
accacctgca aggcggagcc ctgctctata ccaataacaa cttgacagag tgggcaaatt   1320
caaactggcg cctgcttaac cgtaccccaa ctcgtcaaga tggtaaaacc cattactcta   1380
aggctgacaa atacggtggt tatgaattcc tcttggccaa cgacgtggat aactctaacc   1440
cagtcgttca agcggaaatg ctcaaccaaa tccactacct catgaactgg ggtgaaattg   1500
tgatgggtga taagaatgcc aactttgatg gtattcgtgt cgatgccgtg gataacgtca   1560
atgcagatac tctgcaactc tacaccaact actttaattc tgtttatggt gtcaacaagt   1620
ctgaagccca agccctggct cacatctcag tcttggaagc atggtcttac aatgataatg   1680
actataacca agacaccaac ggggctgccc tggctatgga caatggtcta cgcttttccc   1740
tgctttatac cttgacccgt ccgatcaatg aacggacacc tggtatgtca accctgatta   1800
aatcagaata tggtttgact gaccggacta agaatgataa gtatggagat acccaaccat   1860
cttatgtttt tgttcgggcg catgactcag aagtgcaaac cgttattgca caaatcatca   1920
aggaaaaaat tgatccaaca accgatggtt tcaccttcac cttggaccaa ttgaaacagg   1980
cctttgaaat ctacaacaag gatatgaata gtgttaacaa gcactatacc cactataata   2040
tcccagcagc ctacgctgtc atgttgtcta atatggaatc cgtaacccgg gtttactatg   2100
gtgacctctt caccgatgat ggtcaataca tggcatctaa atctccatat tatgatgcca   2160
```

```
tcaacactct cttgcgggct cgcattcgtt acgcagccgg tggtcaaatt atggaacaca   2220
attcctacaa accatcagca gccatgaagg cagctcatcc agatgctggt aatgtccttg   2280
gtaacagcga agtcttggta tcggttcgtt tcggtcaaga tgtcatgtct gccgatgata   2340
tgactggtgg taagctggct aagacctctg gtatgttcac cctgatttct aacaaccctg   2400
aattggaatt ggatgtcaat gaagaaatca aggttaacgt tggtaaaatc catgctggcc   2460
aagcctaccg tcccttgctt ttgacaactg ataagggtct gcaaaagtat ctcaatgatt   2520
ctgataccaa gttgaccaag attgctgaca aggatggttt cattaccttc aagggtagcg   2580
aaatcaaggg ttacaaacaa gtcgaagtca atggttacct ctcagtttgg gtaccagttg   2640
gtgctaaggc tgaccaagac attcgtgtgg ccccttcaac agcggctaag ggtgaaaagg   2700
ccaagactta cacagctagc caagctttgg aatcgcaatt aatctacgaa ggcttctcaa   2760
acttccaaga ttttgttcaa aaagattccc aatacaccaa caagaagatt gctgaaaata   2820
ctgacctctt caaggcttgg ggtgttacct catttgaaat ggcaccacaa tacgtttcag   2880
caaccgatgg aaccttcctg gattctatca ttgaaaacgg ttatgccttc accgaccgtt   2940
atgaccttgc catgagcaag aacaataaat acggttctaa ggaagatttg gccaacgccc   3000
tcaaggccct tcacgcagct ggtattcaag ccattgctga ctgggtacca gaccaaattt   3060
accaactgcc tggtaaggaa gttgttaccg ctagccgggt tgacaactac ggtcgtgtga   3120
aagttgacca accactagtt gaaaaacttt atctggccaa caccaagagc tcaggaaaag   3180
atttccaagc taaatacggt ggtgaattct tagcagaact gcaaaagaaa tatcctgaaa   3240
tgttcacgac taagatgatt tcaactggta aaaccattga tccatctgtc aaattgaaag   3300
aatggtctgc taagtacttc aacggaacca acgtccttga tcgtggtacg gactatatcc   3360
tcagtgatga aggtactggt aaatacttta ccgtcaatga aaaaggtgac ttcttacctg   3420
cctcattgac tggtaataag gatgccaaga ctggtttcta caacgatggt aagggcattg   3480
tttactacac aaccgccggt aacaaggcta gatcagcctt cgtaacagaa gcaggtaata   3540
cctattactt cgactacacc ggccatatgg taacaggccc taacgttatt aacactaaat   3600
tctattactt cttgccaaat ggtatcatgc ttaaggatgc tattaagcag gatgaaaaag   3660
gtcgttccgt atactacggt aagactggtg ttatgtacaa gggtggccgc gataatgaat   3720
ggttcgccat gacagactct aagggtcaaa tgcgtttccg tcactttgac aggtacggct   3780
tcatgtctat cggtttggta accatcaacc aaaatgttca gtattatgat gaaaatggtt   3840
tccaagttaa aggtgaattt gtaaccgatc aggatggaca aacccgttac ttcgaccaag   3900
gttcaggtaa cttggttaag ggacaattcc tcaacaagga tggcaactgg tactaccttg   3960
atgaccaagg gctagttgct aaaggagctc agacaattaa aggtcaaaag ctttactttg   4020
acacaaaaac cggtgtccaa gttaaagggg attttgtaac ggataaagat ggcaatacct   4080
tcttttacag tggagatact ggcgatttaa tccttggtca gttcttctca actggaaata   4140
acgcttggtt ctatgctgat gaaaatggtc atgtcgctaa gggagctaag actatcagag   4200
gtcagaagct ctactttgat acaaaaacag gtcagcaagc taagggacgc tttatccgtg   4260
atgacaaggg ggttcgttac tatgatgctg acacaggtac cttggtaacc aacgctttcc   4320
ttgaaactaa ggctggttct aaccaatggt attacatggg agcagatggt tatgctgtca   4380
aggggaacca gaccataaaa aatcagcaca tgtattttga tgctgaaact ggccaacaag   4440
ctaagggaat tatagtgaca gatgccaatg gtcgcaagta tttctatgat acttttactg   4500
gcagtcgtgt tgtaaaccaa tttgttttgg ttaatggaaa ttggtatttc tttggttatg   4560
```

```
atggagctgc agtaacaggt ttccatgata tcaagggaca acacctttac ttcaattccg   4620

atggaacaca ggccaaaggg actacggtaa aaattggcaa tcgcagctat acctttgatg   4680

ctcacactgg tgagctgaca tctgttcatt atggctgatt gtcagactgc aaagaaaaga   4740

atcgagtttc tcggttcttt tttgaatttg gttaagtttc aaatcttata ttggccttgc   4800

ctgccggaaa attttgattt tcgaagagga taaggtgaca ttttaagctg gaatagcgac   4860

atttggggat atgtctatag actgcaggct ataggtatag tagactgtat tagttgaatt   4920

tactcagcaa cattaactct catggatccg aaag                               4954
```

<210> SEQ ID NO 44
<211> LENGTH: 993
<212> TYPE: DNA
<213> ORGANISM: Streptococcus sobrinus

<400> SEQUENCE: 44

```
atgcaaggaa agaaaactta taagatgcac aaggttaaaa agcattgggt aagcattgct     60

ggtacagcaa cagtcttatc tgtcgcttta ttagcgaata atcaggtcaa ggctgatgaa    120

caaacagaat caactgttgt tcgggccgat agcgctgctg ttgtaaccaa gcctgctgat    180

gagaccagtc agactgacca agcacagcca gcgactgctg aacaaacggc tacagctaat    240

caaaatcagc aagcttctgc taatactgct gatcaagccc aagagcaaag acaggataca    300

gccaatcaag ataaatggca agctgttgat caagctagcc aacctgaaca agtcgctact    360

gctgtcgatc aagttcaaaa cgcagctaag agcgatgcta accaagtagt aagtacggat    420

gtaaaagata gccatgctgt tgtcagcaag gatgatgcca agtcatcttc agaccaagca    480

gctgagcaag ctggcttcta cacaactggt aataatgact ggtattataa acaagaagat    540

ggtaatttag ctaaaggatt acaaaccatc aacggtcaaa ccctttactt cgataccaat    600

acgggtaaac aagttaaagg ttctgctgtt acaattgatg gtaaagaata ctatttcgac    660

caagatactg gtgacatgtg gaaagatcgt ttccgtcaaa ttgataagca agactatcgc    720

ggtgttgctc caggttcgaa ggttgggatt gcttggctct attaccaagc agatggttcc    780

gttgcttcag gtttgaccaa tacacctgat ggccgcactc tcatgtttaa tacttataat    840

cacgagcaag tcaagggtaa actggtcaat accgacggta gcaactatcg ttactttgac    900

ctgcataccg gtgacatgtt gcgtaataca agcatctatg atggtagcca aaaatacaac    960

atcgatgaga acggtattgc aaccaaggcc taa                                 993
```

<210> SEQ ID NO 45
<211> LENGTH: 2853
<212> TYPE: DNA
<213> ORGANISM: Streptococcus sobrinus

<400> SEQUENCE: 45

```
tctagacagt cagaaggaaa tctgcgtttt aggcggatcc aaaattggct tggttgagct     60

tccttgggct ctgatgaatc ctggcgacct gctcttgtta ccggaccctg gctatcccga    120

ctacctctca ggtgtagcct tgggacgagt agactatgaa accttccctc tgctggctga    180

gaatgacttt ctgccagatt tagcagccat tcccgaagag atcgcccgaa gggctaaatt    240

tatctatatc aactatccca ataatccgac aggacgtgtc gccacatctg acttctacca    300

agacttagtg gcctgggcta agaagtacca agtgggtgtc gtcagcgact ttgcctatgt    360

gccctgggct accagggcta tgaaaatcct agctttctgt ctacaccggg ggccaaggag    420

gtcggtcttg aactctatac cttctccaag acctttaaca tggccggctg ggcgattggc    480
```

-continued

```
ctttgcggct gggaatgccg atatgattga agccctcaac ctcattcaag accacctctt    540
cgtcagcatc tttcctgcta ttcaagatgc tggagtagcg gcccttttgg atccacaggc    600
caaggaagct attgtccagc tcaatcagat ctacgaccaa agacgggagg cttttgtcca    660
agcgtcagcc aagattggtt ggcaggcctt tccttccaag ggttcctttt atgcctggat    720
gccagtccct aggggttaca ctagccaaag tttcgcggac ctcttgctag agaaggccca    780
tgttgcggtt gcaccaggag tgggctttgg tcaagcaggc gatggctatg tcagaatcgg    840
tcttctggtt gaaccagaac gcctggctga agcagtagaa cggataggag ccctaaacct    900
atttggatag gcggtttctt gaaaactatc aattaaagtt gaggaagtat ttccaccaag    960
tcagtgaaat tttctcagtt ctagccaagt tcatctgagc ttggcttttt tatggttaaa   1020
ttgcttttga tttttattag aattgacttc aattgagagt aatcttaatc tataagattg   1080
gcaaaataga atggacatga tacaataaag agtaatgaca tacgatttgg cattggctta   1140
cagggataag attaaaggaa cgtggcggga gaggcccaga tggaactgat tgaggattta   1200
aatattttac agagaaaggc attatcagta gggctgcttt gcgccagcct tttgctctgt   1260
ataccttct ttttcttttt ttcttggctg tccagactga ctattggcat ttccaatatc    1320
ttttttaatt attggtggga gcctttttc gctccctttg ctttggccct tttattggtt    1380
atccacgagg ggattcatgg cttttatttc aaacttttca agcctgagaa tcctttgaag   1440
tatggtactg attggcgttt gggcctcttt aatgccacca gtcctggttc tcgatatcct   1500
agaagccaga tgctaattat ttatttggcc ccctttgtcc tgaccagcct gctcttgacc   1560
ctgcttctag ccttggggac actttctccc cttgcctatc tctttttagc agtcattcac   1620
acagccatgt gcgtaggaga tttttacttt tcctacctct tgctttggaa ataccgcagt   1680
attcgatttt ggttgaggat acagaaactg gtattaaaat ttttagtctt gaataaacca   1740
agtggcatct gtactttatt agtcttatca tagaaataac cctagcatgg ttcgcgctag   1800
ggttattgtg tttttgaaaa tagatttatc tagagtcaag gttgactaca atttgtaatc   1860
ttagtctaaa atcagaaatt tcttgataaa aggaaagagt agcagtaggg cgactataca   1920
ggccagggtc tcgcctaaga aagacgagcc gttgatgatg gctgaatata ggagagcaga   1980
ctgtcctttc ggagcatagc tgccccaaaa gaggatacct gcgataaaat gaatacagta   2040
gcgagccaga cttccgatga gaactcctac taccataaga ctcaggcttc tgacggtctg   2100
atttttttc aggctttggt taagccaggg cttgattaga ccgcaaagcc aatcaggcta    2160
aaggcaataa agtattctag gaaaccttgc cataggttga gccagcctcc agctgcttgc   2220
ccgagagcga cctggaggat gccccagatg aaaccggcca tgatagcagg tttggctcct   2280
cgccgaaaag cgagcagaaa gatgggggtc atcttgaagg acaaggaaat ccagggcccg   2340
atggctaaag gttgcgtgaa aatatccaga accatagcta aaccagcgaa gatagcaatt   2400
tcagctaggc ctgcaacatg tgatctttgc ataaaaaaat ccttcctaac ccagttggac   2460
tgggcaaatg tcaattgatt tgccacaatc aaaactggga cgaggaaggt tagctctctc   2520
atctctggtt tgcacatccc ttacgcaggc attaccctgt tcaggttcaa agagtttagg   2580
ccccagctag gaatcctacc tagctgtcac cattctcagc aaaagctcct cttgtgacat   2640
ggtcatagta acagataatc tgtttaattt caagcagatt taatagcctc caggaaactt   2700
gaaataaaac tgaaataaaa ctgaattttt tataaagcct agattaagca atcgtttgca   2760
ttgacaatca ctagataagt gttattatag atagtattgt aacgaaacat ttcagatgtt   2820
acaaaaatgt aaattggagg gaattataat atg                                2853
```

<210> SEQ ID NO 46
<211> LENGTH: 4753
<212> TYPE: DNA
<213> ORGANISM: Streptococcus sobrinus

<400> SEQUENCE: 46

```
taaaactgaa ttttttataa agcctagatt aagcaatcat ttgcattgac aatcactaga      60
taagtgttat tatagatagt attgtaacga aacatttcag atgttacaaa aatgtaaatt     120
ggagggaatt ataatatgca acgaaaagag acttttgggt gccgcaaaag taaaatcagg     180
taggaccctt tctggtgcct tactaggaac tgctatctta gcatctggag caggtcaaaa     240
ggcgctcgct gaagaaacaa gtaccacttc aacttcgggg ggagataccg cagtcgttgg     300
gacggagact gggaatcccg ccaccaacct gcctgacaaa caggacaatc caagttcgca     360
agccgagaca agtcaggccc aagcccgtca aaagacaggg gcaatgtcag tagatgtgtc     420
tacaagtgag cttgacgaag ctgctaaaag tccccaagaa gctggtgtga ccgtttcgca     480
ggatgctacc gtcaataaag ggacagtaga accttctgac gaagctaacc aaaaagaacc     540
cgaaatcaag gatgactaca gcaagcaagc agcagacatc caaaaggcaa cagaagacta     600
taaggcatca gtggctgcca accaagccga aacagaccgc atcaatcaag aaatcgcggc     660
taagaaggcc caatacgaac aagatttggc ggccaacaag gctgaagtgg aacgatcact     720
aatgagaatg cgcaagccaa ggccgatcta cgaagctaag ttagcccaga atcaaaagga     780
cttggccgct attcaacagg ccaactccga cagtcaagca gcctacgccg ccgctaagga     840
agcctacgac aaagaatggg ctcgggtgca ggccgctaat gccgcagcta agaaggccta     900
tgaagaagct ctagccgcta acacagctaa gaatgaccaa atcaaggcag aaatcgaagc     960
tatccagcag cgatcagcta aagctgacta tgaagctaag ttagcccagt atgagaaaga    1020
tttagcagct gcccaggctg gcaatgcagc taatgaagct gactaccaag ctaagaaggc    1080
agcttatgaa caagagttag cacgcgtgca agccgctaat gcagctgcca agcaggccta    1140
cgaacaagct ctagctgcca actcggccaa gaacgcccaa atcacggccg aaaatgaggc    1200
tatccagcaa aatgcgcaag ctaaggctga ctatgaagct aaattagccc aatatcaaaa    1260
agatttggcc gcagctcaat ctggtaacgc cgctaatgag gcagactacc aagaaaaatt    1320
agcagcctat gaaaaggaac tcgctcgtgt gcaagcagcc aatgcagctg ctaagcaagc    1380
atatgagcag caagttcagc aagctaatgc taaaaatgcc gaaattacgg aagccaaccg    1440
tgctatccgt gaacgcaatg ccaaggccaa gacagactat gaactcaaac tgtctaagta    1500
ccaagaagag cttgctcagt acaagaagga cctagcggaa tacccagcta aactccaagc    1560
ctatcaagat gaacaagccg caatcaaggc agctctggca gagttggaaa aacacaagaa    1620
cgaagacggg aacctcagcg agccctcagc ccaaagtctg gtctatgatt tagagcccaa    1680
tgctcaggtt gccctagtaa ctgacgggaa attgctgaaa gcatcagccc ttgacgaggc    1740
ctttagccat gatgagaaaa attataataa ccatctccta caaccagata atctgaatgt    1800
gacctatctg gagcaggctg atgatgtggc ctcctcagta gagctctttg gtaatttcgg    1860
tgataaggct ggttggacaa ccactgtcag caatggtgca gaagttaagt ttgcctctgt    1920
cctcctcaag cgtggccaaa gtgctacagc cacctatacc aacctaaaaa actcttacta    1980
caatggtaag aagatttcta aggtggtcta caagtatacg gttgaccctg actccaagtt    2040
ccaaaatcct actggtaacg tttggctggg catcttcacc gacccaaccc taggggtctt    2100
tgcctcagcc tatacgggtc aaaacgagaa ggatacctct atctttatca agaatgaatt    2160
```

```
caccttctac gatgaagacg gtaatcccat cgactttgat aatgccctct tatcagttgc   2220
ctcccttaac agggaacaca attccattga gatggccaag gactacagcg gtaccttcgt   2280
taagatttct ggctcatcca ttggtgaaaa aaatggcatg atctatgcga ccgataccct   2340
caactttaaa aagggtgaag gcggttccct tcacaccatg tacaccagag caagtgagcc   2400
tggttcaggt tgggactctg ctgatgctcc taattcttgg tatggtgctg gtgctgtcag   2460
aatgtccggc cccaacaact acatcacctt gggggcaacc tcagcgacca atgttctcag   2520
cctagctgaa atgccacagg tacctggtaa ggataatact gctggtaaaa aaccaaatat   2580
ctggtattcc cttaatggta agattcgggc agtcaatgtc cctaaggtga ccaaggaaaa   2640
accaacccca ccagtcgaac caactaaacc tgatgagcca acctatgagg ttgaaaagga   2700
gttggtggac ctgccagttg agccgaaata tgagccggaa ccaacgccgc caagcaagaa   2760
tcccgatcaa tctatcccag agaaaccggt cgagccaacc tatgaggttg aaaaagagtt   2820
ggaaccagca ccggtagaac caagctacga aaaggaacca accccacctc agtctacccc   2880
agaccaagag gaaccggaaa aacccgtcga gccaagctac caaagcttgc caaccccacc   2940
agttgaacct gtttatgaga ctgtccctgg ccccgtcagc gtgccaacgg ttcgttacca   3000
ctactataaa ctagcggtcc aacccggcgt caccaaggaa atcaaaaacc aggatgatct   3060
ggatattgac aagaccctgg tggctaagca gtcgacggtt aagttccaat tgaagacagc   3120
agacctgcca gccggtcgtc cagaaacgac ctcctttgtc ttgatggatc ctctgccaag   3180
cggttaccaa cttaatctgg aagctaccaa ggtcgccagc ccaggctttg aagctagcta   3240
tgatgccatg acccatacgg taaccttcac cgcaaccgct gagaccttgg cggcgctcaa   3300
ccaggatctg accaaggccg tggcgactat ctacccaaca gttgtgggac aagtcctcaa   3360
cgatggcgct acctacacca ataacttcac cctgatggtc aatgatgctt acggtattaa   3420
atccaatatc gttcgcgtga ccacaccagg gaaacctaac gacccagaca acccaagcaa   3480
caactacatc accccgcaca aggtcaacaa gaatgaaaac ggtgtggtga ttgatggtaa   3540
gtccgtccta gctggtacca ccaactacta tgaattgact tgggacctgg accaatacaa   3600
gggcgataaa tcggccaagg agatcatcca aaaaggcttc ttctatgtgg atgactatcc   3660
tgaagaagcg ctggacttgc gcaccgacct gattaagctg accgatgcca acggcaaggc   3720
ggtcactggt gtcagcgtgg ctgactacgc cagtctggag gccgcaccag cagctgttca   3780
agacatgctc aagaaggcca acattatccc taagggagcc ttccaagtct ttaccgctga   3840
cgatcctcag gccttctacg atgcctatgt ggttaccgga actgacctga ccatcgtcac   3900
tccaatgacg gtcaaggccg agatgggtaa gacgggtggc agctatgaaa acagggccta   3960
ccaaatagac tttggcaatg gctatgaatc caacctagtg gtcaataatg tgccgaaaat   4020
taatcctgaa aaggatgtga ccttgaccat ggatccagcg gatagtacca atgtggatgg   4080
acagaccatc gccctcaatc aggtctttaa ctaccgtctc atcggtggta tcattccagc   4140
ggaccatgcc gaagagctct ttgagtacag ctttagcgat gactatgacc aaactggaga   4200
ccagtacacg ggccaataca aggcctttgc caaggttgac ctgaccctca aggatggtac   4260
aatcatcaag gcgggtactg acttgacttc atatacagaa gcgcaagttg atgaagctaa   4320
tggccaaatt gttgtgacct tcaaggaaga tttcttgcgg tctgtgtctg tagactcggc   4380
cttccaagcg gaagtctacc tacagatgaa gcggatagcc gtcgggacct ttgccaatac   4440
ctatgtcaat acggtcaatg gaattaccta tagctctaat acggtaagga ccagcacacc   4500
agagccgaag cagccaagtc cagtggatcc taagaccact actacggtag tcttccagcc   4560
```

```
tcgtcagggc aaggcttatc agccagcgcc gccagcagga gctcaattgc cagccacagg   4620

ggatagtagc aatgcttacc tgccactttt aggcctcgta agcctgactg ctggctttag   4680

ctgttaggac tgcgccggaa gcaggactaa agaatccaac aagaaaaaat gggaaagttt   4740

gcctttctca ttt                                                      4753


<210> SEQ ID NO 47
<211> LENGTH: 246
<212> TYPE: DNA
<213> ORGANISM: Lactobacillus

<400> SEQUENCE: 47

atgatttcaa tgatttcatc tcatcaaaaa acgttaactg ataaagaatt agcattaatt     60

tctgggggga aaacgtacta tggtactaat ggtgtgcatt gtactaaaaa gagtctttgg    120

ggtaaagtac gcttaaaaaa cgtgattcct ggaactcttt gtcgtaagca atcgttgccg    180

atcaaacagg atttaaaaat tttactgggc tgggctacag gtgcttttgg caagacattt    240

cattaa                                                               246


<210> SEQ ID NO 48
<211> LENGTH: 276
<212> TYPE: DNA
<213> ORGANISM: Lactobacillus

<400> SEQUENCE: 48

atggttacta agtacggacg taatttaggt ttgagcaagg tagagttgtt tgcaatttgg     60

gcggttttag tagttgctct tttattggcc acagcgaaca tttattggat tgctgatcaa    120

ttcgggattc atttagcgac tggaacagcc cgtaagttat tagatgcagt ggcttctggt    180

gcctcattgg gaactgcctt tgctgctatt ttgggcgtga cattacctgc atgggctttg    240

gcagctgcag gagcattggg agcgactgcg gcttag                              276


<210> SEQ ID NO 49
<211> LENGTH: 252
<212> TYPE: DNA
<213> ORGANISM: Lactobacillus

<400> SEQUENCE: 49

tctagagatc tattattatt ttctaatttt ggaggaggtg ctgttttgct tagttataaa     60

gaattggata ctgcaaaact tcaagaaatt tccggtggat atagctattt tggaggttct    120

aatggctatt cttggagaga caagaggggt cattggcatt atactgttac caagggtggc    180

ttcgaaaccg ttattggaat aattggagat ggctggggta gtgctggtgc accaggacct    240

gggcaacatt aa                                                        252


<210> SEQ ID NO 50
<211> LENGTH: 141
<212> TYPE: DNA
<213> ORGANISM: Lactobacillus

<400> SEQUENCE: 50

atgatttcat ctcatcaaaa aacgttaact gataaagaat tagcattaat ttctgggggg     60

aaaacgcact acccgactaa tgcatggaaa agtctttgga aaggtttctg ggaaagcctt    120

cgttatactg acggttttta g                                              141
```

BIOSENSOR

RELATED APPLICATION

This application claims priority to Japanese patent application 2007-252148 filed on Sep. 27, 2007, which is herein incorporated by reference in its entirety.

BACKGROUND OF THE INVENTION

1. Field of the Invention

The present invention relates to a biosensor.

2. Related Background Art

"Biosensor" is a general term for chemical sensors that utilize biological molecular recognition mechanisms, and known types of biosensors include enzyme sensors, immunosensors, microbiological sensors, ion channel sensors and the like.

Biosensors accomplish detection of analytes by converting a change (for example, a substance change, color change, heat absorption or release, mass change or the like) produced-by interaction between an enzyme, antibody, microbe, ion channel or the like that is immobilized on a substrate recognition element, and its substrate (the analyte), into a signal that is detectable using a signal converter (an electrode, light receiving element, thermal element, piezoelectric element, fluorescent anisotropy detector or the like).

For example, in a construction where a monoclonal antibody is immobilized on the substrate recognition element and an antigen (the analyte) is allowed to specifically bind with the monoclonal antibody by antigen-antibody reaction, the sensor can obtain a signal proportional to the concentration of the analyte even when contaminants are abundant in the sample.

The lactic acid producing bacterium *Mutans Streptococci* is associated with intraoral caries. It has therefore been proposed that onset of caries can be prevented by detecting the major *Mutans Streptococci* bacterium detected in the human mouth, *Streptococcus mutans*, by antibody immunoassay (Patent document 1).

Since *Streptococcus mutans* is known to secrete glucosyltransferase in the mouth, the use of an antibody that specifically binds this enzyme for immunological detection of the bacterium has also been proposed (Patent document 2).

[Patent document 1] Japanese Unexamined Patent Publication No. 2003-183299

[Patent document 2] Japanese Unexamined Patent Publication No. 2002-267673

SUMMARY OF THE INVENTION

Detection of bacterium that is invisible to the naked eye, however, currently involves specimen extraction, identification by culturing in selective medium, and detection of the bacterium by antibody-based ELISA or Western blotting methods, and effort and time are required to obtain the analysis results.

Moreover, while biosensors comprising monoclonal antibody immobilized on the substrate recognition element can in principle detect analytes in a shorter time compared to ELISA or Western blotting methods, the antibody immobilized on the substrate recognition element is easily affected by drying and by proteases during storage and use of the biosensor, and therefore the detection sensitivity is often significantly reduced. Such biosensors are therefore associated with problems of stability.

Also, biosensors having monoclonal antibody immobilized on the substrate recognition element often employ substances that are harmful to the human body to maintain antibody stability, therefore the substrate recognition elements of such biosensors cannot be directly inserted into the mouth for detection of intraoral bacterium, and it has been necessary to perform indirect measurement of samples such as saliva in separate containers.

It is therefore an object of the present invention to provide a stabilized biosensor wherein the detection sensitivity for target microbe (target bacterium) is not impaired depending on the storage condition or measuring sample, and to directly measure target bacterium in a body fluid by insertion of the substrate recognition element of the biosensor.

The invention provides a biosensor comprising a microbe-binding aptamer(s) in the substrate recognition element.

Because an aptamer(s) is more resistant to enzymolysis and drying compared to proteins such as antibodies, the biosensor is characterized in that its detection sensitivity for target bacterium is not impaired by the storage condition of the biosensor itself or depending on the measuring sample. Consequently, the presence of bacterium can be determined by a single measurement without being concerned with the condition of the substrate recognition element, even when detecting bacterium present in rare samples.

Such bacterium is preferably an intraoral bacterium, and more preferably a cariogenic bacterium or a periodontal bacterium.

Since the biosensor is a sensor having an aptamer(s) immobilized on the substrate recognition element, the substrate recognition element does not contain agents harmful to the human body (for example, $NaN_3$) that are used to maintain the stability of antibodies, and therefore the substrate recognition element can be inserted directly into the mouth for direct measurement of intraoral bacterium in saliva, and especially a cariogenic bacterium or a periodontal bacterium.

The cariogenic bacterium is preferably *Streptococcus mutans, Streptococcus sobrinus* or *Lactobacillus acidophilus*.

Numerous bacteria have been reported to be associated with onset of caries, but the three species *Streptococcus mutans, Streptococcus sobrinus* and *Lactobacillus acidophilus* are most associated with caries in humans. Therefore, a biosensor that detects *Streptococcus mutans, Streptococcus sobrinus* and/or *Lactobacillus acidophilus* will be able to accurately and easily determine the risk of human caries and can contribute to prevention of caries onset. Detection of *Streptococcus mutans* present in the human mouth using an aptamer(s) permits higher detection sensitivity than detection using anti-*Streptococcus mutans* antibody.

The aptamer(s) preferably binds to a bacterial cell surface molecule.

Bacterial cell surface molecules are bacterial proteins displayed on bacterial cell surfaces, and therefore target bacterium can be distinguished and detected at high sensitivity if an aptamer(s) that bind to the bacterial cell surface molecules are immobilized on the substrate recognition element of the biosensor.

The aptamer(s) preferably binds with a protein comprising any of the amino acid sequences as set forth in SEQ ID NO: 1-15.

Proteins comprising the amino acid sequences as set forth in SEQ ID NO: 1-15 are specifically found on the bacterial cell surfaces of *Streptococcus mutans*, and therefore if an aptamer(s) that bind with these proteins are immobilized on the substrate recognition element of the biosensor, it will be possible to specifically detect *Streptococcus mutans* even under conditions where other intraoral bacterium is present The aptamer(s) also preferably binds with a protein comprising any of the amino acid sequences as set forth in SEQ ID NO: 16-21.

Proteins comprising the amino acid sequences as set forth in SEQ ID NO: 16-21 are specifically found on the bacterial cell surfaces of *Streptococcus sobrinus*, and therefore if an aptamer(s) that bind with these proteins are immobilized on the substrate recognition element of the biosensor, it will be possible to specifically detect *Streptococcus sobrinus* even under conditions where other intraoral bacterium is present.

The aptamer(s) also preferably binds with a protein comprising any of the amino acid sequences as set forth in SEQ ID NO: 22-25.

Proteins comprising the amino acid sequences as set forth in SEQ ID NO: 22-25 are specifically found on the bacterial cell surfaces of *Lactobacillus acidophilus*, and therefore if an aptamer(s) that bind with these proteins are immobilized on the substrate recognition element of the biosensor, it will be possible to specifically detect *Lactobacillus acidophilus* even under conditions where other intraoral bacterium is present.

EFFECT OF THE INVENTION

Since the substrate recognition element in the biosensor of the invention is resistant to enzymolysis and drying, the biosensor is characterized in that its detection sensitivity for target bacterium is not impaired depending on the storage condition of the biosensor or depending on the measuring sample. In addition, the substrate recognition element of the biosensor of the invention does not contain agents that are harmful to the human body, and therefore the substrate recognition element can be directly inserted into the mouth to allow direct measurement of intraoral bacterium in saliva.

Moreover, since the substrate recognition element of the biosensor of the invention contains an aptamer(s) that binds with a protein comprising any of the amino acid sequences as set forth in SEQ ID NO: 1-25, it is possible to accomplish specific detection of *Streptococcus mutans, Streptococcus sobrinus* or *Lactobacillus acidophilus.*

BEST MODE FOR CARRYING OUT THE INVENTION

Preferred embodiments of the invention will now be described in detail.

The biosensor of the invention is characterized by comprising a microbe-binding aptamer(s) in the substrate recognition element.

The term "microbe" is used herein to refer to bacterium or filamentous fungus, and the term "intraoral bacterium" is used herein to refer to indigenous bacterium residing in the mouth.

An "aptamer(s)" is a nucleic acid molecule with the ability to bind to various compounds such as proteins or saccharides. Because an aptamer(s) has high specificity and affinity similar to antibodies, the biosensor is capable of highly sensitive detection of target bacterium.

The biosensor preferably comprises an aptamer(s) that binds with an intraoral bacterium at the substrate recognition element, and among intraoral bacterium, the aptamer(s) in the substrate recognition element most preferably binds with a bacterium that causes caries or periodontal disease.

As examples of cariogenic bacteria there may be mentioned *Streptococcus mutans, Streptococcus sobrinus, Lactobacillus casei, Lactobacillus fermentum, Lactobacillus plantarum* and *Lactobacillus acidophilus*, and as examples of periodontal bacteria there may be mentioned *Porphyromonas gingivalis, Tannerella forsythensis, Treponema denticora, Prevotella intermedia, Actinobacillus actinomycetemcomitans, Fusobacterium nucleatum, Eikenella corrodens, Capnocytophaga* sp., *Campylobacter rectus, Prevotella denticola, Actinomyces viscosus, Actinomyces naeslundii* and *Veillonella parvula.*

The biosensor more preferably contains in its substrate recognition element an aptamer(s) that binds with *Streptococcus mutans, Streptococcus sobrinus* or *Lactobacillus acidophilus*, among the cariogenic bacteria mentioned above.

The biosensor is characterized in that the aptamer(s) binds with a bacterial cell surface molecule, and examples of bacterial cell surface molecules that are specifically found on the cell surfaces of cariogenic bacterium include macromolecular protein antigens, PAc-like proteins, antigen A (III), glucan bond protein, lipoteichoic acid and glucosyltransferase.

As bacterial cell surface molecules that are specifically found on the cell surfaces of *Streptococcus mutans* there are preferred cell surface antigen SpaP (SEQ ID NO: 1 and 26), Cell wall-associated protein precursor WapA (SEQ ID NO: 2 and 27), Glucan-binding protein A, GbpA (SEQ ID NO: 3 and 28), Glucan-binding protein C, GbpC (SEQ ID NO: 4 and 29), glucosyltransferase-I (SEQ ID NO: 5 and 30), glucosyltransferase-S (SEQ ID NO: 6 and 31), glucosyltransferase-SI (SEQ ID NO: 7 and 32), *S. mutans* glucan-binding protein (gbp) (SEQ ID NO: 8 and 33), *S. mutans* GS-5 scrB (SEQ ID NO: 9 and 34), *S. mutans* sr (SEQ ID NO: 10 and 35), *S. mutans* wall-associated protein (wapA) (SEQ ID NO: 11 and 36), *S. mutans* spaP (SEQ ID NO: 12 and 37), *Streptococcus mutans* pac (SEQ ID NO: 13 and 38), Mutacin W NlmA (SEQ ID NO: 14 and 39) and Mutacin IV NlmB (SEQ ID NO: 15 and 40).

As bacterial cell surface molecules that are specifically found on the cell surfaces of *Streptococcus sobrinus* there are preferred glucosyltransferase-I (SEQ ID NO: 16 and 41), glucosyltransferase-S1 (SEQ ID NO: 17 and 42), glucosyltransferase-S2 (SEQ ID NO: 18 and 43), Dei (SEQ ID NO: 19 and 44), Surface protein antigen PAg (SEQ ID NO: 20 and 45) and *S. sobrinus* spaA (SEQ ID NO: 21 and 46).

As bacterial cell surface molecules that are specifically found on the cell surfaces of *Lactobacillus acidophilus* there are preferred Acidocin. A (SEQ ID NO: 22 and 47), Acidocin. B (SEQ ID NO: 23 and 48), Acidocin. M (SEQ ID NO: 24 and 49) and Acidocin 8912 (SEQ ID NO: 25 and 50).

The aptamer(s) can be obtained by chemical synthesis of nucleic acid having the nucleotide sequence of interest by a method commonly used by those skilled in the art, and screening based on specific binding activity for the bacterial cell surface molecule specifically found on the cell surfaces of the target bacterium. A specific example is the following method.

First a bacterial cell surface molecule found specifically on the cell surface of the target bacterium is selected, the nucleotide sequence coding for the amino acid sequence of the bacterial cell surface molecule is processed with a computer evolution program to generate 10 generations of nucleotide sequences in the computer, and the nucleotide sequences are used as candidate aptamers that bind with the target bacterium. The computer evolution program can be written with Visual Basic using a common genetic algorithm with reference to the one by Ikebukuro (Nucleic Acids Res., 2005, Vol. 33, e108).

Next oligo DNA composed of the nucleotide sequences obtained as candidates by the aforementioned processing is chemically synthesized, and the candidates that actually exhibit high-affinity binding with the target bacterium are recovered as aptamers and used as templates for PCR amplification to obtain large amounts of aptamers that bind the target bacterium.

From the viewpoint of easier production and increased ability, the aptamer(s) is preferably a DNA aptamer(s), and its base length is preferably 10-200 and more preferably 20-100.

Preferred embodiments of the biosensor of the invention will now be explained.

As a first embodiment of the biosensor of the invention, there may be mentioned a sensor wherein the aptamer(s) that specifically bind with the target bacterium are labeled with an enzyme or fluorescent dye, and immobilized as the substrate recognition element on a board.

FIG. 1 is a perspective view of the first embodiment of the biosensor of the invention.

The biosensor 10 shown in FIG. 1 comprises a board 1 and a substrate recognition element 3 formed on the board 1, wherein an aptamer(s) 5 labeled with an enzyme 7 or fluorescent dye 7 is bound to the substrate recognition element 3.

For the biosensor 10 of the first embodiment, a test sample (for example, saliva or body fluid) is dropped onto the substrate recognition element 3, or the substrate recognition element 3 is inserted into the mouth and contacted with saliva, to allow binding of the target bacterium with the aptamer(s) 5, whereupon the enzyme 7 bound to the aptamer(s) 5 participates in an enzyme reaction that alters the absorbance of the reaction substrate, or a change is effected in the fluorescent anisotropy of the fluorescent dye 7, and this change is detected to allow detection of the target bacterium.

The method of binding the aptamer(s) 5 to the surface of the board 1 is not particularly restricted, and any method commonly employed in the technical field may be used. For example, the surface of the board 1 may be treated with poly-L-lysine and a solution containing the prescribed amount of aptamer(s) 5 spotted thereon, for covalent bonding of the poly-L-lysine and aptamer(s) 5. Also, functional groups may be introduced at the ends of the aptamer(s) 5 for covalent bonding of these functional groups with functional groups on the surface of the board 1.

Examples for the enzyme 7 used to label the aptamer(s) 5 include horseradish peroxidase (HRP), β-D-galactosidase, alkaline phosphatase, glucose oxidase and glucose-6-phosphate dehydrogenase.

As examples of substrates for horseradish peroxidase (HRP) there may be mentioned 3,3'-diaminobenzidine tetra hydrochloride (DAB), 3-amino-9-ethyl carbazole (AEC), 5-aminosalitylic acid, 2,2'-azinobis (3-ethylbenzothiazoline-6-sulfonic acid (ABTS), o-phenylenediamine (o-PDA), tetramethylbenzidine (TMB), tyramine and 3-(p-hydroxyphenyl)-propionic acid HPPA). As examples of substrates for β-D-galactosidase there may be mentioned o-nitrophenyl-β-D-galactoside and 4-methylumbelliferyl-β-D-galactoside, and as examples of substrates for a e phosphatase there may be mentioned bromochloroindole phosphate/nitro blue tetrazolium, p-nitrophenylphosphate and 4-methylumbelliferyl phosphate. As an example of a substrate for glucose oxidase there may be mentioned β-D-glucose, and this enzyme also exhibits coloration or luminescence in the presence of HRP and its substrate. As an example of a substrate for glucose-6-phosphate dehydrogenase there may be mentioned glucose-6-phosphate, and this enzyme may be used in the presence of NADP to measure the absorbance of NADPH produced by reduction of NADP.

Examples for the fluorescent dye 7 include Texas Red (excitation wavelength of 590 nm, fluorescent wavelength of 615 nm), RITC (rhodamine; excitation wavelength of 520 nm, fluorescent wavelength of 580 nm), FITC (fluorescein isothiocyanate; excitation wavelength of 495 nm, fluorescent wavelength of 520 nm), PE (phycoerythrin; excitation wavelengths of 488 nm and 545 nm, fluorescent wavelength of 580 nm), Cy2 (excitation wavelength of 489 nm, fluorescent wavelength of 505 nm), Cy3 (excitation wavelength of 552 nm, fluorescent wavelength of 565 nm), Cy3.5 (excitation wavelength of 581 nm, fluorescent wavelength of 596 nm), Cy5 (excitation wavelength of 650 nm, fluorescent wavelength of 667 nm), Cy5.5 (excitation wavelength of 678 nm, fluorescent wavelength of 703 nm), AMCA (7-amino-4-methylcoumarin-3-acetic acid; excitation wavelength of 350 nm, fluorescent wavelength of 450 nm), APC (allophycocyanin; excitation wavelengths of 633 nm and 635 nm, fluorescent wavelength of 670 nm), PAM (carboxyfluorescein; excitation wavelength of 494 nm, fluorescent wavelength of 518 nm), HEX hexachlorofluorescein; excitation wavelength of 535 nm, fluorescent wavelength of 556 nm), TAMRA (carbotetramethylrhodamine; excitation wavelength of 521 nm, fluorescent wavelength of 536 nm), TET (carbotetrachlorofluorescein; excitation wavelength of 555 nm, fluorescent wavelength of 580 nm) and GFP (Green Fluorescent Protein; excitation wavelength of 488 nm, fluorescent wavelength of 460 nm). There are no particular restrictions on the method of labeling the aptamer(s) 5 with the enzyme 7 or fluorescent dye 7, and any labeling method commonly employed in the technical field may be used.

As a second embodiment of the biosensor of the invention, there may be mentioned a sensor wherein aptamer(s) that specifically binds with the target bacterium is immobilized as the substrate recognition element on a board, without being labeled with an enzyme 7 or fluorescent dye 7.

FIG. 2 is a perspective view of the second embodiment of the biosensor of the invention.

The biosensor 20 shown in FIG. 2 comprises a board 1 and a substrate recognition element 3 formed on the board 1, with aptamer(s) 5 bound to the substrate recognition element 3.

For the biosensor 20 of the second embodiment, first a sample (for example, saliva or body fluid) is dropped onto the substrate recognition element 3, or the substrate recognition element 3 is inserted into the mouth and contacted with saliva, to allow binding of the target bacterium with the aptamer(s) 5, after which the substrate recognition element 3 is thoroughly rinsed in buffer and the substrate recognition element 3 is contacted with a solution containing enzyme- or fluorescent dye-labeled antibody or aptamer that specifically recognizes the target bacterium, to bind the antibody or aptamer to the target bacterium that is bound to the aptamer(s) 5. Next, the substrate recognition element 3 is thoroughly rinsed to remove the non-specific binding, and the activity exhibited by the enzyme or the fluorescence emitted by the fluorescent dye, with which the antibody or aptamer is labeled, is detected to allow detection of the target bacterium.

Binding of the aptamer(s) 5 to the board 1 and examples of fluorescent dyes are the same as described for the first embodiment of the biosensor of the invention.

As a third embodiment of the biosensor of the invention there may be mentioned a sensor wherein an electrolyte solution is placed in a two-electrode type electrochemical cell comprising a reference electrode and a working electrode having the aptamer(s) that specifically binds with the target bacterium, an alkanethiol and ferrocene immobilized on the electrode. The sensor may also be a 3-electrode system comprising a working electrode, counter electrode and reference electrode.

FIG. 3 is a perspective view of the third embodiment of the biosensor of the invention.

The biosensor 30 shown in FIG. 3 comprises an insulating board 2, a working electrode 11 and reference electrode 13 formed on the insulating board 2, and a lead wire 15 connecting them. The alkanethiol 21 is bound to the working electrode 11, the ferrocene 23 is bound to the alkanethiol 21 and the aptamer(s) 5 is bound to the ferrocene 23. A sheath 6 is formed around the working electrode 11, reference electrode 13, alkanethiol 21 and ferrocene 23 on the insulating board 2 of the biosensor 30, and the interior surrounded by the sheath 6 serves as the reaction zone 17 in which the sample is retained. The entirety of the working electrode 11, reference electrode 13, alkanethiol 21, ferrocene 23 and sheath 6 constitutes the substrate recognition element 3.

For the biosensor of the third embodiment, a constant voltage is applied between the working electrode 11 and reference electrode 13, and after reaching a steady current, the sample (for example, saliva or body fluid) is added to the reaction zone 17 and the current value change is measured to detect the target bacterium. The concentration of the target bacterium may be calculated according to a standard curve drawn from a solution containing a standard concentration of the target bacterium.

The electrode material is a gold electrode for the working electrode 11 and an AgAgCl electrode for the reference electrode 13, for example.

The method in which the a alkanethiol 21, the ferrocene 23 and the aptamer(s) 5 that specifically binds with the target bacterium is immobilized on the electrode may be a method in which, first, biotin-labeled alkanethiol 21 is bonded to the working electrode 11, avidin-labeled ferrocene 23 is bound to the alkanethiol 21 by biotin-avidin reaction, and biotin-labeled aptamer(s) 5 is bound to the ferrocene 23.

EXAMPLES

The present invention will now be explained in greater detail with reference to examples, with the understanding that the invention is not meant to be limited to these examples.

Example 1

Screening of Aptamers that Bind Specifically to *Streptococcus mutans*

*Streptococcus mutans* pac (SEQ ID NO: 13) was selected as a bacterial cell surface molecule specifically found on *Streptococcus mutans*, and aptamers that specifically bind to this protein were screened.

First, the nucleotide sequence of *Streptococcus mutans* pac represented by SEQ ID NO: 13 of the Sequence Listing, as the aptamer-binding site, was processed with a computer evolution program to generate 10 generations of nucleotide sequences on the computer, and the nucleotide sequences were used as candidate *Streptococcus mutans*-binding aptamers. The computer evolution program was written with Visual Basic using a common genetic algorithm with reference to the one by Ikebukuro Nucleic Acids Res., 2005, Vol. 33, e108).

Next, oligo DNA consisting of the candidate nucleotide sequences was chemically synthesized, and those exhibiting specific binding for *Streptococcus mutans* were recovered as aptamers and used as templates for PCR to prepare large amounts of aptamers that specifically binds to *Streptococcus mutans* (hereinafter referred to as "*S. mutans*-binding aptamer").

An *S. mutans*-binding aptamer(s) obtained in this manner was labeled at the ends with biotin and used in the following experiment.

Example 2

Detection of *Streptococcus mutans* with Aptamer(s)

Detection of Streptococcus mutans by ELISA was attempted, using *S. mutans*-binding aptamer(s) instead of anti-*Streptococcus mutans* antibody.

First, *Streptococcus mutans* was suspended in PBS and cell suspensions of different concentrations ($1\times10^4$, $1\times10^5$, $1\times10^6$, $1\times10^7$, $1\times10^8$ and $1\times10^9$ CFU/mL) were prepared. The prepared cell suspensions were added in 100 μL aliquots to each well of a poly-L-lysine-coated 96-well plate, and were incubated for a prescribed period of time to fix the cells at the bottoms of the wells.

To each of the cell-fixed wells there was added 50 μg of the biotin-labeled *S. mutans*-binding aptamer(s) prepared in Example 1, and after incubation at 25° C. for 1 hour, they were rinsed with PBS to remove the biotin-labeled *S. mutans*-binding aptamer(s) that had not bound to the cells.

Next, HRP-labeled steptavidin was added to each well, and after incubation at 25° C. for 1 hour, each well was thoroughly rinsed with PBS and o-PDA was added to each well as a chromogenic substrate for 15 minutes of reaction. After then adding 6N sulfuric acid to stop the reaction, the absorbance at 492 nm was measured with a microplate reader.

The results demonstrated that the biotin-labeled *S. mutans*-binding aptamer(s) can detect $1\times10^4$ CFU/mL *Streptococcus mutans* with high sensitivity (solid graph line in FIG. 4).

Comparative Example 1

Detection of *Streptococcus mutans* with Anti-*Streptococcus mutans Antibody*

Detection of *Streptococcus mutans* by ELISA was attempted using anti-*Streptococcus mutans* antibody, for comparison with the detection sensitivity by ELISA using the *S. mutans*-binding aptamer(s) of Example 2.

In the same manner as Example 2, *Streptococcus mutans* was suspended in PBS and cell suspensions of different concentrations ($1\times10^4$, $1\times10^5$, $1\times10^6$, $1\times10^7$, $1\times10^8$ and $1\times10^9$ CFU/mL) were prepared. The prepared cell suspensions were added in 100 μL aliquots to each well of a poly-L-lysine-coated 96-well plate, and were incubated for a prescribed period of time to fix the cells at the bottoms of the wells.

To each of the cell-fixed wells there was added 100 μL of 50-fold diluted anti-*Streptococcus mutans* antibody (rabbit anti-*Streptococcus mutans* IgG antibody), and after incubation at 25° C. for 1 hour, they were rinsed with PBS to remove the rabbit anti-*Streptococcus mutans* IgG antibody that had not bound to the cells.

Next 1% skim milk was added to each well for blocking treatment, and ten biotin-labeled goat anti-rabbit IgG antibody was added prior to incubation at 25° C. for 1 hour, and each well was thoroughly rinsed with PBS.

HRP-labeled streptavidin was then added to each well, and after incubation at 25° C. for 1 hour, each well was thoroughly rinsed with PBS and o-PDA was added to each well as a chromogenic substrate for 15 minutes of reaction. After then adding 6N sulfuric acid to stop the reaction, the absorbance at 492 nm was measured with a microplate reader.

The results demonstrated that rabbit anti-*Streptococcus mutans* IgG antibody could not detect *Streptococcus mutans* at a concentration of below $1\times10^5$ CFU/mL, and detection could only be made at a concentration of $1\times10^6$ CFU/mL or higher (dotted graph line in FIG. 4).

These results indicated that the *S. mutans*-binding aptamer(s) has a detection sensitivity of at least 100 times higher than rabbit anti-*Streptococcus mutans* IgG antibody, suggesting that from the viewpoint of detection sensitivity, the aptamer(s) is more suitable for detection of the bacterium than antibody.

Example 3

Detection of *Streptococcus mutans* with Biosensor Comprising *S. mutans*-binding Aptamer(s) in Substrate Recognition Element (Electrochemical Method)

A sensor was constructed with electrolyte solution in a 3-electrode type electrochemical cell comprising a working electrode having the *S. mutans*-binding aptamer(s), alkanethiol and ferrocene immobilized on the electrode, and a counter electrode and a reference electrode, and was used to detect *Streptococcus mutans* in a test sample.

First, biotin-labeled alkanethiol was bonded to the surface of the gold electrode and the gold electrode was rinsed with PBS, and then the avidin-labeled ferrocene was bound to the alkanethiol by biotin-avidin reaction, the gold electrode was again rinsed with PBS, and finally the biotin-labeled *S. mutans*-binding aptamer(s) prepared in Example 1 was bound to the ferrocene by biotin-avidin reaction to form the working electrode (substrate recognition element).

A 3-electrode type electrochemical cell comprising the obtained working electrode, a counter electrode (Au) and a reference electrode (Ag/AgCl) was then completed, to construct a biosensor containing PBS in the cell.

A constant voltage was applied to the working electrode of the biosensor obtained in this manner, and upon reaching a steady current, *Streptococcus mutans* suspensions at different concentrations ($1\times10^4$, $1\times10^5$, $1\times10^6$, $1\times10^7$, $1\times10^8$ and $1\times10^9$ CFU/mL) were added and the current value change was measured.

FIG. 5 shows the results for detection of *Streptococcus mutans* by an electrochemical method using the biosensor comprising the *S. mutans*-binding aptamer(s) in the substrate recognition element.

The results demonstrated that detection of *Streptococcus mutans* is possible at a concentration of $1\times10^6$ CFU/mL and higher using a biosensor with the *S. mutans*-binding aptamer(s) in the substrate recognition element.

EXPLANATION OF SYMBOLS

Figure 1:
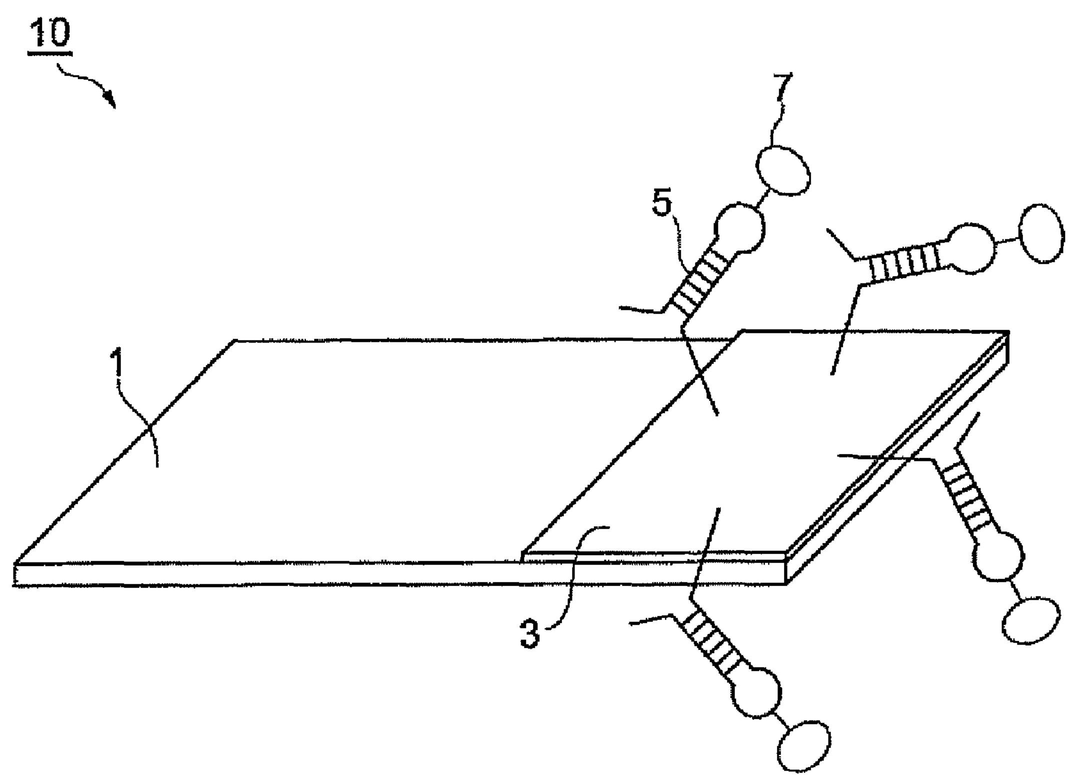
FIG. 1 is a perspective view of the first embodiment of the biosensor of the invention.
Figure 2:
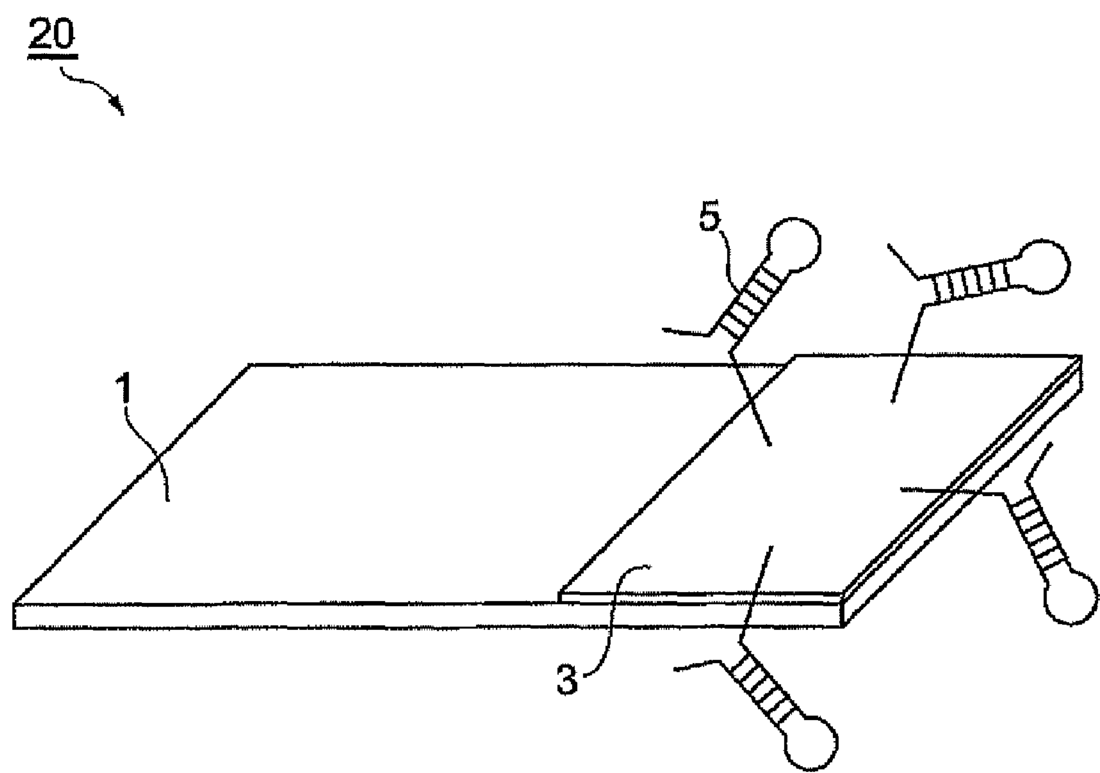
FIG. 2 is a perspective view of the second embodiment of the biosensor of the invention.
Figure 3:
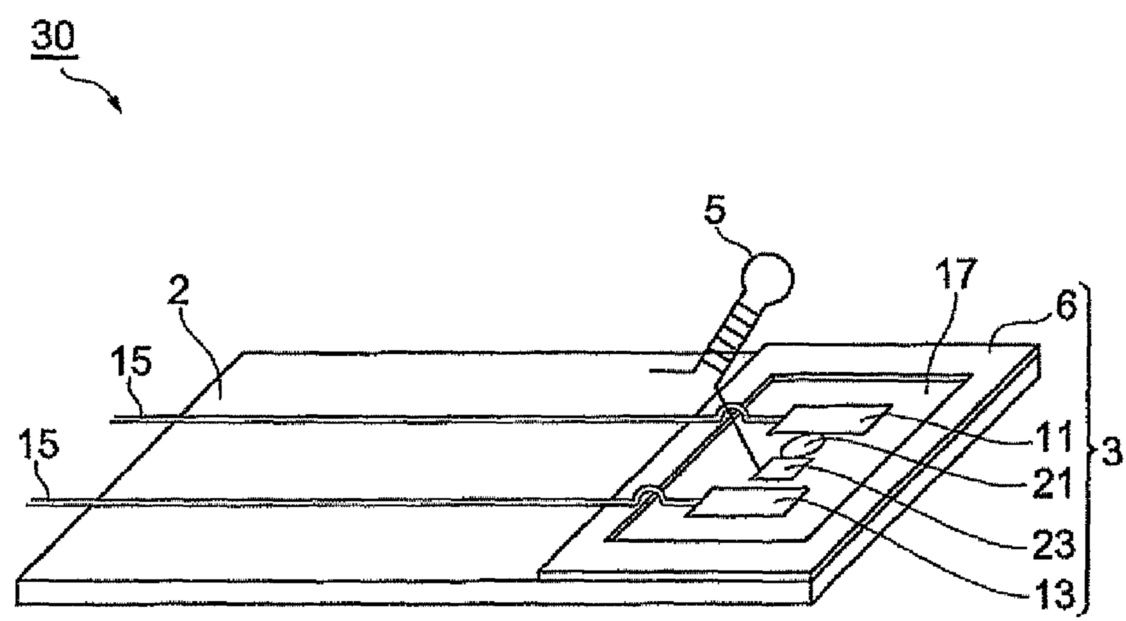
FIG. 3 is a perspective view of the third embodiment of the biosensor of the invention.
Figure 4:
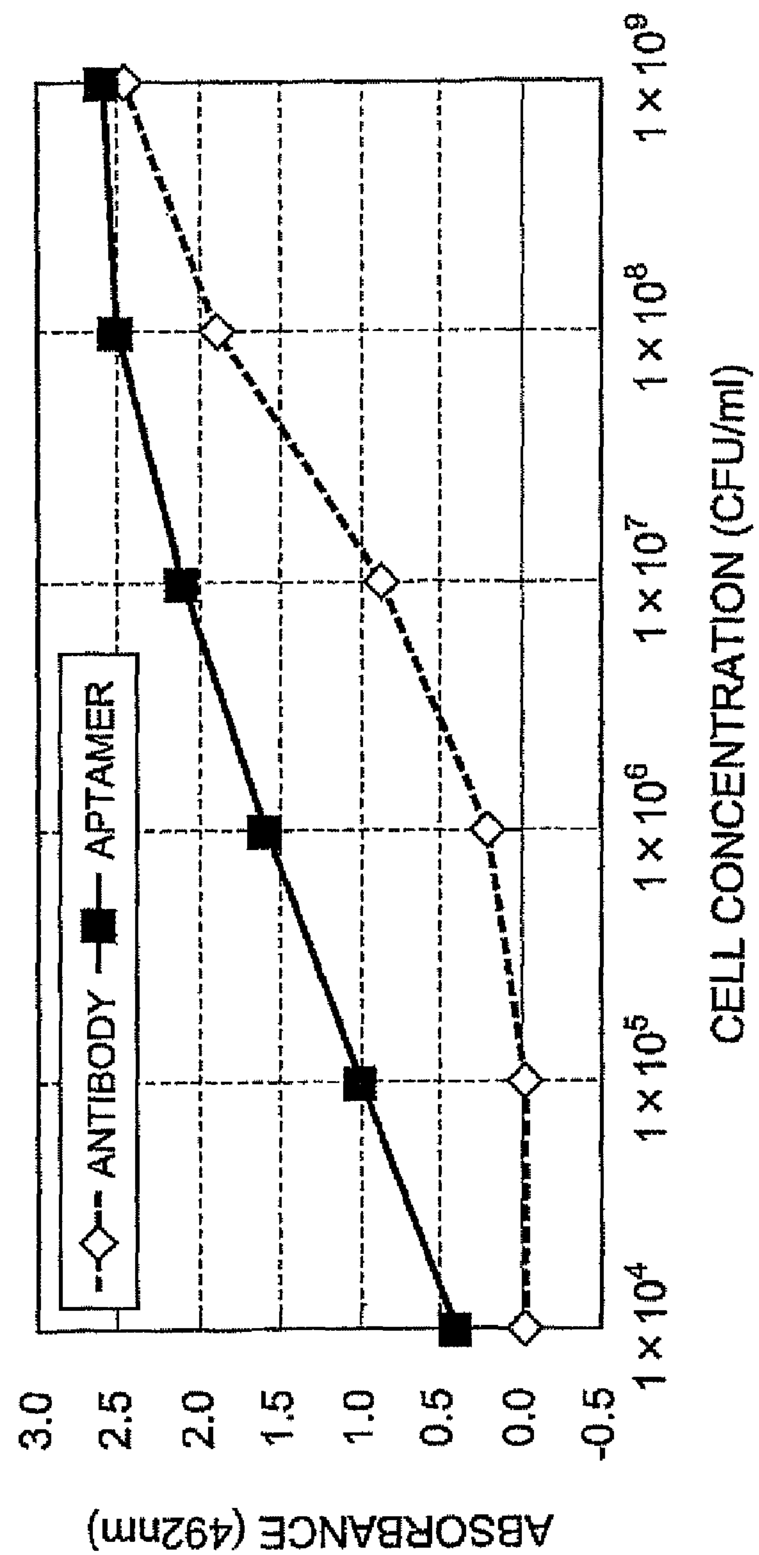
FIG. 4 is a graph showing a comparison of the detection sensitivities for detection of *Streptococcus mutans*, by ELISA using anti-*Streptococcus mutans* antibody, and by ELISA using an *S. mutans*-binding aptamer(s) instead of anti-*Streptococcus mutans* antibody.
Figure 5:
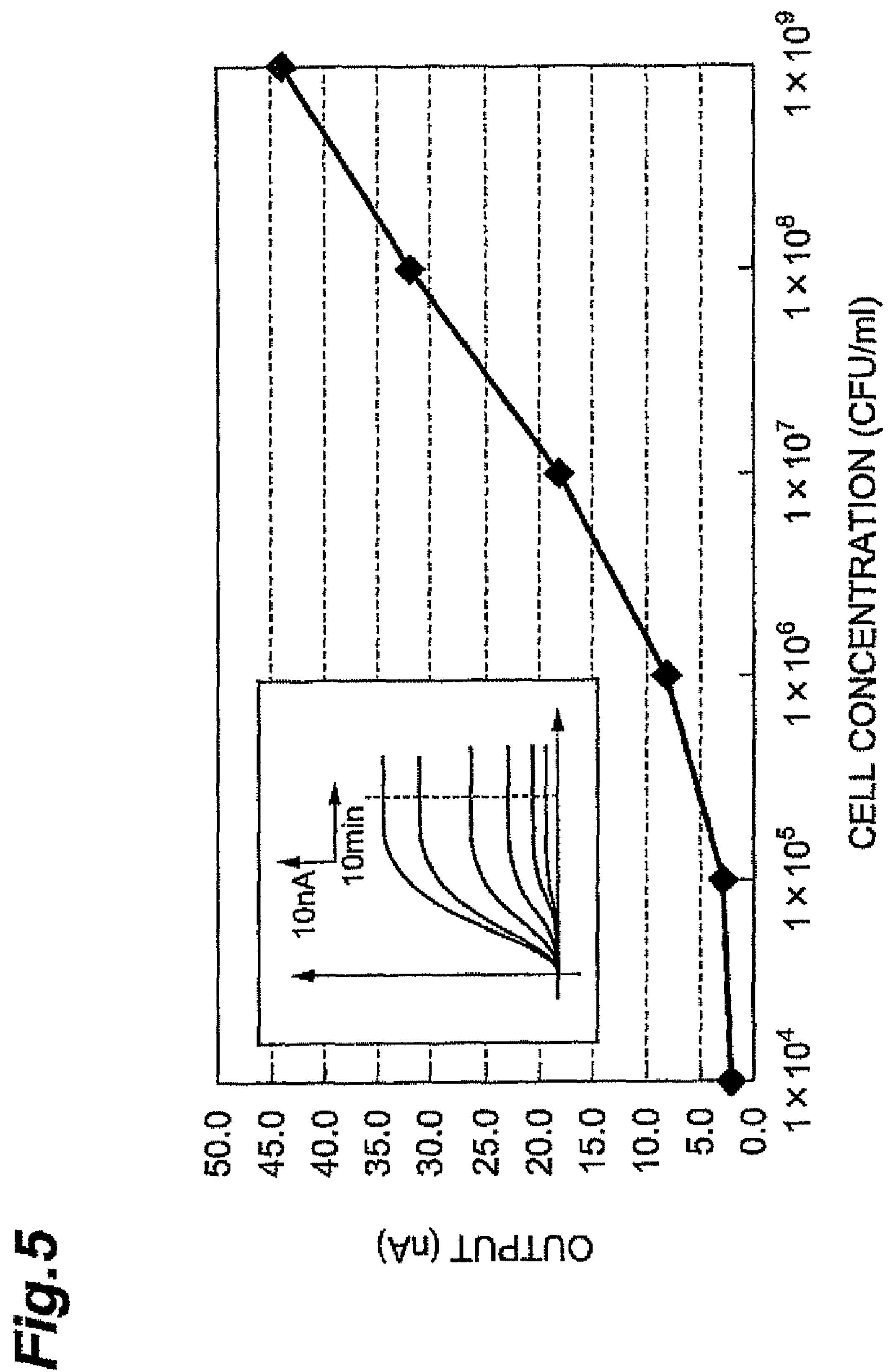
FIG. 5 is a graph showing the results for detection of *Streptococcus mutans* by an electrochemical method using a biosensor comprising an *S. mutans*-binding aptamer(s) in the substrate recognition element.

1: Board, 2: insulating board, 3: substrate recognition element, 5: aptamer(s), 6: sheath, 7: enzyme or fluorescent dye, 10, 20, 30: biosensor, 11: working electrode, 13: reference electrode, 15: lead wire, 17: reaction zone, 21: a alkanethiol, 23: ferrocene.

What is claimed is:

1. A biosensor comprising a microbe-binding apatmer(s) in a substrate recognition element, wherein the microbe is *Streptococcus mutans* and the aptamer(s) binds with a protein comprising any of the amino acid sequences as set forth in SEQ ID NO: 1-12, 14, and 15.

2. A biosensor comprising a microbe-binding aptamer(s) in a substrate recognition element, wherein the microbe is *Streptococcus sobrinus* and the aptamer(s) binds with a protein comprising any of the amino acid sequences as set forth in SEQ ID NO: 16-20.

3. A biosensor comprising a microbe-binding aptamer(s) in a substrate recognition element, wherein the microbe is *Lactobacillus acidophilus*.

4. A biosensor according to claim 3, wherein the aptamer(s) binds with a protein comprising any of the amino acid sequences as set forth in SEQ ID NO: 22-25.

* * * * *